US009155800B2

(12) United States Patent
Abu Bakar, Ag. et al.

(10) Patent No.: US 9,155,800 B2
(45) Date of Patent: Oct. 13, 2015

(54) ANTIMICROBIAL FUSION COMPOUNDS AND USES THEREOF

(75) Inventors: Muhammad Sagaf Abu Bakar, Ag., Sabah (MY); Eng Huan Ung, Sabah (MY)

(73) Assignee: VALIANT BIOPHARMA SDN BHD, Selangor (MY)

( * ) Notice: Subject to any disclaimer, the term of this patent is extended or adjusted under 35 U.S.C. 154(b) by 0 days.

(21) Appl. No.: 13/978,224

(22) PCT Filed: Jan. 9, 2012

(86) PCT No.: PCT/MY2012/000003
§ 371 (c)(1),
(2), (4) Date: Jul. 3, 2013

(87) PCT Pub. No.: WO2012/093931
PCT Pub. Date: Jul. 12, 2012

(65) Prior Publication Data
US 2013/0336955 A1    Dec. 19, 2013

(30) Foreign Application Priority Data
Jan. 7, 2011  (MY) ........................ PI2011000092

(51) Int. Cl.
*A61K 47/48*    (2006.01)
*C07K 14/47*    (2006.01)
*A61K 38/17*    (2006.01)

(52) U.S. Cl.
CPC ....... *A61K 47/48246* (2013.01); *C07K 14/4723* (2013.01); *A61K 38/1709* (2013.01); *C07K 2319/00* (2013.01)

(58) Field of Classification Search
CPC .............................................. A61K 47/48246
See application file for complete search history.

(56) References Cited

U.S. PATENT DOCUMENTS

2004/0266994 A1*  12/2004  Stirpe et al. .............. 530/391.1

OTHER PUBLICATIONS

IVAI Report. May-Jun. 2009, vol. 13 No. 3: 1-20.*
Yasin et al. Theta defensins protect cells from infection by herpes simplex virus by inhibiting viral adhesion and entry. J Virol. May 2004;78(10):5147-56.*
Lorin et al. The antimicrobial peptide Dermaseptin S4 inhibits HIV-1 infectivity in vitro. Virology 334 (2005) 264-275.*
Levy et al. Engineering a bifunctional starch-cellulose cross-bridge protein. Biomaterials. May 2004;25(10):1841-9.*
Wang et al. Anti-HIV and anti-tumor protein MAP30, a 30 kDa single-strand type-I RIP, shares similar secondary structure and beta-sheet topology with the a chain of ricin, a type-II RIP. Protein Sci. Jan. 2000;9(1):138-44.*
Owen et al. RC-101, a retrocyclin-1 analogue with enhanced activity against primary HIV type 1 isolates. AIDS Res Hum Retroviruses. Nov. 2004;20(11):1157-65.*
Küttner et al. Biotechniques. Linker peptide and affinity tag for detection and purification of single-chain Fv fragments. Biotechniques. May 2004;36(5):864-70.*
Steiner et al. Signal sequences directing cotranslational translocation expand the range of proteins amenable to phage display. Nat Biotechnol. Jul. 2006;24(7):823-31.*
Mor et al. The NH2-terminal a-Helical Domain 1-18 of Dermaseptin Is Responsible for Antimicrobial Activity. J Biol Chem. Jan. 21, 1994;269(3)1934-9.*
Meyer et al. Protein—Protein Interactions: A Molecular Cloning Manual, © 2002 by Cold Spring Harbor Laboratory Press, Chapter 18. pp. 329-338.*
Sambrook and Russel, Molecular Cloning: A Laboratory Manual, Cold Springs Harbor Laboratory, New York (2001).*
International Search Report for International Application No. PCT/MY2012/000003. Dated Apr. 11, 2012. 5 pages.
International Preliminary Report on Patentability for PCT/MY2012/000003. Dated Dec. 4, 2012. 34 pages.
Written Opinion of the International Searching Authority for PCT/MY2012/000003. Dated Apr. 11, 2012. 7 pages.

* cited by examiner

*Primary Examiner* — Karlheinz R Skowronek
*Assistant Examiner* — Jia-Hai Lee
(74) *Attorney, Agent, or Firm* — Lathrop & Gage LLP; Brian C. Trinque

(57) ABSTRACT

A fusion protein comprising at least one Type 1 Ribosome Inactivating Protein, polypeptide B; and at least one polypeptide A capable of viral entry inhibition; and/or at least one Cationic AntiMicrobial Peptide, polypeptide C.

16 Claims, 16 Drawing Sheets

```
  1 ATGAAATACCTGCTGCCGACCGCTGCTGCTGGTCTGCTGCTCCTCGCTGCCCAGCCGGCG
  1  M  K  Y  L  L  P  T  A  A  A  G  L  L  L  L  A  A  Q  P  A
 61 ATGGCCATGGGCGTATTTGCCGTTGCATTTGCGGCCGTGGCATTTGCCGCTGCATCTGT
 21  M  A  M  G  R  I  C  R  C  I  C  G  R  G  I  C  R  C  I  C
121 GGCGTGCCGGGTGTTGGTGTTCCGGGTGTGGGTGGTGCGACCGGATCCGATGTGAACTTT
 41  G  V  P  G  V  G  V  P  G  V  G  G  A  T  G  S  D  V  N  F
181 GATCTGAGCACCGCGACCGCGAAAACCTATACCAAATTCATCGAAGATTTTCGTGCGACC
 61  D  L  S  T  A  T  A  K  T  Y  T  K  F  I  E  D  F  R  A  T
241 CTGCCGTTTAGCCATAAAGTGTATGATATCCCGCTGCTGTATAGCACCATTAGCGATAGC
 81  L  P  F  S  H  K  V  Y  D  I  P  L  L  Y  S  T  I  S  D  S
301 CGTCGTTTTATTCTGCTGGATCTGACCAGCTATGCGTATGAAACCATTAGCGTGGCGATT
101  R  R  F  I  L  L  D  L  T  S  Y  A  Y  E  T  I  S  V  A  I
361 GATGTGACCAACGTGTATGTGGTGGCGTATCGTACCCGTGATGTGAGCTACTTTTTCAAA
121  D  V  T  N  V  Y  V  V  A  Y  R  T  R  D  V  S  Y  F  F  K
421 GAAAGCCCGCCGGAAGCGTACAACATTCTGTTTAAAGGCACCCGTAAAATTACCCTGCCG
141  E  S  P  P  E  A  Y  N  I  L  F  K  G  T  R  K  I  T  L  P
481 TATACCGGCAACTATGAAAACCTGCAGACCGCGGCGCATAAAATTCGTGAAAACATCGAT
161  Y  T  G  N  Y  E  N  L  Q  T  A  A  H  K  I  R  E  N  I  D
541 CTGGGCCTGCCGGCCCTGAGCAGCGCGATTACCACCCTGTTTTATTATAACGCGCAGAGC
181  L  G  L  P  A  L  S  S  A  I  T  T  L  F  Y  Y  N  A  Q  S
601 GCGCCGAGCGCGCTGCTGGTGCTGATTCAGACCACCGCGGAAGCGGCGCGTTTTAAATAT
201  A  P  S  A  L  L  V  L  I  Q  T  T  A  E  A  A  R  F  K  Y
661 ATTGAACGCCACGTGGCGAAATATGTGGCGACCAACTTTAAACCGAACCTGGCCATTATT
221  I  E  R  H  V  A  K  Y  V  A  T  N  F  K  P  N  L  A  I  I
721 AGCCTGGAAAACCAGTGGAGCGCCCTGAGCAAACAAATTTTTCTGGCCCAGAACCAGGGC
241  S  L  E  N  Q  W  S  A  L  S  K  Q  I  F  L  A  Q  N  Q  G
781 GGCAAATTTCGTAATCCGGTGGATCTGATTAAACCGACCGGCGAACGTTTTCAGGTGACC
261  G  K  F  R  N  P  V  D  L  I  K  P  T  G  E  R  F  Q  V  T
841 AATGTGGATAGCGATGTGGTGAAAGGCAACATTAAACTGCTGCTGAACAGCCGTGCGAGC
281  N  V  D  S  D  V  V  K  G  N  I  K  L  L  L  N  S  R  A  S
901 ACCGCGGATGAAAACTTTATTACCACCATGACCCTGCTGGGCGAAAGCGTGGTGGAATTC
301  T  A  D  E  N  F  I  T  T  M  T  L  L  G  E  S  V  V  E  F
961 CCGTGGGCGCTGTGGAAAACCATGCTGAAAGAACTGGGCACGATGGCGCTGCATGCGGGT
321  P  W  A  L  W  K  T  M  L  K  E  L  G  T  M  A  L  H  A  G
1021 AAAGCGGCGCTGGGTGCGGCAGCGGATACCATTAGCCAGGGCACCCAGGTTCCGGGCGTG
341  K  A  A  L  G  A  A  A  D  T  I  S  Q  G  T  Q  V  P  G  V
1081 GGCGTTCCGGGCGTTGGTAAGCTTGCGGCCGCACTCGAGCACCACCACCACCACCACTGA
361  G  V  P  G  V  G  K  L  A  A  A  L  E  H  H  H  H  H  H  *
```

FIGURE 1

(A)
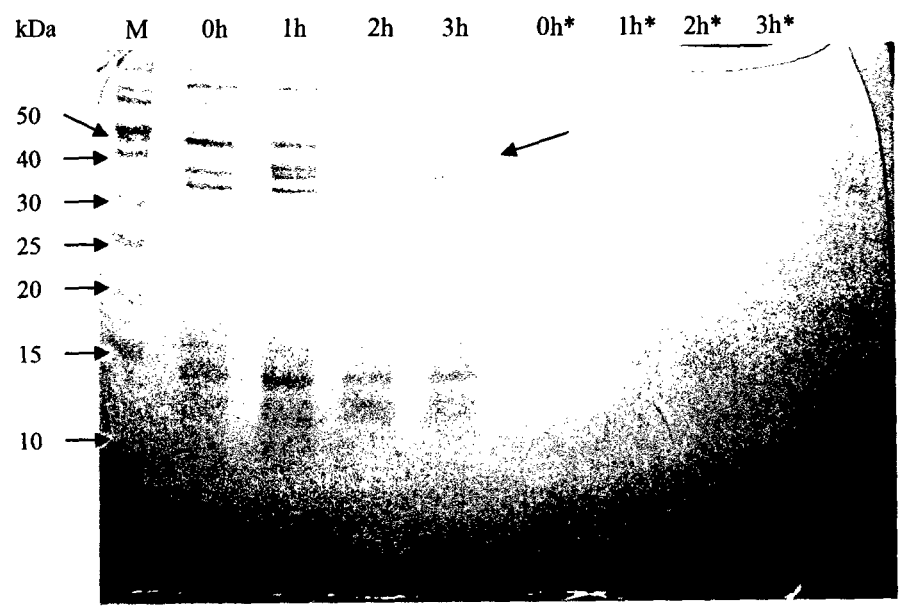
(B)
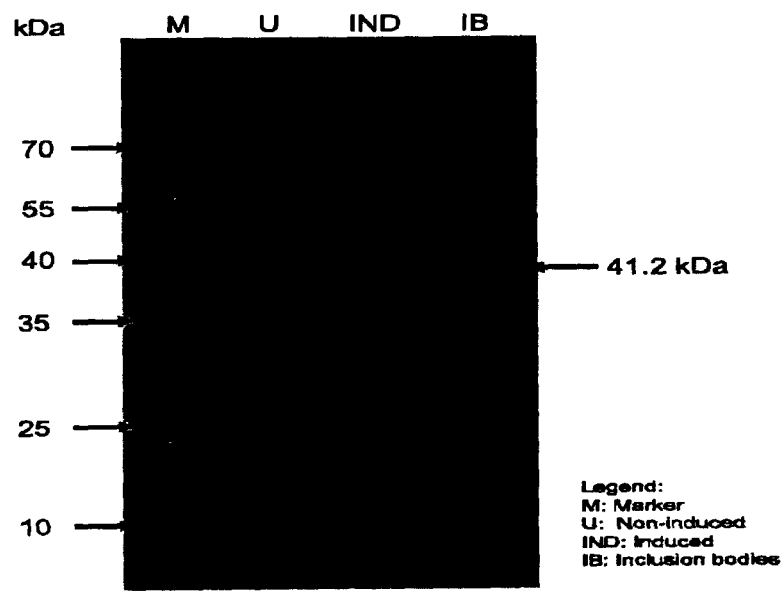
FIGURE 2

(A)
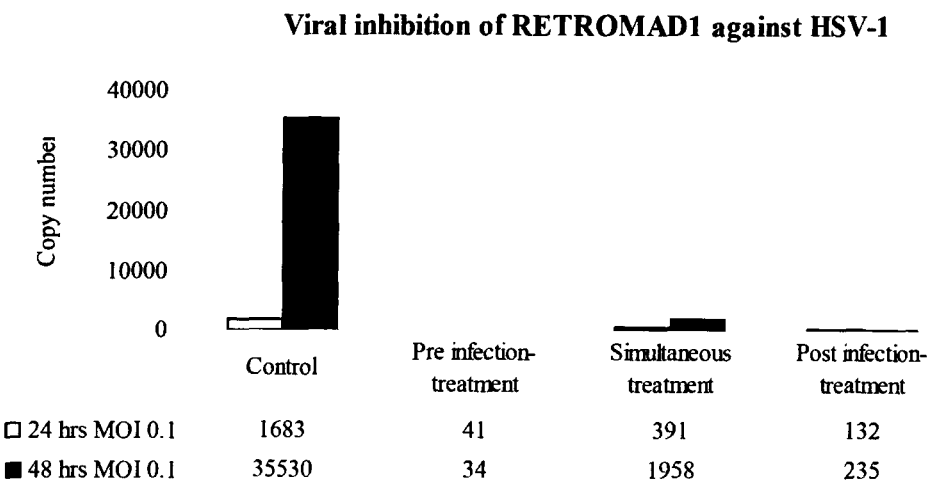
(B)
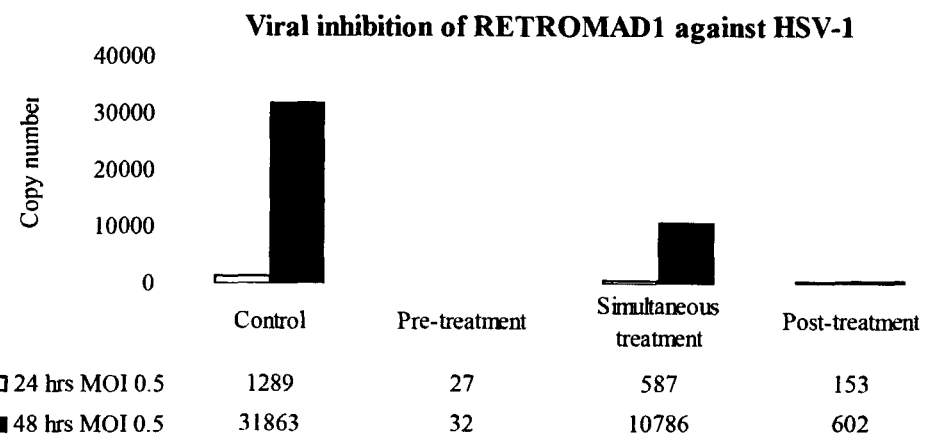
FIGURE 3

(A)
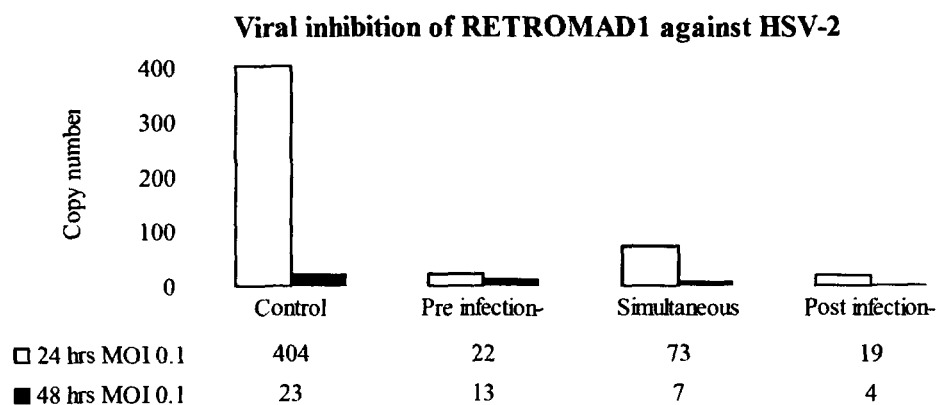
(B)
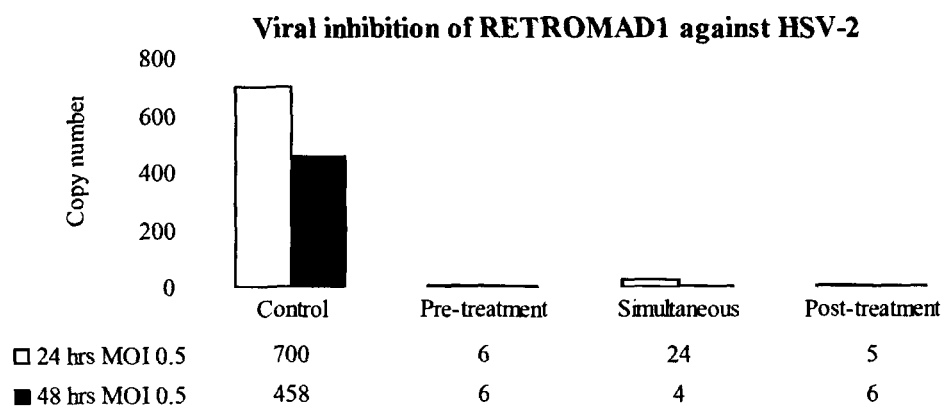
FIGURE 4

(A)
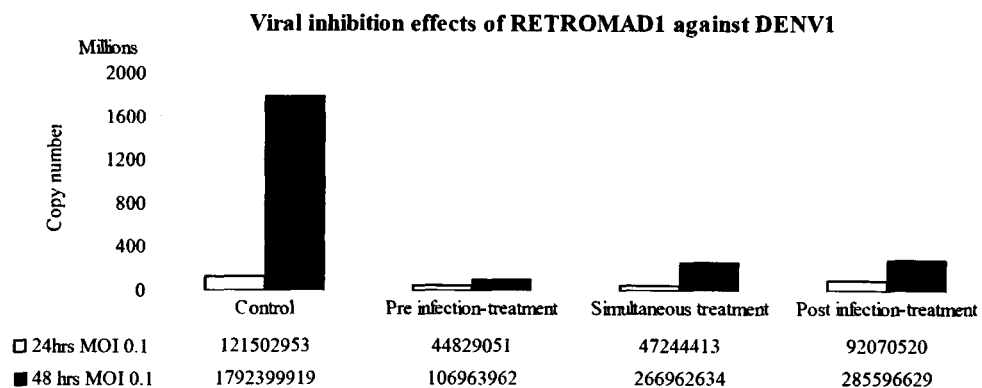
(B)
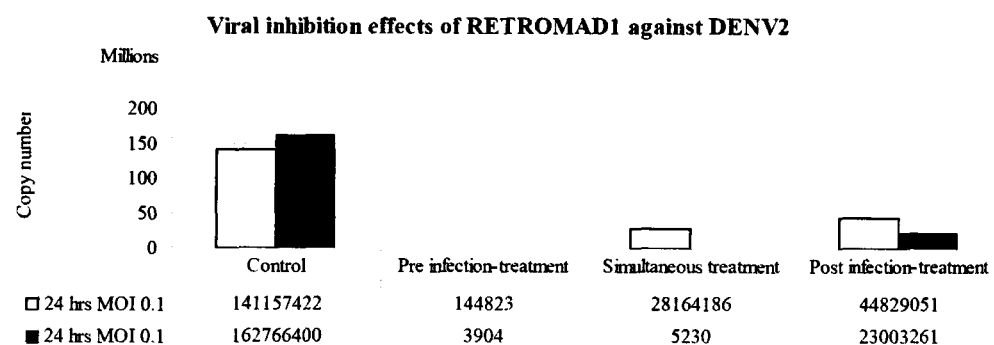
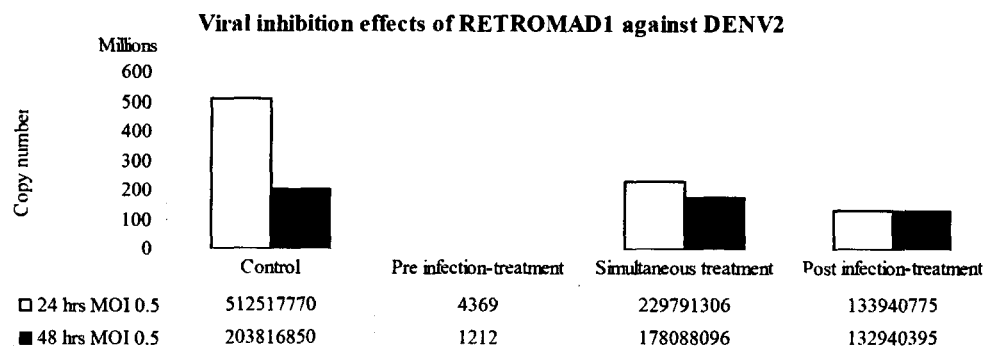
FIGURE 5 (continued)

(C)
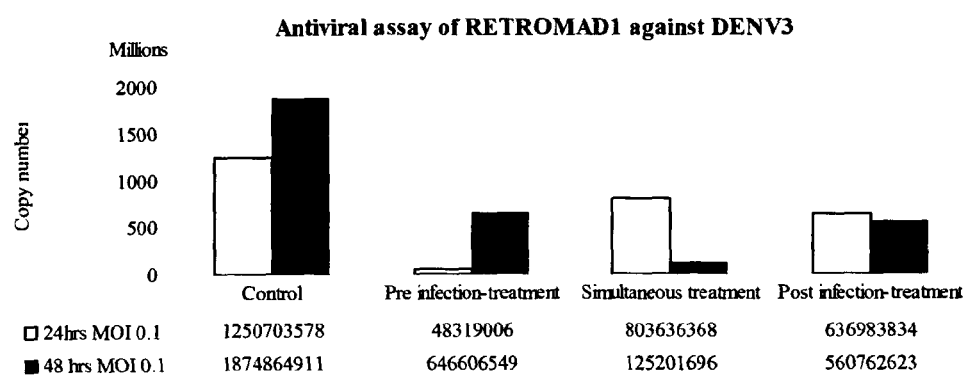
(D)
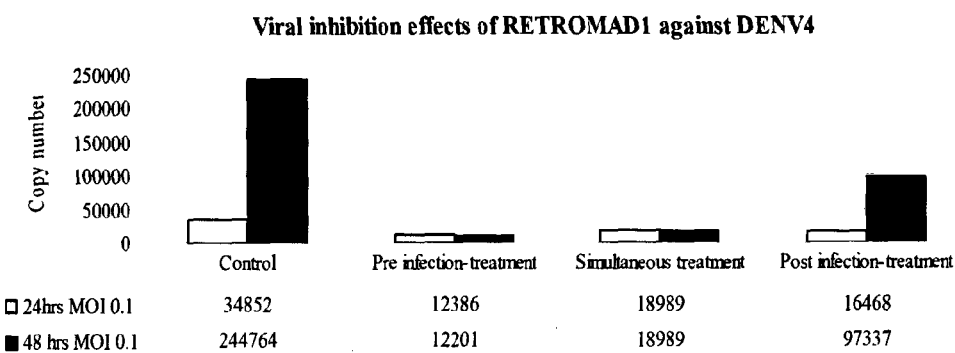
FIGURE 5

(A)
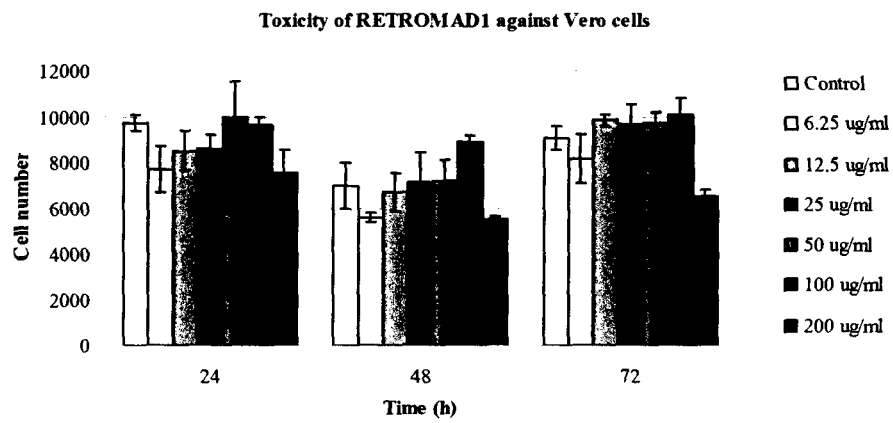
(B)
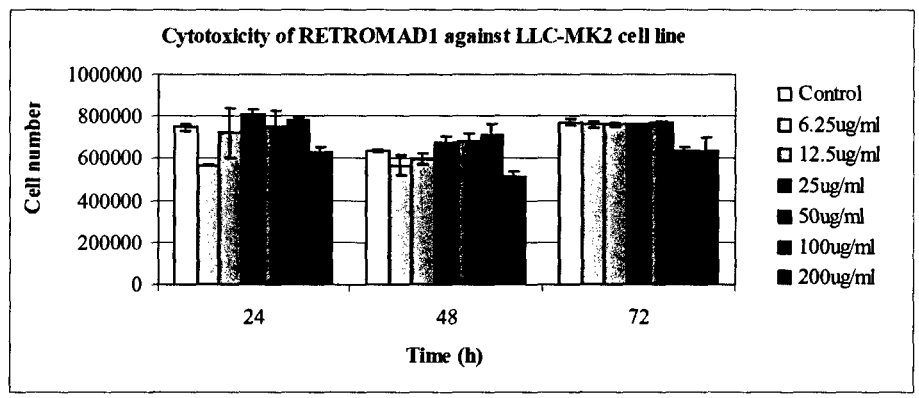
(C)
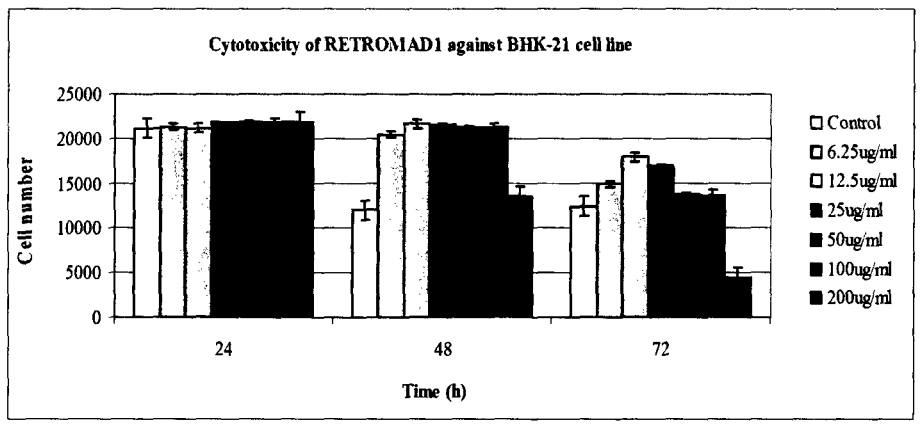
FIGURE 8

(A)
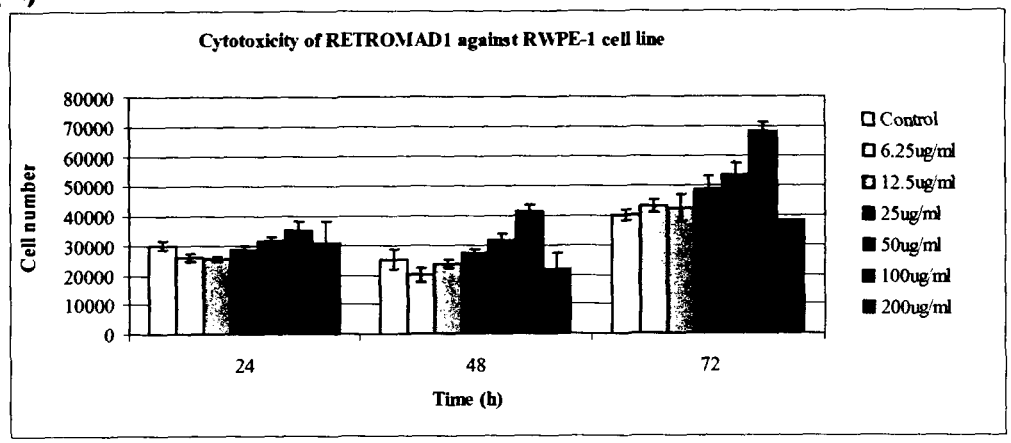
(B)
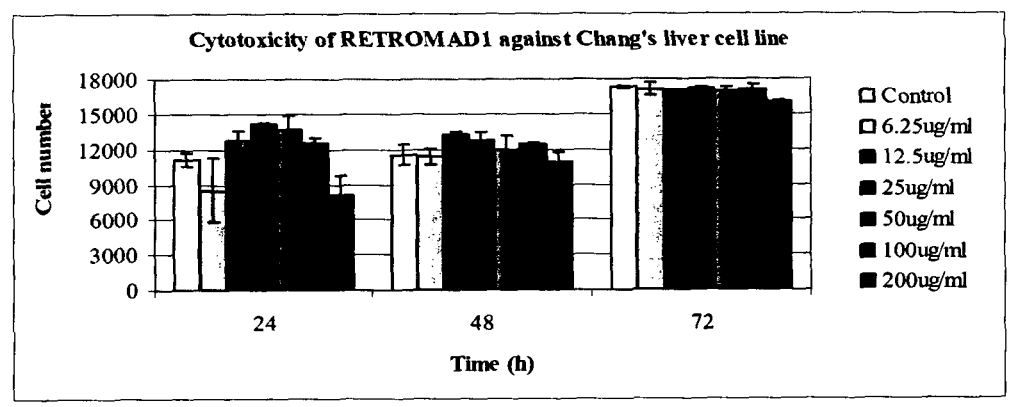
(C)
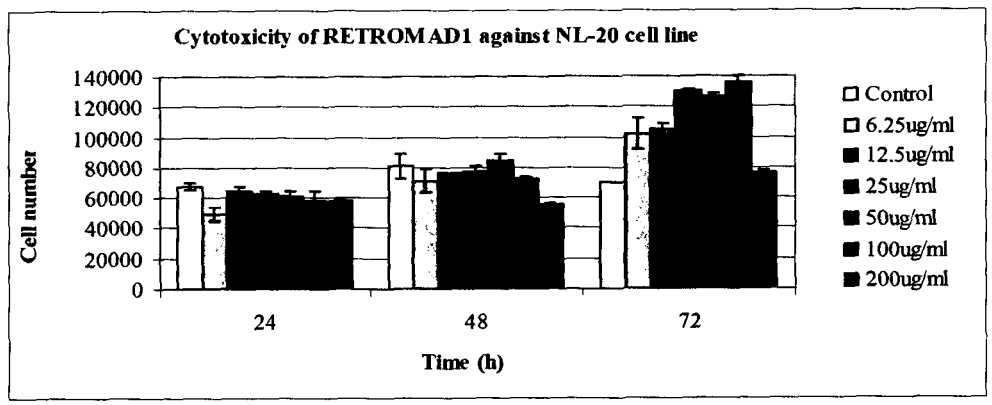
FIGURE 9 (continued)

(D)
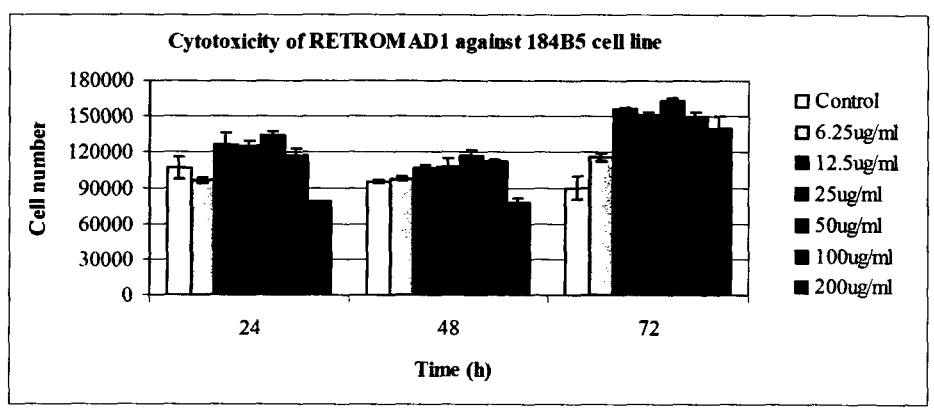
(E)
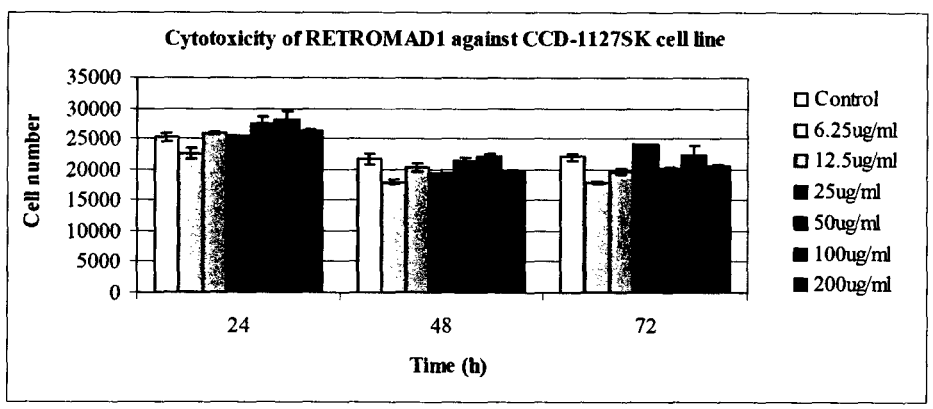
FIGURE 9

(A) 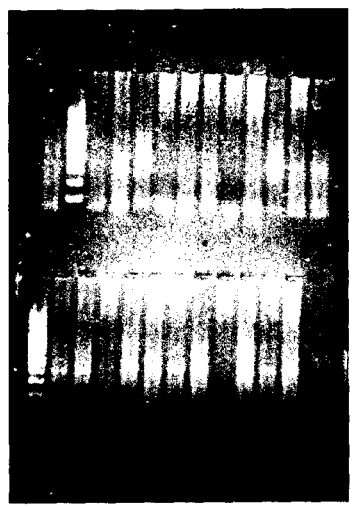  (B) 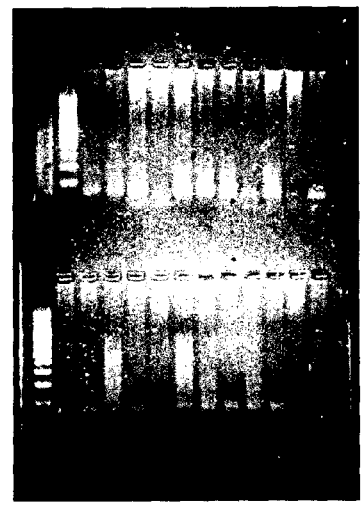
FIGURE 10
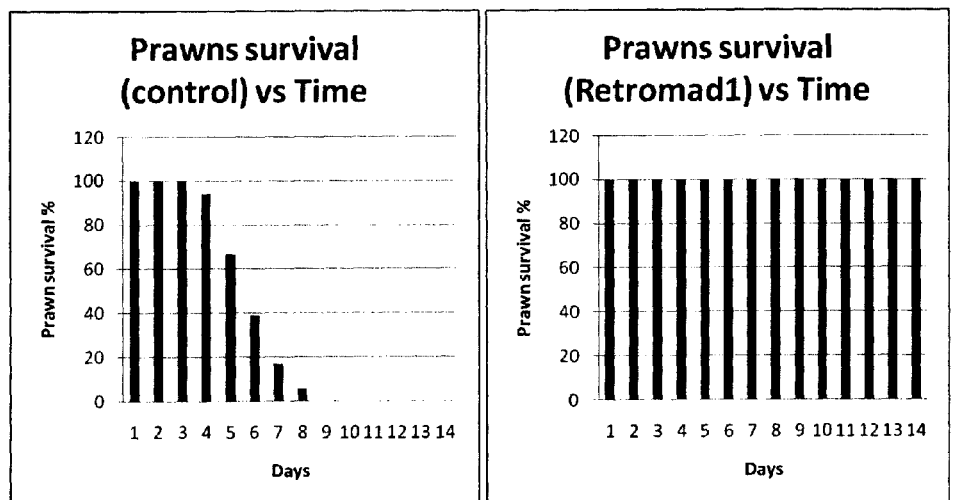
FIGURE 11

SEQUENCE LISTING

```
<160> NUMBER OF SEQ ID NOS: 34

<210> SEQ ID NO 1
<211> LENGTH: 379
<212> TYPE: PRT
<213> ORGANISM: Artificial Sequence
<220> FEATURE:
<223> OTHER INFORMATION: Fusion Peptide
<220> FEATURE:
<221> NAME/KEY: misc_feature
<223> OTHER INFORMATION: Amino acid sequence of fusion protein

<400> SEQUENCE: 1

Met Lys Tyr Leu Leu Pro Thr Ala Ala Ala Gly Leu Leu Leu Leu Ala
1               5                   10                  15

Ala Gln Pro Ala Met Ala Met Gly Arg Ile Cys Arg Cys Ile Cys Gly
            20                  25                  30

Arg Gly Ile Cys Arg Cys Ile Cys Gly Val Pro Gly Val Gly Val Pro
        35                  40                  45

Gly Val Gly Gly Ala Thr Gly Ser Asp Val Asn Phe Asp Leu Ser Thr
    50                  55                  60

Ala Thr Ala Lys Thr Tyr Thr Lys Phe Ile Glu Asp Phe Arg Ala Thr
65                  70                  75                  80

Leu Pro Phe Ser His Lys Val Tyr Asp Ile Pro Leu Leu Tyr Ser Thr
                85                  90                  95
```

```
Ile Ser Asp Ser Arg Arg Phe Ile Leu Leu Asp Leu Thr Ser Tyr Ala
            100                 105                 110
Tyr Glu Thr Ile Ser Val Ala Ile Asp Val Thr Asn Val Tyr Val Val
        115                 120                 125
Ala Tyr Arg Thr Arg Asp Val Ser Tyr Phe Phe Lys Glu Ser Pro Pro
    130                 135                 140
Glu Ala Tyr Asn Ile Leu Phe Lys Gly Thr Arg Lys Ile Thr Leu Pro
145                 150                 155                 160
Tyr Thr Gly Asn Tyr Glu Asn Leu Gln Thr Ala Ala His Lys Ile Arg
                165                 170                 175
Glu Asn Ile Asp Leu Gly Leu Pro Ala Leu Ser Ser Ala Ile Thr Thr
            180                 185                 190
Leu Phe Tyr Tyr Asn Ala Gln Ser Ala Pro Ser Ala Leu Leu Val Leu
        195                 200                 205
Ile Gln Thr Thr Ala Glu Ala Ala Arg Phe Lys Tyr Ile Glu Arg His
    210                 215                 220
Val Ala Lys Tyr Val Ala Thr Asn Phe Lys Pro Asn Leu Ala Ile Ile
225                 230                 235                 240
Ser Leu Glu Asn Gln Trp Ser Ala Leu Ser Lys Gln Ile Phe Leu Ala
                245                 250                 255
Gln Asn Gln Gly Gly Lys Phe Arg Asn Pro Val Asp Leu Ile Lys Pro
            260                 265                 270
Thr Gly Glu Arg Phe Gln Val Thr Asn Val Asp Ser Asp Val Val Lys
        275                 280                 285
Gly Asn Ile Lys Leu Leu Leu Asn Ser Arg Ala Ser Thr Ala Asp Glu
    290                 295                 300
Asn Phe Ile Thr Thr Met Thr Leu Leu Gly Glu Ser Val Val Glu Phe
305                 310                 315                 320
Pro Trp Ala Leu Trp Lys Thr Met Leu Lys Glu Leu Gly Thr Met Ala
                325                 330                 335
Leu His Ala Gly Lys Ala Ala Leu Gly Ala Ala Asp Thr Ile Ser
            340                 345                 350
Gln Gly Thr Gln Val Pro Gly Val Gly Val Pro Gly Val Gly Lys Leu
        355                 360                 365
Ala Ala Ala Leu Glu His His His His His His
    370                 375

<210> SEQ ID NO 2
<211> LENGTH: 1140
<212> TYPE: DNA
<213> ORGANISM: Artificial Sequence
<220> FEATURE:
<223> OTHER INFORMATION: Fusion peptide
<220> FEATURE:
<221> NAME/KEY: misc_feature
<223> OTHER INFORMATION: Polynucleotide sequence encoding fusion protein
      of SEQ ID No:1

<400> SEQUENCE: 2
atgaaatacc tgctgccgac cgctgctgct ggtctgctgc tcctcgctgc ccagccggcg      60
atggccatgg ggcgtatttg ccgttgcatt tgcggccgtg catttgccg ctgcatctgt      120 ggcgtgccgg tgttggtgt ccgggtgtg gtggtgcga ccggatccga tgtgaacttt        180
gatctgagca ccgcgaccgc gaaaacctat accaaattca tcgaagattt tcgtgcgacc     240
ctgccgttta gccataaagt gtatgatatc ccgctgctgt atagcaccat tagcgatagc     300 cgtcgttta ttctgctgga tctgaccagc tatgcgtatg aaaccattag cgtggcgatt      360
```

```
gatgtgacca acgtgtatgt ggtggcgtat cgtacccgtg atgtgagcta cttttttcaaa    420 gaaagcccgc cggaagcgta caacattctg tttaaaggca cccgtaaaat taccctgccg    480
tataccggca actatgaaaa cctgcagacc gcggcgcata aaattcgtga aacatcgat      540 ctgggcctgc cggccctgag cagcgcgatt accaccctgt tttattataa cgcgcagagc    600
gcgccgagcg cgctgctggt gctgattcag accaccgcgg aagcggcgcg ttttaaatat    660
attgaacgcc acgtggcgaa atatgtggcg accaacttta aaccgaacct ggccattatt    720
agcctggaaa accagtggag cgccctgagc aaacaaattt ttctggccca gaaccagggc    780
ggcaaatttc gtaatccggt ggatctgatt aaaccgaccg gcgaacgttt tcaggtgacc    840
aatgtggata gcgatgtggt gaaaggcaac attaaactgc tgctgaacag ccgtgcgagc    900
accgcggatg aaaactttat taccaccatg accctgctgg gcgaaagcgt ggtggaattc    960
ccgtgggcgc tgtggaaaac catgctgaaa gaactgggca cgatgcgct gcatgcgggt    1020 aaagcggcgc tgggtgcggc agcggatacc attagccagg gcacccaggt tccgggcgtg    1080
ggcgttccgg gcgttggtaa gcttgcggcc gcactcgagc accaccacca ccaccactga   1140

<210> SEQ ID NO 3
<211> LENGTH: 20
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<223> OTHER INFORMATION: Forward primer for HSV-1

<400> SEQUENCE: 3
tgggacacat gccttcttgg                                                  20

<210> SEQ ID NO 4
<211> LENGTH: 17
<212> TYPE: DNA
<213> ORGANISM: Artificial Sequence
<220> FEATURE:
<223> OTHER INFORMATION: primer sequence
<220> FEATURE:
<221> NAME/KEY: misc_feature
<223> OTHER INFORMATION: Forward primer for HSV-2

<400> SEQUENCE: 4
gtacagacct tcggagg                                                     17

<210> SEQ ID NO 5
<211> LENGTH: 28
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<223> OTHER INFORMATION: Reverse primer of HSV-2
<220> FEATURE:
<221> NAME/KEY: misc_feature
<223> OTHER INFORMATION: Reverse primer of HSV-1
<220> FEATURE:
<221> NAME/KEY: misc_feature
<223> OTHER INFORMATION: Reverse primer for HSV-2

<400> SEQUENCE: 5
acccttagtc agactctgtt acttaccc                                         28
```

```
<210> SEQ ID NO 6
<211> LENGTH: 15
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<223> OTHER INFORMATION: Reverse primer for HSV-2

<400> SEQUENCE: 6
cgcttcatca tgggc                                                          15

<210> SEQ ID NO 7
<211> LENGTH: 20
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<223> OTHER INFORMATION: Forward primer for DENV1, DENV2, DENV3 and
      DENV4

<400> SEQUENCE: 7
ggaaggagaa ggactgcaca                                                     20

<210> SEQ ID NO 8
<211> LENGTH: 21
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<223> OTHER INFORMATION: Reverse primer for DENV1, DENV2, DENV3 and
      DENV4

<400> SEQUENCE: 8
attcttgtgt cccatcctgc t                                                   21

<210> SEQ ID NO 9
<211> LENGTH: 20
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<223> OTHER INFORMATION: Forward primer for HPV

<400> SEQUENCE: 9
acactcagcc tctaccttgt                                                     20

<210> SEQ ID NO 10
<211> LENGTH: 20
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<223> OTHER INFORMATION: Reverse primer for HPV

<400> SEQUENCE: 10
gcattacaag agccaagcag                                                     20
```

```
<210> SEQ ID NO 11
<211> LENGTH: 5
<212> TYPE: PRT
<213> ORGANISM: Artificial Sequence
<220> FEATURE:
<223> OTHER INFORMATION: Linker peptide
<220> FEATURE:
<221> NAME/KEY: misc_feature
<223> OTHER INFORMATION: N is 0, 1, 2, 3, 4 or 5
<220> FEATURE:
<221> NAME/KEY: misc_feature
<223> OTHER INFORMATION: Linker Peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 11

Val Pro Xaa Val Gly
1               5

<210> SEQ ID NO 12
<211> LENGTH: 18
<212> TYPE: PRT
<213> ORGANISM: Artificial Sequence
<220> FEATURE:
<223> OTHER INFORMATION: Polypeptide A
<220> FEATURE:
<221> NAME/KEY: misc_feature
<223> OTHER INFORMATION: Amino acid Sequence of Polypeptide A

<400> SEQUENCE: 12

Gly Arg Ile Cys Arg Cys Ile Cys Gly Arg Gly Ile Cys Arg Cys Ile
1               5                   10                  15

Cys Gly

<210> SEQ ID NO 13
<211> LENGTH: 268
<212> TYPE: PRT
<213> ORGANISM: Artificial Sequence
<220> FEATURE:
<223> OTHER INFORMATION: Polypeptide B
<220> FEATURE:
<221> NAME/KEY: misc_feature
<223> OTHER INFORMATION: Amino acid Sequence of Polypeptide B

<400> SEQUENCE: 13

Gly Ser Asp Val Asn Phe Asp Leu Ser Thr Ala Thr Ala Lys Thr Tyr
1               5                   10                  15

Thr Lys Phe Ile Glu Asp Phe Arg Ala Thr Leu Pro Phe Ser His Lys
            20                  25                  30

Val Tyr Asp Ile Pro Leu Leu Tyr Ser Thr Ile Ser Asp Ser Arg Arg
        35                  40                  45

Phe Ile Leu Leu Asp Leu Thr Ser Tyr Ala Tyr Glu Thr Ile Ser Val
    50                  55                  60

Ala Ile Asp Val Thr Asn Val Tyr Val Val Ala Tyr Arg Thr Arg Asp
65                  70                  75                  80

Val Ser Tyr Phe Phe Lys Glu Ser Pro Pro Glu Ala Tyr Asn Ile Leu
            85                  90                  95

Phe Lys Gly Thr Arg Lys Ile Thr Leu Pro Tyr Thr Gly Asn Tyr Glu
        100                 105                 110

Asn Leu Gln Thr Ala Ala His Lys Ile Arg Glu Asn Ile Asp Leu Gly
    115                 120                 125

Leu Pro Ala Leu Ser Ser Ala Ile Thr Thr Leu Phe Tyr Tyr Asn Ala
    130                 135                 140
```

```
Gln Ser Ala Pro Ser Ala Leu Leu Val Leu Ile Gln Thr Thr Ala Glu
145                 150                 155                 160

Ala Ala Arg Phe Lys Tyr Ile Glu Arg His Val Ala Lys Tyr Val Ala
                165                 170                 175

Thr Asn Phe Lys Pro Asn Leu Ala Ile Ile Ser Leu Glu Asn Gln Trp
            180                 185                 190

Ser Ala Leu Ser Lys Gln Ile Phe Leu Ala Gln Asn Gln Gly Gly Lys
        195                 200                 205

Phe Arg Asn Pro Val Asp Leu Ile Lys Pro Thr Gly Glu Arg Phe Gln
210                 215                 220

Val Thr Asn Val Asp Ser Asp Val Val Lys Gly Asn Ile Lys Leu Leu
225                 230                 235                 240

Leu Asn Ser Arg Ala Ser Thr Ala Asp Glu Asn Phe Ile Thr Thr Met
                245                 250                 255

Thr Leu Leu Gly Glu Ser Val Val Glu Phe Pro Trp
            260                 265

<210> SEQ ID NO 14
<211> LENGTH: 34
<212> TYPE: PRT
<213> ORGANISM: Artificial Sequence
<220> FEATURE:
<223> OTHER INFORMATION: Polypeptide C
<220> FEATURE:
<221> NAME/KEY: misc_feature
<223> OTHER INFORMATION: Amino acid Sequence of Polypeptide C

<400> SEQUENCE: 14

Ala Leu Trp Lys Thr Met Leu Lys Glu Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 15
<211> LENGTH: 18
<212> TYPE: PRT
<213> ORGANISM: artificial sequence
<220> FEATURE:
<223> OTHER INFORMATION: theta Defensin
<220> FEATURE:
<221> NAME/KEY: misc_feature
<223> OTHER INFORMATION: Rhesus minidefensin (RTD-1)

<400> SEQUENCE: 15

Gly Phe Cys Arg Cys Leu Cys Arg Arg Gly Val Cys Arg Cys Ile Cys
1               5                   10                  15

Thr Arg

<210> SEQ ID NO 16
<211> LENGTH: 18
<212> TYPE: PRT
<213> ORGANISM: artificial sequence
<220> FEATURE:
<223> OTHER INFORMATION: theta Defensin
<220> FEATURE:
<221> NAME/KEY: misc_feature
<223> OTHER INFORMATION: RTD-2
```

-continued

<400> SEQUENCE: 16

Arg Cys Leu Cys Arg Arg Gly Val Cys Arg Cys Leu Cys Arg Arg Gly
1               5                   10                  15

Val Cys

<210> SEQ ID NO 17
<211> LENGTH: 18
<212> TYPE: PRT
<213> ORGANISM: artificial sequence
<220> FEATURE:
<223> OTHER INFORMATION: theta Defensin
<220> FEATURE:
<221> NAME/KEY: misc_feature
<223> OTHER INFORMATION: RTD-3

<400> SEQUENCE: 17

Arg Cys Ile Cys Thr Arg Gly Phe Cys Arg Cys Ile Cys Thr Arg Gly
1               5                   10                  15

Phe Cys

<210> SEQ ID NO 18
<211> LENGTH: 18
<212> TYPE: PRT
<213> ORGANISM: artificial sequence
<220> FEATURE:
<223> OTHER INFORMATION: theta Defensin
<220> FEATURE:
<221> NAME/KEY: misc_feature
<223> OTHER INFORMATION: Retrocyclin-1

<400> SEQUENCE: 18

Gly Ile Cys Arg Cys Ile Cys Gly Arg Gly Ile Cys Arg Cys Ile Cys
1               5                   10                  15

Gly Arg

<210> SEQ ID NO 19
<211> LENGTH: 18
<212> TYPE: PRT
<213> ORGANISM: artificial sequence
<220> FEATURE:
<223> OTHER INFORMATION: theta Defensin
<220> FEATURE:
<221> NAME/KEY: misc_feature
<223> OTHER INFORMATION: Retrocyclin-2

<400> SEQUENCE: 19

Gly Ile Cys Arg Cys Ile Cys Gly Arg Gly Ile Cys Arg Cys Ile Cys
1               5                   10                  15

Gly Arg

<210> SEQ ID NO 20
<211> LENGTH: 18
<212> TYPE: PRT
<213> ORGANISM: artificial sequence
<220> FEATURE:
<223> OTHER INFORMATION: theta Defensin
<220> FEATURE:
<221> NAME/KEY: misc_feature
<223> OTHER INFORMATION: Retrocyclin-3

<400> SEQUENCE: 20

Arg Ile Cys Arg Cys Ile Cys Gly Arg Arg Ile Cys Arg Cys Ile Cys
1               5                   10                  15

Gly Arg

```
<210> SEQ ID NO 21
<211> LENGTH: 18
<212> TYPE: PRT
<213> ORGANISM: artificial sequence
<220> FEATURE:
<223> OTHER INFORMATION: synthetic theta Defensin
<220> FEATURE:
<221> NAME/KEY: misc_feature
<223> OTHER INFORMATION: RC100

<400> SEQUENCE: 21

Gly Ile Cys Arg Cys Ile Cys Gly Arg Gly Ile Cys Arg Cys Ile Cys
1               5                   10                  15

Gly Arg

<210> SEQ ID NO 22
<211> LENGTH: 18
<212> TYPE: PRT
<213> ORGANISM: artificial sequence
<220> FEATURE:
<223> OTHER INFORMATION: synthetic theta Defensin
<220> FEATURE:
<221> NAME/KEY: misc_feature
<223> OTHER INFORMATION: RC101

<400> SEQUENCE: 22

Gly Ile Cys Arg Cys Ile Cys Gly Lys Gly Ile Cys Arg Cys Ile Cys
1               5                   10                  15

Gly Arg

<210> SEQ ID NO 23
<211> LENGTH: 18
<212> TYPE: PRT
<213> ORGANISM: artificial sequence
<220> FEATURE:
<223> OTHER INFORMATION: synthetic theta Defensin
<220> FEATURE:
<221> NAME/KEY: misc_feature
<223> OTHER INFORMATION: RC102

<400> SEQUENCE: 23

Gly Ile Cys Arg Cys Tyr Cys Gly Arg Gly Ile Cys Arg Cys Ile Cys
1               5                   10                  15

Gly Arg

<210> SEQ ID NO 24
<211> LENGTH: 18
<212> TYPE: PRT
<213> ORGANISM: artificial sequence
<220> FEATURE:
<223> OTHER INFORMATION: synthetic theta Defensin
<220> FEATURE:
<221> NAME/KEY: misc_feature
<223> OTHER INFORMATION: RC103

<400> SEQUENCE: 24

Gly Ile Cys Arg Cys Ile Cys Gly Arg Gly Ile Cys Arg Cys Tyr Cys
1               5                   10                  15

Gly Arg

<210> SEQ ID NO 25
<211> LENGTH: 18
<212> TYPE: PRT
<213> ORGANISM: artificial sequence
<220> FEATURE:
<223> OTHER INFORMATION: synthetic theta Defensin
```

```
<220> FEATURE:
<221> NAME/KEY: misc_feature
<223> OTHER INFORMATION: RC104

<400> SEQUENCE: 25

Gly Tyr Cys Arg Cys Ile Cys Gly Arg Gly Ile Cys Arg Cys Ile Cys
1               5                   10                  15

Gly Arg

<210> SEQ ID NO 26
<211> LENGTH: 18
<212> TYPE: PRT
<213> ORGANISM: artificial sequence
<220> FEATURE:
<223> OTHER INFORMATION: synthetic theta Defensin
<220> FEATURE:
<221> NAME/KEY: misc_feature
<223> OTHER INFORMATION: RC105

<400> SEQUENCE: 26

Gly Ile Cys Arg Cys Ile Cys Gly Arg Gly Tyr Cys Arg Cys Ile Cys
1               5                   10                  15

Gly Arg

<210> SEQ ID NO 27
<211> LENGTH: 18
<212> TYPE: PRT
<213> ORGANISM: artificial sequence
<220> FEATURE:
<223> OTHER INFORMATION: synthetic theta Defensin
<220> FEATURE:
<221> NAME/KEY: misc_feature
<223> OTHER INFORMATION: RC106

<400> SEQUENCE: 27

Gly Ile Cys Tyr Cys Ile Cys Gly Arg Gly Ile Cys Arg Cys Ile Cys
1               5                   10                  15

Gly Arg

<210> SEQ ID NO 28
<211> LENGTH: 18
<212> TYPE: PRT
<213> ORGANISM: artificial sequence
<220> FEATURE:
<223> OTHER INFORMATION: synthetic theta Defensin
<220> FEATURE:
<221> NAME/KEY: misc_feature
<223> OTHER INFORMATION: RC107

<400> SEQUENCE: 28

Gly Ile Cys Ile Cys Ile Cys Gly Tyr Gly Ile Cys Arg Cys Ile Cys
1               5                   10                  15

Gly Arg

<210> SEQ ID NO 29
<211> LENGTH: 18
<212> TYPE: PRT
<213> ORGANISM: artificial sequence
<220> FEATURE:
<223> OTHER INFORMATION: synthetic theta Defensin
<220> FEATURE:
<221> NAME/KEY: misc_feature
<223> OTHER INFORMATION: RC108
```

```
<400> SEQUENCE: 29

Gly Ile Cys Ile Cys Ile Cys Gly Arg Gly Ile Cys Tyr Cys Ile Cys
1               5                   10                  15

Gly Arg

<210> SEQ ID NO 30
<211> LENGTH: 18
<212> TYPE: PRT
<213> ORGANISM: artificial sequence
<220> FEATURE:
<223> OTHER INFORMATION: synthetic theta Defensin
<220> FEATURE:
<221> NAME/KEY: misc_feature
<223> OTHER INFORMATION: RC110

<400> SEQUENCE: 30

Gly Ile Cys Ile Cys Ile Cys Gly Arg Gly Ile Cys Tyr Cys Ile Cys
1               5                   10                  15

Gly Arg

<210> SEQ ID NO 31
<211> LENGTH: 18
<212> TYPE: PRT
<213> ORGANISM: artificial sequence
<220> FEATURE:
<223> OTHER INFORMATION: synthetic theta Defensin
<220> FEATURE:
<221> NAME/KEY: misc_feature
<223> OTHER INFORMATION: RC111

<400> SEQUENCE: 31

Arg Gly Cys Ile Cys Arg Cys Ile Gly Arg Gly Cys Ile Cys Arg Cys
1               5                   10                  15

Ile Gly

<210> SEQ ID NO 32
<211> LENGTH: 18
<212> TYPE: PRT
<213> ORGANISM: artificial sequence
<220> FEATURE:
<223> OTHER INFORMATION: synthetic theta Defensin
<220> FEATURE:
<221> NAME/KEY: misc_feature
<223> OTHER INFORMATION: RC112

<400> SEQUENCE: 32

Arg Gly Cys Ile Cys Arg Cys Ile Gly Arg Gly Cys Ile Cys Arg Cys
1               5                   10                  15

Ile Gly

<210> SEQ ID NO 33
<211> LENGTH: 18
<212> TYPE: PRT
<213> ORGANISM: artificial sequence
<220> FEATURE:
<223> OTHER INFORMATION: synthetic theta Defensin
<220> FEATURE:
<221> NAME/KEY: misc_feature
<223> OTHER INFORMATION: RC113

<400> SEQUENCE: 33

Gly Ile Cys Arg Cys Ile Cys Gly Arg Gly Ile Cys Arg Cys Ile Cys
1               5                   10                  15

Gly Arg
```

-continued

```
<210> SEQ ID NO 34
<211> LENGTH: 18
<212> TYPE: PRT
<213> ORGANISM: artificial sequence
<220> FEATURE:
<223> OTHER INFORMATION: synthetic theta Defensin
<220> FEATURE:
<221> NAME/KEY: misc_feature
<223> OTHER INFORMATION: RC114

<400> SEQUENCE: 34

Gly Ile Cys Arg Cys Ile Cys Gly Lys Gly Ile Cys Arg Cys Tyr Cys
1               5                   10                  15

Gly Arg
```

US 9,155,800 B2

ANTIMICROBIAL FUSION COMPOUNDS AND USES THEREOF

RELATED APPLICATIONS

This application is a 35 U.S.C. §371 filing of International Application No. PCT/MY2012/000003, filed Jan. 9, 2012, which claims priority to Malaysian Patent Application No. PI2011000092, filed on Jan. 7, 2011. The entire contents of each of these documents are incorporated herein by reference in their entireties.

FIELD OF THE INVENTION

The present invention relates to antimicrobial fusion compounds, in particular polypeptides, and fragments thereof and to their use as therapeutic agents in microbial infections.

BACKGROUND TO THE INVENTION

Microbial infections affect human beings and animals and cause a high level of morbidity around the world. Microbial infectious agents include protozoan parasites, bacteria and fungi for which antimicrobial agents are often available. However, some antimicrobial agents are associated with undesirable side effects and the problem of microbial resistance to such agents is a growing problem.

Microbial infectious agents also include viruses which are the cause of many widespread infectious diseases afflicting mankind as well as mankind's companion animals and also animals farmed specifically for human food. Most of the presently available antiviral drugs used in human therapeutic applications are mono-functional in nature and block only one specific viral pathway such as for example, entry of the virus into the host cell, fusion or integration of the viral genome into the host cell genome, translation or reverse transcription of the viral ssRNA to dsDNA format that is viable for integration into the infected host-cell genome. Accordingly, once a virus acquires resistance to the mono-functional antiviral drug, the drug loses its effectiveness.

Also, at present no therapeutics are available for a number of animal viruses including for example White Spot Syndrome Virus (WSSV), Porcine Epidemic Diarrhoea Virus (PEDV), Porcine Reproductive & Respiratory Syndrome Virus (PRRSV) and the like. These animal viruses are known to particularly affect the prawn and swine industries. The annual loss caused by each of these viruses is believed to be in excess of USD 1 billion.

Effective vaccines for these viruses and most other viruses are difficult to develop due to their high mutation rate. Also, vaccines that work for one geographical strain often do not work well for other geographical strains of the same virus.

Examples of antiviral drugs include Enfuvirtide (marketed by Roche under the trade name FUZEON®) which is a HIV-1 fusion inhibitor. Enfuvirtide is a modified protein which is produced by synthesis and is known to be an expensive mode of treatment which is reported to be in the region of USD25,000 per year per person. Its mode of administration is also very inconvenient as it is introduced into the body by subcutaneous injection twice daily.

Another example of antiviral drug includes Oseltamivir (also known with its trade name TAMIFLU®) which slows the spread of influenza (flu) virus between cells in the body by stopping the virus from chemically cutting ties with its host cell. TAMIFLU® has been used to treat and prevent Influenza virus A and Influenza virus B infection in over 50 million people since 1999 and is taken orally in capsules or as a suspension. However, there are now many strains of Influenza virus A and Influenza virus B which are resistant to TAMIFLU®. Zanamivir (also known by its trade name RELENZA®), another antiviral drug acting as a neuraminidase inhibitor used in the treatment and prophylaxis of Influenza virus A and Influenza virus B. RELENZA® is administered by inhalation. It is well known in the art that the antiviral drugs TAMIFLU® and RELENZA® depend on raw material shikimic acid for production which cannot be economically synthesized. In fact, ROCHE has made several press releases before that production volume of antiviral drugs TAMIFLU® and RELENZA® may be seriously limited by the supply of shikimic acid.

SUMMARY OF THE INVENTION

The present invention is defined in the appended independent claims. Some optional features of the present invention are defined in the appended dependent claims.

According to one aspect of the present invention, there is provided a fusion protein comprising at least one Type 1 Ribosome Inactivating Protein or a fragment thereof, polypeptide B; and
  (i) at least one polypeptide A capable of viral entry inhibition; and/or
  (ii) at least one Cationic AntiMicrobial Peptide, or a fragment thereof, polypeptide C.

The polypeptide A may be theta defensin, an analogue, or a fragment thereof.

In particular, the fusion protein according to any aspect of the present invention may be suitable for oral administration.

According to another aspect of the present invention, there is provided a pharmaceutical composition comprising a fusion protein according to any aspect of the present invention.

According to a further aspect of the present invention, there is provided a method of treating and/or preventing a microbial infection in a vertebrate, invertebrate or plant in need thereof, comprising a step of administering to the vertebrate, invertebrate or plant an effective amount of the fusion protein or pharmaceutical composition according to any aspect of the present invention. In particular, the microbial infection may be a viral infection. The vertebrate may be a mammal, fish or bird. Even more in particular, the mammal may be a non-human animal.

As will be apparent from the following description, preferred embodiments of the present invention allow for a fusion protein with an optimal effectiveness with a broad spectrum therapy and/or allowing oral delivery of the protein as some of the several applications.

BRIEF DESCRIPTION OF THE FIGURES

Preferred embodiments of the fusion protein will now be described by way of example with reference to the accompanying figures in which:

FIG. 1 is a translation map of RetroMAD1 (SEQ ID NO:1 and SEQ ID NO:2).

FIG. 2 is a graph showing A) Time course expression and B) Solubility of RetroMAD1 expression in *E. Coli* BL21 (DE3) cells. Cells harbouring pRMD were harvested before induction (0 h), and after induction for 1 h, 2 h and 3 h represents the pellet phase, the hours with asterisk (*) represents the supernatant phase. Proteins were analysed on a 15% SDS-PAGE. M: PageRuler™ Protein Ladder Fermentas, U: uninduced, IND: induced and IB: purified inclusion bodies. Arrow indicates *E. coli* produced RetroMAD1 (41.2 kDa)

FIG. 3 is a graph showing the amount of viral copies reduced in each treatment over an incubation period of 24- and 48-hours with RetroMAD1: (A) HSV-1 at MOI=0.1, (B) HSV-1 at MOI=0.5

FIG. 4 is a graph showing the amount of viral copies reduced in each treatment over an incubation period of 24- and 48-hours with RetroMAD1: (A) HSV-2 at MOI=0.1, (B) HSV-1 at MOI=0.5

FIG. 5 is a graph showing the amount of viral copies reduced during each treatment over a period of 24- and 48-hours incubation with RetroMAD1: (A) DENV1, (B) DENV2 at MOI 0.1, and DENV2 at MOI 0.5, (C) DENV3 and (D) DENV4

FIG. 8 is a graph showing cytotoxicity of RetroMAD1 measured at end-point of 24 hours, 48 hours and 96 hours. All values are presented as means±standard deviation of three replicates the experiment. The maximum non-toxic dose of the mammalian cell lines: (A) Vero, (B) LLC-MK2 and (C) BHK-21 cell line was 100 µg/ml.

FIG. 9 is a graph showing cytotoxicity of RetroMAD1 measured at end-point of 24 hours, 48 hours and 96 hours. All values are presented as means±standard deviation of three replicates the experiment. The maximum non-toxic dose of the human cell lines: (A) RWPE-1, (B) Chang's liver, (C) NL-20, (D) 184B5 and (E) CCD-1127SK cell line was 100 µg/ml.

FIG. 10(A) shows a picture of a gel where the bands with a size of 441 bp show control individual prawns infected with HPV. 22/23 were positive for HPV.

FIG. 10B shows a picture of a gel where only 2/24 of the treated individual prawns were infected with HPV. 22/24 of the individual prawns were negative for HPV.

FIG. 11 is a graph showing the percentage of survival of prawns experimentally infected with WSSV, on the left is control while on the right is the treated.

DETAILED DESCRIPTION OF THE INVENTION

Definitions

Figure 6:
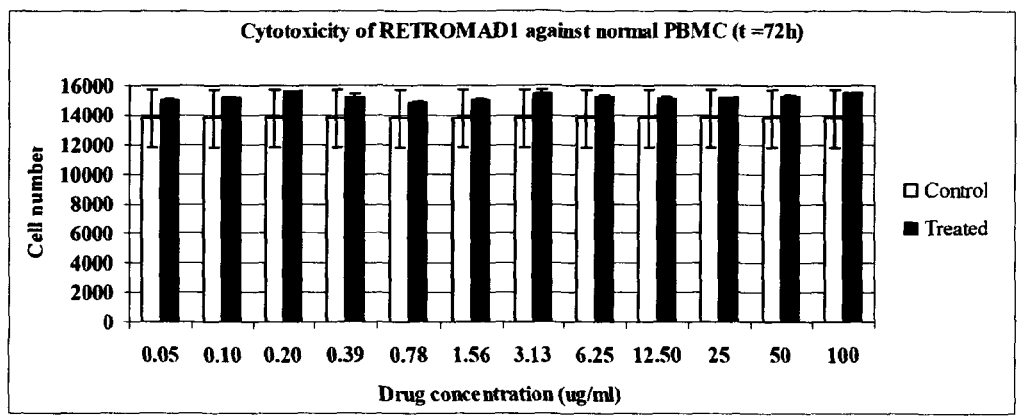
FIG. 6 is a graph showing the cell number of simultaneously treated normal PBMC at post-72 hours incubation with RetroMAD1.

For convenience, certain terms employed in the specification, examples and appended claims are collected here.

The term "adjuvant", as used in the context of the invention refers to an immunological adjuvant. By this, an adjuvant is meant to be a compound that is able to enhance or facilitate the immune system's response to the ingredient in question, thereby inducing an immune response or series of immune responses in the subject. The adjuvant can facilitate the effect of the therapeutic composition by forming depots (prolonging the half-life of the ingredient), provide additional T-cell help and stimulate cytokine production. Facilitation of antigen survival and unspecific stimulation by adjuvants may, in some cases, be required if the antigenic molecule are only weakly antigenic or only exerts weak to moderate interactions with compounds, molecules, or cells of the immune system.

The term "analogue" as used in the context of the invention refers to a peptide that may be modified by varying the amino acid sequence to comprise one or more naturally-occurring and/or non-naturally-occurring amino acids, provided that the peptide analogue is capable of reducing or preventing growth of a microorganism or killing a microorganism. For example, the term "analogue" encompasses an inhibitory peptide comprising one or more conservative amino acid changes. The term "analogue" also encompasses a peptide comprising, for example, one or more D-amino acids. Such an analogue has the characteristic of, for example, protease resistance. Analogues also include peptidomimetics, e.g., in which one or more peptide bonds have been modified. Preferred analogues include an analogues of a peptide as described according to any embodiment here comprising one or more non-naturally-occurring amino acid analogues.

The term "antimicrobial", as used in the context of the invention refers to the biological activity of the peptide or analogue or derivative thereof of the present invention, and means that the proteins of the present invention have the capacity to kill, disrupt reproduction or otherwise disable microbial growth. The peptide or analogue or derivative thereof of the present invention is capable of killing a microorganism and/or reducing or preventing growth of a microorganism. i.e., the peptide has microbicidal activity and/or microbiostatic activity. The peptide may be a drug, compound or molecule, including the fused protein according to any embodiment of the present invention for use in treating or preventing microbial infection. Methods for determining the antimicrobial activity of a peptide or analogue or derivative thereof will be apparent to a skilled person and/or described herein. For example, the peptide or analogue or derivative is applied to a substrate upon which a microorganism has been previously grown and, after a suitable period of time, the level of growth inhibition and/or cell death of the microorganism is determined.

The term "comprising" as used in the context of the invention refers to where the various components, ingredients, or steps, can be conjointly employed in practicing the present invention. Accordingly, the term "comprising" encompasses the more restrictive terms "consisting essentially of" and "consisting of." With the term "consisting essentially of" it is understood that the epitope/antigen of the present invention "substantially" comprises the indicated sequence as "essential" element. Additional sequences may be included at the 5' end and/or at the 3' end. Accordingly, a polypeptide "consisting essentially of" sequence X will be novel in view of a known polypeptide accidentally comprising the sequence X. With the term "consisting of" it is understood that the polypeptide, polynucleotide and/or antigen according to the invention corresponds to at least one of the indicated sequence (for example a specific sequence indicated with a SEQ ID Number or a homologous sequence or fragment thereof).

The term "derivative" as used in the context of the invention includes e.g., a fragment or processed form of the stated peptide, a variant or mutant comprising one or more amino acid substitutions, deletions of additions relative to the stated peptide, a fusion protein comprising the stated peptide or a peptide comprising one or more additional non-peptide components relative to the stated peptide e.g., a chemical component, e.g., polyethylene glycol (PEG). The term "derivative" also encompasses polypeptides comprising the fusion protein according to the invention. For example, the polypeptide comprises a label, such as, for example, an epitope, e.g., a FLAG epitope or a V5 epitope or an HA epitope. For example, the epitope is a FLAG epitope. Such a tag is useful for, for example, purifying the polypeptide. A preferred derivative of an antimicrobial fusion protein of the invention has enhanced stability. For example, a cleavage site of a protease active in a subject to which a fusion protein is to be administered is mutated and/or deleted to produce a stable derivative of an antimicrobial fusion protein of the invention. The term "derivative" also encompasses a derivatized peptide, such as, for example, a peptide modified to contain one or more chemical moieties other than an amino acid. The chemical moiety may be linked covalently to the peptide e.g., via an amino terminal amino acid residue, a carboxy terminal amino acid residue, or at an internal amino acid residue. Such modifications include the addition of a protective or capping group on a reactive moiety in the peptide, addition of a detectable label, and other changes that do not adversely destroy the activity of the peptide compound.

Accordingly, acceptable amino acid substitutions are generally therefore based on the relative similarity of the amino acid side-chain substituents, for example, their hydrophobicity, hydrophilicity, charge, size, and the like. Exemplary substitutions which take several of the foregoing characteristics into consideration are well known to those of skill in the art and include: arginine and lysine; glutamate and aspartate; serine and threonine; glutamine and asparagine; and valine, leucine and isoleucine. The isolated peptides of the present invention can be prepared in a number of suitable ways known in the art including typical chemical synthesis processes to prepare a sequence of polypeptides.

The term "fragment" as used in the context of the invention refers to an incomplete or isolated portion of the full sequence of the fusion protein according to any aspect of the present invention which comprises the active site(s) that confers the sequence with the characteristics and function of the protein. In particular, it may be shorter by at least one amino acid. For example a fragment of the fusion protein according to the present invention comprises the active site(s) that enable the protein to recognise a microorganism. The fragment may at least be 10 amino acids in length. For example, a non-limiting fragment of RIP may at least comprise the core or the bioactive site of the RIP which may be approximately 5 kDa in size.

The term "fusion protein(s)" as used in the context of the invention refers to proteins created through the joining of two or more genes, which originally coded for separate proteins. Translation of this fusion gene results in a single polypeptide with functional properties derived from each of the original proteins. Recombinant fusion proteins are created artificially by recombinant DNA technology for use in biological research or therapeutics. For example, the fusion protein according to any aspect of the present invention may comprise a Type 1 RIP, polypeptide B; and a polypeptide A capable of viral entry inhibition and/or a CAP, polypeptide C. The structure of the fusion protein may be A-B-C, A-C-B, C-A-B, C-B-A, B-A-C, B-C-A, A-B-C-C, A-B, B-C, B-C-C or C-C-B-C-C. In particular, the fusion protein may comprise dimers and/or tandem repeats. More in particular, the structure of the fusion protein according to any aspect of the present invention may be repeats of the structure mentioned above. For example, the structure may be A-A-B-C-C, C-C-B-C-C, A-A-B-A-A and the like. The polypeptide A, B or C in each fusion protein may be the same protein or may be a different protein when repeated. Polypeptide A may be theta defensin, an analogue, or a fragment thereof. A fusion protein according to the present invention may comprise the sequence of SEQ ID NO:1, a variant, derivative or fragment thereof. The term "RetroMAD1" is used in the present invention to refer to a fusion protein with the structure A-B-C and with amino acid sequence SEQ ID NO:1. In particular, in RetroMAD1 polypeptide A may be Retrocyclin 101, polypeptide B may be MAP30 and polypeptide C may be Dermaseptin 1. These peptides may be directly fused to one another or connected to one another by a linker peptide.

The term "linker peptide", as used in the context of the invention is used interchangeably with the term "linker" herein. A linker peptide is a peptide that covalently or non-covalently connects two or more molecules or peptides, thereby creating a larger complex consisting of all molecules or peptides including the linker peptide. A non-limiting example of a linker peptide may be SEQ ID NO:11.

The term "microbial infection" as used in the context of the invention refers to the invasion, development and/or multiplication of a microorganism within or on another organism. A microbial infection may be localized to a specific region of an organism or systemic. Infections for which a fusion peptide, analog and/or derivative of the invention are useful for treating include any infection which affects mammals, invertebrates, vertebrates and/or plants, caused by any microorganism, for example but not limited to bacteria, fungi, yeasts, protozoa and viruses. A skilled person would understand what is considered a microbial infection. In particular, a fusion protein or analogue or derivative or formulation of the present invention is useful for treating an infection by a virus. Examples of viruses include but are not limited to measles virus, herpes simplex virus (HSV-1 and -2), herpes family members (HIV, hepatitis C, vesicular stomatitis virus (VSV), visna virus, cytomegalovirus (CMV) and the like.

The term "microorganism" as used in the context of the invention encompasses any microscopic organism or microbe. For example, but not limiting, the microorganism includes a bacterium, an archaebacterium, a virus, a yeast, a fungus or a protist. In particular, the microorganism is a virus. The virus may include but are not limited to, cytomegalovirus (CMV) pneumonia, enteritis and retinitis; Epstein-Barr virus (EBV) lymphoproliferative disease; chicken pox/shingles (caused by varicella zoster virus, VZV); HSV-1 and -2 mucositis; HSV-6 encephalitis, BK-virus hemorrhagic cystitis; viral influenza; pneumonia from respiratory syncytial virus (RSV); AIDS (caused by HIV); and hepatitis A, B or C. Additional examples of viruses include but are not limited to Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Bimaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxyiridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class I=internally transmitted; class 2=parenterally transmitted (i.e., Hepatitis C); Norwalk and related viruses, and astro viruses).

For example, the viruses may be specific to aquaculture such as but not limited to Crustacean viruses such as WSSV, HPV, MBV, IHHNV, YHV, TSV, GAV, LSNV, IMNV, MoV, KHV1, KHV2, KHV3, VNN. The viruses specific to aquaculture may include fish viruses from any one of the family of Bimaviridae, Herpesviridae, Iridoviridae, Retroviridae or Rhabdoviridae. In particular, the fish viruses may be pancreatic necrosis virus (IPNV) from the Bimaviridae family, channel catfish virus (CCV) from the Herpesviridae family, fish lymphocystis disease virus (FLDV) from the Iridoviridae family, hematopoietic necrosis virus (IHNV) and viral hemorrhagic septicemia virus (VHSV) belonging to the Rhabdoviridae family and the like. Abalone viruses include AVG, AMAV and the like.

For example, the viruses may be specific to poultry such as but not limited to viruses that cause avian pox, Newcastle disease, infectious bronchitis, quail bronchitis, Marek's Disease (Visceral Leucosis), Lymphoid Leucosis, Infectious Bursal Disease, avian influenza, epidemic tremor and the like.

For example, the viruses may be specific to pigs such as but not limited to swine hepatitis E virus, Circoviruses, Herpesviruses and the like. In particular, the viruses may be Porcine cytomegalovirus, pseudorabies virus.

Viruses significant to cats include but are not limited to The Feline Panleukopenia virus (FPV), Feline herpesvirus, Feline calicivirus, Feline Leukemia Virus (FeLV), Feline Immunodeficiency Virus (Fly) and the like. The viruses may be specific to dogs and these may include but are not limited to Rabies virus, canine parvovirus, canine coronavirus, canine distemper virus, canine influenza, canine hepatitis virus, canine herpesvirus, a virus that causes pseudorabies, canine minute virus and the like.

The term "polypeptide" as used in the context of the invention may refer to a long, continuous, and unbranched peptide and may include cyclic polypeptides. Proteins consist of one or more polypeptides arranged in a biologically functional way and may often be bound to cofactors, or other proteins. In particular, the protein according to any aspect of the present invention may be naturally occurring, de novo and/or synthetic.

The term "subject" as used in the context of the invention refers to any animal, including a human, non-human animal, plant or insect that may be infected by a microorganism. In particular, the subject is any animal, including a human, plant or insect that may be infected by a microorganism against which a fusion protein or analogue or derivative of the invention is active.

The term "treatment", as used in the context of the invention refers to prophylactic, ameliorating, therapeutic or curative treatment.

The term "variant", as used in the context of the invention can alternatively or additionally be characterised by a certain degree of sequence identity to the parent polypeptide from which it is derived. More precisely, a variant in the context of the present invention exhibits at least 30% sequence identity, in particular at least 40%, 50%, 60%, 70%, 80% or 90% sequence identity. More in particular, a variant in the context of the present invention exhibits at least 95% sequence identity to its parent polypeptide. The variants of the present invention exhibit the indicated sequence identity, and preferably the sequence identity is over a continuous stretch of 100, 150, 200, 300, 315, 320, 330, 340, 344 or more amino acids. The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, httpi/hmmer.wustledu/) or with the CLUSTAL available e.g. on http://www.eblac.uk/Tools/clustalw/. Preferred parameters used are the default parameters as they are set on http://www.ebi.ac.uk/Tools/clustalw/ or http://www.ebi.ac.uk/Tools/clustalw2/index.html. The grade of sequence identity (sequence matching) may be calculated using e.g. BLAST, BLAT or BlastZ (or BlastX). Preferably, sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

A person skilled in the art will appreciate that the present invention may be practiced without undue experimentation according to the method given herein. The methods, techniques and chemicals are as described in the references given or from protocols in standard biotechnology and molecular biology text books.

In one aspect of the present invention, there is provided at least one fusion protein comprising a Type 1 RIP or a fragment thereof, polypeptide B; and
(i) at least one polypeptide A capable of viral entry inhibition; and/or
(ii) at least one CAP or a fragment thereof, polypeptide C.

A fusion protein according to the first aspect can also comprise a variant or a derivative. The terms "variant" and "derivative" are defined above. Polypeptide A may be theta defensin, an analogue, or a fragment thereof.

A Cationic Antimicrobial Peptide (CAP) may be an antiviral CAP that may play a role in viral fusion inhibition, viral gene suppression, viral membrane disruption and/or viral entry inhibition. CAPs may be a maximum of 100 amino acids in length. CAPs may mostly be of animal origin. However, there may also be CAPs, which are from plants, which include but are not limited to cyclotides. For example, bacteria CAPs which may function as fusion inhibitors may include but are not limited to Siamycin, NP-06 and Gramicidin A. Plant CAPs which may function as fusion inhibitors may include Circulin A, B, Kalata B1 and B8; Plant CAPs which may function as entry inhibitors may include Kalata B8; Plant CAPs which may function as viral gene suppressors may include Ginkbilobin, Alpha-Basrubin, Lunatusin and Sesquin. Plant CAPs which may function as viral membrane disruptors may include Circulin A, C and D, Tricyclon A and Cycloviolacin H4. Animal CAPs which may function as fusion inhibitors may include Polyphemusin I and II, hfl-B5, Protegrin (Pig Cathelicidin), Rat Defensin NP1, NP2, NP3 and NP4, Human β-defensin I and II, Temporin A, Temporin-LTc, Temporin-Pta, Caerin 1.1, Ranatuerin 6 and 9, Reptile Defensin and Piscidin 1 and 2; Animal CAPs which may function as entry inhibitors include Lactoferricin B, Rabbit Neutrophil-1 Corticostatin III a, Rabbit Neutrophil-3A, Rabbit α-Defensin, Retrocyclin-1, Retrocyclin-2, Retrocyclin-3, Human α-Defensin HNP-1, 2, 3, 4, 5 & 6, Human B-defensin III (HBD3), Rhesus minidefensin (RTD-1,θ-defensin), RTD-2 rhesus θ-defensin, RTD-3 rhesus θ-defensin, Human neutrophil peptide-2, Human neutrophil peptide-3 and human neutrophil peptide-4; Animal CAPs which may function as viral gene suppressors: Cecropin A, Melittin, EP5-1, Magainin 2, hepcidin TH1-5, and Epinecidin-1; Animal CAPs which may function as viral membrane disruptors may include Indolicidin, Cathelicidin-4, Human neutrophil peptide-1, LL-37 Cathelicidin, Dermaseptin-S1, S4 and S9, Maximin 1, 3, 4 and 5, Brevinin 1, Ranatuerin 2P, 6 and 9 Esculentin 2P, Esculentin-1 Arb, Caerin 1.1, 1.9 and 4.1, Brevinin-2-related, Maculatin 1.3, Maximin H5 and Piscidin 1 and 2. Other CAPs may include Mundticin KS Enterocin CRL-35, Lunatusin, FK-13 (GI-20 is a derivative), Tachyplesin I, Alpha-MSH, Antiviral protein Y3, Piscidin 3, Palustrin-3AR, Ponericin L2, Spinigerin, Melectin, Clavanin B, Cow cathelicidin BMAP-27, BMAP-28, Guinea pig cathelicidin CAP11, Sakacin 5X, Plectasin, Fungal Defensin, GLK-19, lactoferrin (Lf) peptide 2, Kalata B8, Tricyclon A, Alloferon 1, Uperin 3.6, Dahlein 5.6, Ascaphin-8, Human Histatin 5, Guineapig neutrophil CAP2 & CAP1, Mytilin B & C, EP5-1, and Hexapeptide (synthetic) Corticostatin IV Rabbit Neutrophil 2.

The Type 1 RIP may:
(i) act as an RNA N-Glycosidase which hydrolyses the N—C glycosidic bond of adenosine at position 4324 of the universally conserved sarcin/ricin domain (S/R domain) of the 28S-rRNA in the eukaryotic ribosome and render it incapable of carrying out protein synthesis thus, functionally, blocking translation,
(ii) act directly on the virus particles or viral nucleic acids by means of their polynucleotide: adenosine glycosidase activity, and/or
(iii) act as a DNA glycosylase/apurinic (AP) lyase capable of irreversibly relaxing HIV-1 supercoiled DNA and catalyzing double-stranded breakage to form inactive products.

In particular, the type 1 RIP may be selected from the group consisting of α-Ebulitin, β-Ebulitin, γ-Ebulitin, Nigritin f1, Nigritin f2, Amarandin-S, *Amaranthus* antiviral/RIP, Amarandin-1, Amarandin-2, Amaranthin, *Atriplex patens* RIP, *Beta vulgaris* RIP, β-vulgin, *Celosia cristata* RIP, *Chenopodium album* RIP, CAP30B, *Spinacea oleracea* RIP, Quinqueginsin, Asparin 1, Asparin 2, Agrostin, Dianthin 29, DAP-30, DAP-32, Dianthin 30, *Dianthus chinensis* RIP1, *Dianthus chinensis* RIP2, *Dianthus chinensis* RIP3, Lychnin, Petroglaucin, Petrograndin, *Saponaria ocymoides* RIP, Vacuolas saporin, Saporin-1, Saporin-2, Saporin-3, Saporin-5, Saporin-6, Saporin-7, Saporin-9, *Vaccaria hispanica* RIP, Benincasin, α-benincasin, β-benincasin, Hispin, Byrodin I, Byrodin II, Colocin I, Colocin 2, *Cucumis figarei* RIP, Melonin, *C. moschata* RIP, Cucurmosin, Moschatin, Moschatin I, Moschatin II, Moschatin III, Moschatin IV, Moschatin V, Pepocin, Gynostemmin I, Gynostemmin II, Gynostemmin III, Gynostemmin IV, Gynostemmin V, *Gynostemma pentaphyllum* RIP, Gypsophilin, Lagenin, Luffaculin, Luffangulin, Luffin-alpha, Luffin-B, MOR-I, MOR-II, Momordin II, Alpha-momorcharin, β-momorcharin, γ δ-momorcharin, γ-momorcharin, Momorcochin, Momorcochin-S, Sechiumin, Momorgrosvin, Trichoanguin, α-kirilowin, β-kirilowin, α-trichosanthin, TAP-29, Trichokirin, Trichomislin, Trichosanthin, Karasurin-A, Karasurin-B, Trichomaglin, Trichobakin, Crotin 2, Crotin 3, Euserratin 1, Euserratin 2, Antiviral Protein GAP-31, Gelonin, *Hura crepitans* RIP, Curcin, *Jathropa curcas* RIP, Mapalmin, Manutin 1, Manutin 2, α-pisavin, Charibdin, *Hyacinthus orientalis* RIP, Musarmin 1, Musarmin 2, Musarmin 3, Musarmin 4, *Iris hollandica* RIP, *Cleroendrum aculeatum* RIP, CIP-29, CIP-34, Crip-31, Bouganin, *Bougainvilla spectbilis* RIP, *Bougainvillea×buttiana* Antiviral protein 1 (BBAP1), malic enzyme 1 (ME1), ME2, MAP-S, pokeweed antiviral protein (PAPa-1), PAPa-2, PAP-alpha, PAP-I, PAP-II, PAP-S, PD-S1, DP-S2, Dodecandrin, Anti-viral protein PAP, PIP, PIP2, *Phytolacca octandra* anti-viral protein, *Phytolacca*, octandra anti-viral protein II, *Hordeum vulgare* RIP-I, *Hordeum vulgare* RIP-II, *Hordeum vulgare* sub sp. *Vulgare* Translational inhibitor II, *Secale cereale* RIP, Tritin, *Zea, diploperemis* RIP-I, *Zea diploperemis* RIP-II, *Malus×domestica* RIP, *Momordica* Anti-HIV Protein (MAP30), *Gelonium multiflorum* (GAP31), pokeweed antiviral protein (PAP), *Mirabilis expansa* 1 (ME1), malic enzyme 2 (ME2), *Bougainvillea×buttiana* antiviral protein 1 (BBAP1), phage MU1, betavulgin (Bvg), curcin 2, saporin 6, Maize RIP (B-32), Tobacco RIP (TRIP), beetin (BE), BE27, *Mirabilis* antiviral protein (MAP), Trichosanthin (TCS), α-luffin, α-Momorcharin (α-MMC), β-MMC luffin, Ocymoidin, Bryodin, Pepopsin, β-trichosanthin, Camphorin, YLP, Insularin, Barley RIP, Tritins, Lamjarin, and *Volvariella volvacea* RIP.

The fusion protein according to any aspect of the present invention may be an antimicrobial compound capable of a broad spectrum of applications and that may be economically produced without any limitation of raw material supply unlike certain antimicrobial compounds known in the art. The fusion protein according to any aspect of the present invention may thus be economically produced in a large scale without any limitations of raw material supply.

In order to achieve broad-spectrum activity, the fusion peptide according to any aspect of the present invention may be able to interfere with the viral infection and propagation processes in a number of different pathways, that is to say, in viral entry inhibition, viral fusion inhibition, viral integrase inhibition and viral translation inhibition. The fusion peptide may thus have a multifunctional ability. An entire new class of antiviral drugs may thus be produced from the fusion protein according to any aspect of the present invention. The number of combinations and permutations that may be obtained from expressed polypeptides A, B and C as fusion antiviral proteins potentially numbers in the tens of thousands.

In particular, the fusion protein may comprise at least one formula selected from the group consisting of formulas I-XIII:

| | |
|---|---:|
| A-B-C, | Formula I |
| A-B-C-C, | Formula II |
| A-B, | Formula III |
| A-C-B, | Formula IV |

C-A-B, Formula V

C-B-A, Formula VI

C-B, Formula VII:

B-A-C, Formula VIII:

B-A-C-C, Formula IX

B-C-A, Formula X

B-A-C, Formula XI

B-C, Formula XII

B-A, Formula XIII

C-C-B-C-C, Formula XIV

C-B-C. Formula XV wherein polypeptide A may be theta defensin, an analogue, or a fragment thereof, polypeptide B may be Type 1 RIP, or a fragment thereof, and polypeptide C may be CAP, or a fragment thereof; and—may be a direct linkage or a linker peptide.

In particular, the linker peptide may comprise a polypeptide sequence: [VPXVG]$_n$, (SEQ ID NO:11) wherein X is an unknown or other amino acid and n is the number of repeats of SEQ ID NO:11 in each linker peptide. For example, n may be 1, 2, 3, 4 or 5. More in particular, X in SEQ ID NO:11 is G and n is 2.

In particular, the fusion protein may comprise the formula I:

A-B-C- wherein, polypeptide A is theta defensin, an analogue, or a fragment thereof, polypeptide B is Type 1 RIP, or a fragment thereof, and polypeptide C is CAP, or a fragment thereof and—may be a direct linkage or a linker peptide.

More in particular, polypeptide A may be fused to polypeptide B via at least one first linker peptide of SEQ ID NO: 11. Even more in particular, polypeptide A may be fused to polypeptide B via a peptide of SEQ ID NO: 11, wherein X is G and n is 2. Polypeptide B may be directly linked to polypeptide C with no linker peptide in-between, Polypeptide C in formula I may comprise a second linker peptide on the free end not linked to B. The second linker peptide may comprise the formula SEQ ID NO: 11. Even more in particular, in the second linker peptide X is G and n is 2.

Polypeptide A may be a theta Defensin of a vertebrate or invertebrate origin. In particular, theta Defensin may be from a bacterium, fungus, mammal, amphibian or reptile. The mammal may be a non-human primate and/or the invertebrate may be a horseshoe crab and/or an insect. The theta Defensin may be selected from the group consisting of Rhesus minidefensin (RTD-1), RTD-2, RTD-3, Retrocyclin-1, Retrocyclin-2, Retrocyclin-3 from *Macaca mulatta* of SEQ ID Nos: 15-20 respectively and the like (Tang Y Q, 1999; Leonava L, 2001; Wang W, 2004).

The theta Defensin may be synthetic and may be selected from a group of retrocyclin congeners RC100-RC108 and RC110-RC114 of SEQ ID NO:21-33 respectively (Cole et. al. 2002: PNAS, V99(4):1813-1818; Wang et. al. 2003: J. Immunol. 170:4708-4716). The sequences of Retrocyclin (RC) 100-108 and RC110-RC114 are shown in Table 1a below.

TABLE 1a

Polypeptide sequences of natually occurring and synthetic theta Defensin proteins.

| SEQ ID NO: | Sequences |
|---|---|
| 15 | GFCRCLCRRGVCRCICTR |
| 16 | RCLCRRGVCRCLCRRGVC |
| 17 | RCICTRGFCRCICTRGFC |
| 18 | GICRCICGRGICRCICGR |
| 19 | GICRCICGRGICRCICGR |
| 20 | RICRCICGRRICRCICGR |
| 21 | GICRCICGRGICRCICGR |
| 22 | GICRCICGKGICRCICGR |
| 23 | GICRCYCGRGICRCICGR |
| 24 | GICRCICGRGICRCYCGR |
| 25 | GYCRCICGRGICRCICGR |
| 26 | GICRCICGRGYCRCICGR |
| 27 | GICYCICGRGICRCICGR |
| 28 | GICICICGYGICRCICGR |
| 29 | GICICICGRGICYCICGR |
| 30 | GICICICGRGICYCICGR |
| 31 | RGCICRCIGRGCICRCIG |
| 32 | RGCICRCIGRGCICRCIG |
| 33 | GICRCICGRGICRCICGR |
| 34 | GICRCICGKGICRCYCGR |

Polypeptide B may be a Type 1 Ribosome Inactivating Protein selected from the group consisting of Ebulitins, Nigritins, Amarandins, *Amaranthus* antiviral/RIP, Amaranthin, *Atriplex patens* RIP, *Beta vulgaris* RIP, β-vulgin, *Celosia cristata* RIP, *Chenopodium album* RIP, CAP30B, *Spinacea oleracea* RIP, Quinqueginsin, Asparins, Agrostin, Dianthins, DAPs, *Dianthus chinensis*', Lychnin, Petroglaucin, Petrograndin, *Saponaria ocymoides* RIP, Vacuolas saporin, Saporins, *Vaccaria hispanica* RIP, Benincasins, Hispin, Byrodin's, Colocins, *Cucumis figarei* RIP, Melonin, *C. moschata* RIP, Cucurmosin, Moschatins, Pepocin, Gynostemmin, *Gynostemma pentaphyllum* RIP, Gypsophilin, Lagenin, Luffaculin, Luffangulin, Luffin, MORs, Momordin II, Momorcharin's, Momorcochin, Momorcochin-S, Sechiumin, Momorgrosvin, Trichoanguin, Kirilowin, α-trichosanthin, TAP-29, Trichokirin, Trichomislin, Trichosanthin, Karasurin, Trichomaglin, Trichobakin, Crotin, Euserratin Antiviral Protein GAP-31, Gelonin, *Hura crepitans* RIP, Curcin, *Jathropa curcas* RIP, Mapalmin, Manutins, α-pisavin, Charibdin, *Hyacinthus orientalis* RIP, Musarmin, *Iris hollandica* RIP, *Cleroendrum aculeatum* RIP, CIPs), Crip-31, Bouganin, *Bougainvilla spectbilis* RIP, *Bougainvillea×buttiana* Antiviral protein 1 (BBAP1), Malic enzymes, MAP-S, pokeweed antiviral proteins (PAP), PD-S1, DP-S2, Dodecandrin, PIP, PIP2, *Phytolacca octandra* anti-viral proteins, *Hordeum vulgare* RIPs, *Hordeum vulgare* sub sp. *Vulgare* Translational inhibitor II, *Secale cereale* RIP, Tritin, *Zea diploperemis* RIPs, *Malus×domestics* RIP, *Momordica* Anti- HIV Protein, *Gelonium multiflorum, Mirabilis expansa* 1, phage MU1, betavulgin (Bvg), curcin 2, saporin 6, Maize RIP (B-32), Tobacco RIP (TRIP), Beetins, *Mirabilis* antiviral protein (MAP), Trichosanthin (TCS), luffins, Momorcharins, Ocymoidin, Bryodin, Pepopsin, β-trichosanthin, Camphorin, YLP, Insularin, Barley RIP, Tritins, Lamjarin, and *Volvariella volvacea* RIP.

Polypeptide C may be selected from the group consisting of Cyclotides, Siamycins, NP-06, Gramicidin A, Circulins, Kalatas, Ginkbilobin, Alpha-Basrubin, Lunatusin, Sesquin, Tricyclon A, Cycloviolacins, Polyphemusins, hfl-B5, Protegrins (Pig Cathelicidin), Rat Defensins, Human β-defensins, Temporins, Caerins, Ranatuerins, Reptile Defensin, Piscidin's, Lactoferricin B, Rabbit Neutrophils, Rabbit α-Defensin, Retrocyclins, Human α-Defensins, Human β-defensin III (HBD3), Rhesus minidefensin (RTD-1,θ-defensin), rhesus θ-defensins, Human neutrophil peptides, Cecropin As, Melittin, EP5-1, Magainin 2s, hybrid (CE-MA), hepcidin TH1-5, Epinecidin-1, Indolicidin, Cathelicidin-4, LL-37 Cathelicidin, Dermaseptins, Maximins, Brevinins, Ranatuerins, Esculentins, Maculatin 1.3, Maximin H5 and Piscidins, Mundticin KS Enterocin CRL-35, Lunatusin, FK-13 (GI-20 is a derivative), Tachyplesins, Alpha-MSH, Antiviral protein Y3, Palustrin-3AR, Ponericin L2, Spinigerin, Melectin, Clavanin B, Cow cathelicidin's, Guinea pig cathelicidin CAP11, Sakacin 5X, Plectasin, Fungal Defensin, GLK-19, lactoferrin (Lf) peptide 2, Alloferon 1, Uperin 3.6, Dahlein 5.6, Ascaphin-8, Human Histatin 5, Guineapig neutrophils, Mytilins, EP5-1, Hexapeptide (synthetic) Corticostatin IV Rabbit Neutrophil 2, Aureins, Latarcin, Plectasin, Cycloviolins, Vary Peptide E, Palicourein, VHL-1.

All references cited are herein incorporated by reference.

In particular, polypeptide A may be a Retrocyclin, polypeptide B may be MAP30 and polypeptide C may be a Dermaseptin. More in particular, polypeptide A may be Retrocyclin 101 (RC101) and polypeptide C may be Dermaseptin 1. A polypeptide comprising RC101, MAP30 and Dermaseptin 1 as polypeptide A, B and C respectively is termed RetroMAD1 in the present invention. RetroMAD1 may exhibit significant viral copy reduction in cell challenge assays for HSV1, HSV2, DEN1, DEN2, DEN3 and DEN4 viruses in pre-treatment, simultaneous and post-treatments as ascertained by RT-PCR.

In particular, polypeptide A may comprise amino acid sequence with SEQ ID NO: 12, a fragment or variant thereof, polypeptide B may comprise amino acid sequence with SEQ ID NO:13, a fragment or variant thereof, and polypeptide C may comprise amino acid sequence with SEQ ID NO:14, a fragment or variant thereof.

More in particular, the fusion protein according to any aspect of the present invention may comprise the amino acid sequence SEQ ID NO:1. The fusion protein or the basic unit of the fusion protein may have a molecular weight of about 10-50 kDa. In particular, the molecular weight of the fusion protein may be 36.5, 37, 37.5, 37.8, 38, 39, 40, 41, 41.2, 43 or 48 kDa. The fusion protein may comprise repeats of the basic unit. A skilled person would understand that the weight of the fusion protein would be dependent on the multiples of the basic unit present in the protein. The sequences are provided in Table 1b below.

In another aspect of the present invention, there is provided at least one isolated nucleic acid molecule capable of expressing the fusion protein according to any aspect of the present invention.

The nucleic acid molecules of the invention can be DNA, cDNA, PNA, CNA, RNA, cDNA, genomic DNA, synthetic DNA, or combinations thereof, and can be double-stranded or single-stranded, the sense and/or an antisense strand. Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription.

The nucleic acid molecules according to the invention can contain naturally occurring sequences, or sequences that differ from those that occur naturally, but, due to the degeneracy of the genetic code, encode the same peptide (for example, the peptides with SEQ ID NOs: 1, 12, 13 and 14). These nucleic acid molecules are not limited to coding sequences and can include some or all of the non-coding sequences that lie upstream or downstream from a coding sequence.

The nucleic acid molecules according to any aspect of the invention can be synthesized in vitro (for example, by phosphoramidite-based synthesis) or obtained from a cell, such as the cell of a bacterium or mammal. The nucleic acids can be those of a vertebrate, an invertebrate, or a higher or lower plant. In particular, the vertebrate may be a mammal, amphibian, reptile, bird, or fish and the lower plant may be a fungi. The mammal may be a human or a non-human. In particular, the non-human may be a non-human primate, mouse, rat, guinea pig, cow, sheep, horse, pig, rabbit, dog, or cat as long as they fulfil the criteria set out above. Combinations or modifications of the nucleotides within these types of nucleic acids are also encompassed.

In particular, the nucleic acid according to the present invention comprises a nucleotide sequence of SEQ ID NO:2, fragment, variant or derivative thereof. In particular, the nucleotide sequence may be at least 50%, 55%, 65%, 75%, 85%, 95%, or 98% identical to SEQ IS NO:2. More in particular, the nucleotide sequence may be capable of encoding a polypeptide of SEQ ID NO:1.

The sequences are provided in Table 1b below.

TABLE 1b

Sequences of polypeptides and polynucleotides of the present invention

| SEQ ID NO: | Sequences |
|---|---|
| 1 | M K Y L L P T A A A G L L L L A A G P A M A M G R I C R C I C G R G I C R C I C G V P G V G V P G V G G A T G S D V N F D L S T A T A K T Y T K F I E D F R A T L P F S H K V Y D I P L L Y S T I S D S R R F I L L D L T S Y A Y E T I S V A I D V T N V Y V V A Y R T R D V S Y F F K E S P P E A Y N I L F K G T R K I T I P Y T G N Y E N L Q T A A H K I R E N I D L G L P A L S S A I T T L F Y Y N A Q S A P S A L L V L I Q T T A E A A R F K Y I E R H V A K Y V A T N F K P N L A I I S L E N Q W S A L S K Q I F L A Q N Q G G K F R N P V D L I K P T G E R F Q V T N V S D V V K G N I K L L L N S R A S T A D E N F I T T M T L L G E S V V E F P W A L W K T M L K E L G T M A L H A G K A A L G A A A D T I S Q G T Q V P G V G V P G V G K L A A A L E H H H H H H |

TABLE 1b-continued

Sequences of polypeptides and polynucleotides of the present invention

| SEQ ID NO: | Sequences |
|---|---|
| 2 | ATGAAATACCTGCTGCCGACCGCTGCTGCTGGTCTGCTGCTCCTCGCTGCCCAGCCGGCGATGGCCATGGGGCGTATTT<br>GCCGTTGCATTTGCGGCCGTGGCATTTGCCGCTGCATCTGTGGCGTGCCGGGTGTTGGTGTTCCGGGTGTGGGTGGTGC<br>GACCGGATCCGATGTGAACTTTGATCTGAGCACCGCGACCGCGAAAACCTATACCAAATTCATCGAAGATTTTCGTGCGA<br>CCCTGCCGTTTAGCCATAAAGTGTATGATATCCCGCTGCTGTATAGCACCATTAGCGATAGCCGTCGTTTTATTCTGCTGG<br>ATCTGACCAGCTATGCGTATGAAACCATTAGCGTGGCGATTGATGTGACCAACGTGTATGTGGTGGCGTATCGTACCCGT<br>GATGTGAGCTACTTTTTCAAAGAAAGCCCGCCGGAAGCGTACAACATTCTGTTTAAAGGCACCCGTAAAATTACCCTGCCG<br>TATACCGGCAACTATGAAAACCTGCAGACCGCGGCGCATAAAATTCGTGAAAACATCGATCTGGGCCTGCCGGCCCTGAG<br>CAGCGCGATTACCACCCTGTTTTATTATAACGCGCAGAGCGCGCCGAGCGCGCTGCTGGTGCTGATTCAGACCACCGCG<br>GAAGCGGCGCGTTTTAAATATATTGAACGCCACGTGGCGAAATATGTGGCGACCAACTTTAAACCGAACCTGGCCATTATT<br>AGCCTGGAAAACCAGTGGAGCGCCCTGAGCAAACAAATTTTTCTGGCCCAGAACCAGGGCGGCAAATTTCGTAATCCGGT<br>GGATCTGATTAAACCGACCGGCGAACGTTTTCAGGTGACCAATGTGGATGACGATGTGGTGAAAGGCAACATTAAACTGC<br>TGCTGAACAGCCGTGCGAGCACCGCGGATGAAAACTTTATTACCACCATGACCCTGCTGGGCGAAAGCGTGGTGGAATTC<br>CCGTGGGCGCTGTGGAAAACCATGCTGAAAGAACTGGGCACGATGGCGCTGCATGCGGGTAAAGCGGCGCTGGGTGCG<br>GCAGCGGATACCATTAGCCAGGGCACCCAGGTTCCGGGCGTGGGCGTTCCGGGCGTTGGTAAGCTTGCGGCCGCACTC<br>GAGCACCACCACCACCACCACTGA |
| 11 | [VPXVG]ₙ |
| 12 | G R I C R C I C G R G I C R C I C G |
| 13 | G S D V N F D L S T A T A K T Y T K F I E D F R A T L P F S H K V Y D I P L L Y S T I S D S R<br>R F I L L D L T S V A Y E T I S V A I D V T N V Y V V A Y R T R D V S Y F F K E S P P E A Y N I<br>L F K G T R K I T L P Y T G N Y E N L Q T A A H K I R E N I D L G L P A L S S A I T T L F Y Y N<br>A Q S A P S A L L V L I Q T T A E A A R F K Y I E R H V A K Y V A T N F K P N L A I I S L E N Q<br>W S A L S K Q I F L A Q N Q G G K F R N P V D L I K P T G E R F Q V T N V D S D V V K G N I<br>K L L L N S R A S T A D E N F I T T M T L L G E S V V E F P W |
| 14 | A L W K T M L K E L G T M A L H A G K A A L G A A A D T I S Q G T Q |

Modifications and changes may be made in the structure of the peptides of the present invention and DNA segments which encode them and still obtain a functional molecule that encodes a protein or peptide with desirable characteristics. The amino acids changes may be achieved by changing the codons of the DNA sequence. For example, certain amino acids may be substituted for other amino acids in a protein structure without appreciable loss of interactive binding capacity with structures such as, for example, microorganism-binding regions of fusion proteins. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. Various changes may be made in the peptide sequences of the disclosed compositions, or corresponding DNA sequences, which encode said proteins without appreciable loss of their biological utility or activity. Amino acid substitutions of the fusion protein according to the present invention may be possible without affecting the antimicrobial effect of the isolated peptides of the invention, provided that the substitutions provide amino acids having sufficiently similar properties to the ones in the original sequences.

The isolated nucleic acid molecules according to the invention encompass segments that are not found as such in the natural state. Thus, the invention encompasses recombinant nucleic acid molecules incorporated into a vector (for example, a plasmid or viral vector) or into the genome of a heterologous cell (or the genome of a homologous cell, at a position other than the natural chromosomal location).

In yet another aspect of the present invention there is provided at least one plasmid or vector comprising the nucleic acid molecule according to any aspect of the present invention.

In one aspect of the present invention there is provided at least one host cell comprising the nucleic acid molecule and/or the plasmid or vector according to any aspect of the present invention.

The DNA (or in the case of retroviral vectors, RNA) may be expressed in a suitable host to produce a polypeptide comprising the fusion protein according to any aspect of the invention. Thus, the DNA encoding the polypeptide constituting the fusion peptide of the invention may be used in accordance with known techniques, to construct an expression vector, which is then used to transform an appropriate host cell for the expression and production of the fusion protein according to the invention.

The DNA (or in the case of retroviral vectors, RNA) encoding the polypeptide constituting the fusion protein of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector may then be introduced into the host through standard techniques. The host cell can be either prokaryotic or eukaryotic. In particular, bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, in particular, vertebrate cells such as those from a mouse, rat, monkey or human fibroblastic and kidney cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-I cells available from the ATCC as CRL 1650 and 293 cells which are human embryonic kidney cells. Preferred insect cells are Sf9 cells, which can be transfected with baculovirus expression vectors.

Transformation of appropriate cell hosts with a DNA construct, nucleic acid molecule and/or plasmid or vector of the present invention is accomplished by well known methods that typically depend on the type of vector used. Electroporation, Biolistic transformation, *Agrobacterium*-mediated and Retroviral-mediated transformation are also useful for transforming and/or transfecting cells and is well known in the art for transforming yeast cell, bacterial cells, insect cells and vertebrate cells.

Usually, not all of the host cells will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Many expression systems are known, including bacteria (for example *Escherichia coli* and *Bacillus subtilis*), yeasts (for example *Saccharomyces cerevisiae* and *Pichia pastoris*), filamentous fungi (for example *Aspergillus*), plant cells, animal cells and insect cells, as above.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention. Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

In another aspect of the present invention there is provided a process of producing a fusion protein according to any aspect of the present invention by culturing the host cell according to the present invention under conditions such that the fusion protein may be expressed. The capital cost of production of the fusion protein according to any aspect of the present invention may be considered low compared to complex synthetic small molecule drugs that require extremely high capital investment often associated with chemical synthesis of multiple functional groups. Since the fusion protein is a biologic, a relatively small capital investment can potentially produce large quantities of products.

In particular, host cells that have been transformed by the recombinant DNA of the invention are then cultured for a sufficient time and under appropriate conditions known to those skilled in the art in view of the teachings disclosed herein to permit the expression of the polypeptide constituting the fusion peptide according to the present invention, which can then be recovered.

In yet another aspect of the present invention there is provided a pharmaceutical composition comprising a fusion protein according to any aspect of the present invention. The pharmaceutical composition may further comprise a pharmaceutically acceptable carrier, excipient, adjuvant, diluent and/or detergent. Such formulations therefore include, in addition to the fusion protein, a physiologically acceptable carrier or diluent, possibly in admixture with one or more other agents such as other antibodies or drugs, such as an antibiotic. Suitable carriers include, but are not limited to, physiological saline, phosphate buffered saline, phosphate buffered saline glucose and buffered saline. Alternatively, the fusion protein may be lyophilized (freeze dried) and reconstituted for use when needed by the addition of an aqueous buffered solution as described above. Routes of administration are routinely parenteral, including intravenous, intramuscular, subcutaneous and intraperitoneal injection or oral delivery. The administration can be systemic and/or local.

In particular, pharmaceutical compositions according to the present invention comprise a ligand which may be at least one fusion protein according to the present invention, a nucleic acid according to the present invention or an expression vector according to the present invention, and a pharmaceutically acceptable carrier as above.

The pharmaceutical composition may be used for topical or parenteral administration, such as subcutaneous, intradermal, intraperitoneal, intravenous, intramuscular or oral administration. For this, the ligands may be dissolved or suspended in a pharmaceutically acceptable, preferably aqueous carrier. The pharmaceutical composition may contain excipients, such as buffers, binding agents, blasting agents, diluents, flavours, lubricants, etc. The composition can be used for a prevention, prophylaxis and/or therapy as an antimicrobial agent.

In particular, the pharmaceutical composition according to any aspect of the present invention may be suitable for oral administration. The pharmaceutical composition may further comprise a detergent. The detergent may be selected from the group consisting of sodium-ursodeoxycholate, sodium glycylursodeoxycholate, potassium-ursodeoxycholate, potassium glycylursodeoxycholate, ferrous-ursodeoxycholate, ferrous glycylursodeoxycholate, ammonium-ursodeoxycholate, ammonium glycylursodeoxycholate, sodium-tauroursodeoxycholate, sodium-N-methylglycylursodeoxycholate, potassium-tauroursodeoxycholate, potassium-N-methygly-cylursodeoxy-cholate, ferrous-tauroursodeoxycholate, ferrous-N-methyglycylursodeoxycholate, ammonium-tauroursodeoxycholate, ammonium-N-methyglycylursodeoxycholate, sodium-N-methyltauroursodeoxycholate, potassium-N-methyltauroursodeoxycholate, ferrous-N-methyltauroursodeoxycholate, ammonium-N-methyltauroursodeoxycholate, sodium-cholate, sodium-deoxycholate, potassium-cholate, potassium-deoxycholate, ferrous-cholate, ferrous-deoxycholate, ammonium-cholate, ammonium-deoxycholate, sodium-chenodeoxycholate, sodium-glycylcholate, potassium-chenodeoxycholate, potassium-glycylcholate, ferrous-chenodeoxycholate, ferrous-glycylcholate, ammonium-chenodeoxychotate, ammonium-glycylcholate, sodium-taurocholate, sodium-N-methylglycylcholate, potassium-taurocholate, potassium-N-methylglycylcholate, ferrous-taurocholate, ferrous-N-methylglycylcholate, ammonium-taurocholate, ammonium-N-methylglycylcholate, sodium-N-methyltaurocholate, sodium-glycyldeoxycholate, potassium-N-methyltaurocholate, potassium-glycyldeoxycholate, ferrous-N-methyltaurocholate, ferrous-glycyldeoxycholate, ammonium-N-methyltaurocholate, ammonium-glycyldeoxycholate, sodium-taurodeoxycholate, sodium-N-methylglycyldeoxychotate, potassium-taurodeoxycholate, potassium-N-methylglycyldeoxycholate, ferrous-taurodeoxycholate, ferrous-N-methyl glycyldeoxycholate, ammonium-taurodeoxycholate, ammonium-N-methylglycyldeoxycholate, sodium-N-methyltaurodeoxycholate, sodum-N-methylglycylchenodeoxycholate, potassium-N-methyltaurodeoxycholate, potassium-N-methylglycylchenodeoxycholate, ferrous-N-methyltaurodeoxycholate, ferrous-N-methylglycylchenodeoxycholate, ammonium-N-methyltaurodeoxycholate, ammonium-N-methylglycylchenodeoxycholate, sodium-N-methyltaurochenodeoxycholate, potassium-N-methyltaurochenodeoxycholate, ferrous-N-methyltaurochenodeoxycholate, ammonium-N-methyltaurochenodeoxycholate, ethyl esters of ursodeoxycholate, propyl esters of ursodeoxycholate, sodium-glycylchenodeoxycholate, potassium-glycylchenodeoxycholate, ferrous-glycylchenodeoxycholate, ammonium-glycylchenodeoxycholate, sodium-taurochenodeoxycholate, potassium-taurochenodeoxycholate, ferrous-taurochenodeoxycholate, ammonium-taurochenodeoxycholate, sodium deoxycholate and the like. In particular, the detergent may be sodium deoxycholate that allows for oral administration as it may result in the fusion protein not being digested in the gastrointestinal tract when consumed. This is a convenient mode of administration.

The detergent may be present at a concentration of 0.003-5% by weight. In particular, the concentration may be 0.01-4.5 wt %, 0.05-4 wt %, 0.1-3.5 wt %, 0.5-2 wt %, 1-1.5 wt %, and the like. In particular, the concentration of the detergent may be about 0.05 wt %.

The pharmaceutical preparation according to the present invention, containing at least one ligand which may be comprise at least one of the fusion protein of the present invention, a nucleic acid according to the invention, or an expression vector according to the invention, may be administered to a patient that suffers from an antimicrobial, and in particular viral infection.

The dosage of the ligand according to the present invention to be administered to a patient suffering from the microbial infection may vary with the precise nature of the condition being treated and the recipient of the treatment. The dose will generally be in the range of about 0.005 to about 1000 mg for an adult patient, usually administered daily for a period between 1 and 30 days. The preferred daily dose is 0.5 to 50 mg per day. In particular the daily dose may be about 0.8, 1, 1.2, 1.5, 2, 2.5, 3.2, 4, 4.5 mg per day. The dosage may be applied in such a manner that the ligand may be present in the medicament in concentrations that provide in vivo concentrations of said ligand in a patient to be treated of between 0.001 mg/kg/day and 5 mg/kg/day. In one embodiment, the pharmaceutical composition, the peptide or ligand according to the invention is present in an amount to achieve a concentration in vivo of 1 µg/ml or above with a maximum concentration of 100 µg/ml. The pharmaceutical preparation of the present invention can further contain at least one host defence molecule, such as lysozyme, lactoferrin and/or Reverse-Transcriptase inhibitor.

The fusion protein and pharmaceutical composition according to any aspect of the present invention may have a broad spectrum of antiviral properties. In particular, the fusion protein and the pharmaceutical composition according to any aspect of the present invention may be useful in developing a broad spectrum, oral delivery antiviral therapeutic. This may be especially beneficial to the many livestock industries which are under pressure from the threat of viral epizootics. This is particularly important as when world population rises, there is also more pressure on food production to become more productive.

In one aspect of the present invention there is provided a method of treating and/or preventing a microbial infection in a vertebrate, invertebrate or plant in need thereof, comprising administering to the vertebrate, invertebrate or plant an effective amount of the fusion protein or the pharmaceutical composition according to any aspect of the present invention.

In another aspect of the present invention there is provided the fusion protein or the pharmaceutical composition according to any aspect of the present invention for use in medicine.

In yet another aspect of the present invention there is provided the fusion protein or the pharmaceutical composition according to any aspect of the present invention for treating and/or preventing a microbial infection in a vertebrate, invertebrate or plant.

In a further aspect of the present invention there is provided a use of the fusion protein according or the pharmaceutical composition according to any aspect of the present invention in the preparation of a medicament for the treatment and/or prevention of a microbial infection in a vertebrate, invertebrate or plant.

In particular, the microbial infection may be a viral infection. The vertebrate may be a mammal, fish or bird. Even more in particular, the mammal may be a non-human animal.

A person skilled in the art will appreciate that the present invention may be practised without undue experimentation according to the method given herein. The methods, techniques and chemicals are as described in the references given or from protocols in standard biotechnology and molecular biology text books.

The fusion protein and/or pharmaceutical composition according to any aspect of the present invention may result in no or substantially no toxic side effects when taken by the subject.

Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

Example 1

Construction and Design of Expression Vector

The gene encoding RetroMAD1 A-B-C with SEQ ID NO:1 was synthesized and cloned into backbone of vector pGA4 at the KpnI/SacI site by contract service (GeneArt AG, Germany). The expected product size was 1140 bp, which encoded a 379 amino acid and an expected size of 41.2 kDa. The polynucleotide sequence and the translated polypeptide sequence are shown in FIG. 1. The gene was sub-cloned into a pET expression vector (Novagen), pET-26(b) at the NcoI/HindIII sites. Kanamycin was used as a marker for selection and maintenance of culture purposes. This vector was inducible under the addition of isopropyl-beta-D-thiogalactopyranoside (IPTG). The plasmid, pRMD1 was then transformed into BL21(DE23) cells (Novagen) and plated on a selective media with Kanamycin.

Expression of RetroMAD1 from *E. coli*

One recombinant clone was grown in 10 ml of LB Bertani (DIFCO) medium, supplemented with 30 μg/ml kanamycin, at 37° C. overnight. This culture was used to inoculate 100 ml of LB Bertani supplemented with 30 μg/ml kanamycin and grown at 37° C. until the optical reading was 0.4-0.6 at 600 nm. IPTG was added at 1.0 mM final concentration. The growth period continued for 3 hours. An SDS-PAGE analysis of the fraction of RetroMAD1 in cells extracted in electrophoresis loading buffer showed that a protein had a molecular mass of about 37.5 kDa, the expected molecular size of RetroMAD1 was produced in the induced cells only (FIG. 2A). Further solubility analysis by SDS-PAGE revealed that RetroMAD1 was found in the pellet fraction and not in the supernatant fraction of the *E. coli* indicating that the protein was expressed and produced as inclusion bodies as shown in FIG. 2B.

Isolation and Purification of RetroMAD1

Cells from 100 ml of induced culture were harvested by centrifugation for 10 min at 5000×g at 15° C. The cells were suspended in a lysis buffer containing 20 mM Tris-HCl (pH 7.5), 10 mM EDTA and 1% Triton-X 100. Cells were disrupted by sonication. The insoluble fraction was isolated from the soluble fraction by centrifugation at 8,000×g for 20 min. The supernatant was discarded and the pellet was further washed by repeating the same step. The pellet was further washed twice with RO water by resuspension via sonication and separation by centrifugation.

Solubilization of RetroMAD1

The insoluble material was dissolved and sonicated in 10 ml of 5-8 Urea or 6M Guanidine Hydrochloride and supplemented with 2-5% of Sodium-lauryl sarcosine and 100 mM β-mercaptoethanol. The solubilisation was carried out overnight. The solubilised protein was separated from the bacterial cell wall by centrifugation at 8,000×g for 20 minutes.

Refolding of RetroMAD1

Renaturation of the protein was carried out by using dialysis. The protein (10 ml) was dialysed in a 15 kDa molecular weight cut-off dialysis membrane (Spectra/Por Lab). The protein was dialysed in 5 L of RO water with the pH of 11.0 adjusted by NaOH. Incubation was done at room temperature for 15-20 hours. The refolded protein was transferred to a 50 ml tube and centrifuged at 8,000×g to separate any insoluble material. Renatured protein was stored at −20° C. until further use. The bioactivity of RetroMAD1 in the following examples is proof of successful refolding of the protein.

Example 2

Virus Stocks

The herpes simplex virus type-1 (HSV-1) and type-2 (HSV-2) were obtained from Medical Microbiology Department in the Faculty of Medicine, University of Malaya. The virus stock was prepared by inoculating monolayer of vero cells in a 25-cm$^2$ tissue culture flask with virus diluted 1:5 to 1:10 in 1 mL of Dulbecco's Modified Eagle Medium (DMEM) (HyClone) containing 2% Fetal bovine serum (FBS) (HyClone). The flask was placed in an incubator at 37° C. to allow virus adsorption. After 1 hour, 4 mL of DMEM supplemented with 2% FBS was added and the cells were allowed to continue propagating at 37° C. for 6 to 7 days until the cytophatic effect (CPE) are confirmed. Cell debris was removed by centrifugation at 1,500×g for 5 minutes. The viral supernatant was collected in aliquots of 1 mL each and stored at −80° C. until further use.

Virus Titration by Plaque Assay

The virulence expressed as plaque forming unit per milliliter (PFU/ml), of each HSV type was titrated by plaque assay using veto cells obtained from Medical Microbiology Department in the Faculty of Medicine, University of Malaya. Vero cells were propagated in 6-well plates ($5 \times 10^5$ cells/well) DMEM with 10% FBS for 24 hours at 37° C. After 24 hours, the growth medium was replaced by serial dilutions of viral supernatants in DMEM with 2% FBS and the cells were further incubated for an hour at 37° C. to allow virus adsorption. Subsequently, an agar overlay was added and the plates were incubated at 37° C. for 5 days (or until the formation of plaque). Upon formation of plaque, the agar overlay was removed and the plaques were stained with 0.1 naphthalene black solution in 6% acetic acid glacial.

In Vitro Virus Inhibition Assay

Pre-treatment assay: Vero cells were seeded in 24-well culture plates at concentration of $1 \times 10^5$ cells per well and incubated for 24 h. Before virus inoculation, maximal non toxic dose of RetroMAD1 were added to the cells and incubated for 24 h. After 24 h of incubation with the peptides, herpes simplex virus-2 (HSV-2) at MOI of 0.1 was inoculated onto the Vero cells for 1 h with occasional rocking. The virus was removed and the cells replaced with fresh DMEM. The cultures were incubated for 24, 48 and 72 h at 37° C. under 5% $CO_2$ atmosphere.

Simultaneous treatment assay: Vero cells were seeded in 24-well culture plates at concentration of $1 \times 10^5$ cells per well and incubated for 24 h. The RetroMAD1 was mixed with virus and incubated at 37° C. for 1 h. The mixture was then inoculated onto Vero cells in 24-well culture plates for 1 h with occasional rocking. The solution was removed and the media was replaced with DMEM. The cultures were incubated for 24, 48 and 72 h at 37° C. under 5% $CO_2$ atmosphere.

Post treatment assay: Vero cells were seeded in 24-well culture plates at concentration of $1 \times 10^5$ cells per well and incubated for 24 h. HSV-2 at MOI of 0.1 was inoculated onto Vero cells in 24-well culture plates for 1 h with occasional rocking. The media was removed and replaced by DMEM containing RetroMAD1. The cultures were incubated for 24, 48 and 72 h at 37° C. under 5% $CO_2$ atmosphere.

At the end of the time period in all antiviral assays the plates were frozen down in −80° C. After 2 cycles of freezing and thawing both supernatant and attached cells were collected. Viral DNA was extracted by extraction kit (Bioneer, South Korea). The eluted DNA was then subjected to RT-PCR.

Viral DNA Extraction and Analysis Using Real-Time PCR

200 μl of culture medium was used for viral DNA isolation using AccuPrep® Genomic DNA Extraction Kit, BioNeer according to the manufacturer's instructions. The purity of total DNA isolated was measured spectrophotometrically. Amplifications and viral load detection was performed using BioRad CFX98 (Biorad). Each 25 μl of SYBR® Green PCR Master Mix contains 1× final concentration of 12.5 μl of SYBR® Green (Biorad), 0.5 μl (0.2 μM) of both forward (HSV-1: 5' TGG GAC ACA TGC CTT CTT GG 3' (SEQ ID NO:3), HSV-2: 5' GTA CAG ACC TTC GGA GG'3 (SEQ ID NO:4)) and reverse primers (HSV-1: 5' ACC CTT AGT CAG ACT CTG TTA CTT ACC C 3' (SEQ ID NO:5), HSV-2: 5' CGC TTC ATC ATG GGC'3 (SEQ ID NO:6)) and 5 μl of template DNA. Thermocyclers started with an initiation step at 95° C. for 15 minutes and followed by 34 cycles of denaturation step at 95° C. for 30 seconds, annealing at 60° C. for 30 seconds and extension at 72° C. for 1 minute and final extension at 72° C. for 5 minutes. The results using HSV-1 primers are shown in Table 2 and FIG. 3 and the results using HSV-2 are shown in Table 3 and FIG. 4. RetroMAD1 was found to be highly effective in inhibiting the progression of HSV infection resulting in more than 90% viral copies reduction in all treatment conditions as shown in FIGS. 3 and 4. The results shown in this study have shown significant inhibition of RetroMAD1 against HSV resulting in a new class of antiviral compound.

TABLE 2

Percentage of viral reduction at post 24- and 48-hours incubation with RetroMAD1: (A) HSV-1 at MOI = 0.1 (B) HSV-1 at MOI 0.5.

(A)

| | MOI 0.1 Time point (hours) | | | |
|---|---|---|---|---|
| | 24 | | 48 | |
| | Virus copies | Viral copy reduction (%) | Virus copies | Viral copy reduction (%) |
| Control | 1642 | 0 | 35530 | 0 |
| Pre-infection treatment | 41 | 98 | 34 | 99.9 |
| Simultaneous treatment | 391 | 77 | 1958 | 94 |
| Post-infection treatment | 132 | 92 | 235 | 99 |

(B)

| | MOI 0.5 Time point (hours) | | | |
|---|---|---|---|---|
| | 24 | | 48 | |
| | Virus copies | Viral copy reduction (%) | Virus copies | Viral copy reduction (%) |
| Control | 1289 | 0 | 31863 | 0 |
| Pre-infection treatment | 27 | 97.89 | 32 | 99.9 |
| Simultaneous treatment | 587 | 54.47 | 10786 | 66.15 |
| Post-infection treatment | 153 | 88.12 | 602 | 98.11 |

TABLE 3

Percentage of viral reduction at post 24- and 48-hours incubation with RetroMAD1: (A) HSV-2 at MOI = 0.1 (B) HSV-2 at MOI 0.5.

(A)

| | MOI 0.1 Time point (hours) | | | |
|---|---|---|---|---|
| | 24 | | 48 | |
| | Virus copies | Viral copy reduction (%) | Virus copies | Viral copy reduction (%) |
| Control | 23 | 0 | 404 | 0 |
| Pre-infection treatment | 13 | 43.2 | 22 | 95 |
| Simultaneous treatment | 7 | 67.74 | 73 | 82 |
| Post-infection treatment | 4 | 81.68 | 19 | 95 |

TABLE 3-continued

Percentage of viral reduction at post 24- and 48-hours incubation with RetroMAD1: (A) HSV-2 at MOI = 0.1 (B) HSV-2 at MOI 0.5.

(B)

| | Time point (hours) | | | |
|---|---|---|---|---|
| | 24 | | 48 | |
| | Virus copies | Viral copy reduction (%) | Virus copies | Viral copy reduction (%) |
| Control | 458 | 0 | 700 | 0 |
| Pre-infection treatment | 6 | 98.7 | 6 | 99.09 |
| Simultaneous treatment | 4 | 99.2 | 24 | 96.55 |
| Post-infection treatment | 6 | 98.8 | 5 | 99.25 |

Example 3

Virus Stocks

The dengue virus type-1 (DENV-1), type-2 (DENV2), type-3 (DENV-3) and type-4 (DENV-4) strain used in this study is a prototype of Hawaii, New Guinea C, H87 and H241 strain respectively (courtesy of Medical Microbiology Department in the Faculty of Medicine, University of Malaya). The virus stock was prepared by inoculating monolayer of C6/36 cells in a 25-$cm^2$ tissue culture flask with virus diluted 1:5 to 1:10 in 1 mL of Leibovitz's L-15 containing 2% FBS. The flask was placed in an incubator at 28° C. to allow virus adsorption. After 1 hour, 4 mL of Leibovitz's L-15 supplemented with 2% FBS was added and the cells were allowed to continue propagating at 28° C. for 6 to 7 days until the cytophatic effect (CPE) are confirmed. Cell debris was removed by centrifugation at 1,500×g for 5 minutes. The viral supernatant was collected in aliquots of 1 mL each and stored at −80° C. until further use.

Virus Titration by Plaque Assay

The virulence expressed as plaque forming unit per milliliter (PFU/ml), of each dengue type was titrated by plaque assay using HepG2 (human hepatoma cell line) cells obtained from Medical Microbiology Department in the Faculty of Medicine, University of Malaya (Phoolcharoen and Smith, 2004). HepG2 cells were propagated in 6-well plates ($5\times10^5$ cells/well) DMEM with 10% Fetal bovine serum (FBS) for 24 hours at 37° C. After 24 hours, the growth medium was replaced by serial dilutions of viral supernatants in DMEM with 2% FBS and the cells were further incubated for an hour at 37° C. to allow virus adsorption. Subsequently, an agar overlay was added and the plates were incubated at 37° C. for 5 days (or until the formation of plaque). Upon formation of plaque, the agar overlay was removed and the plaques were stained with 0.1 naphthalene black solution in 6% acetic acid glacial.

In Vitro Virus Inhibition Assay

The in vitro virus inhibition assay of RetroMAD1 was carried out in duplicates at the compound's MNTD of 100 µg/ml and viral multiplicity of infectivity (MOI) of 0.1 and 0.5. A preformed monolayer of C6/36 cells was prepared in Leibovitz's L-15 (HyClone) in 24-well plates ($5\times10^5$ cells/well). The cells were subjected to three treatments: pre-infection treatment, simultaneous treatment and post-infection treatment. The cells were pre-incubated with RetroMAD1 for 24 hours and diluted virus stock for one hour in preparation for pre-infection treatment and post-infection treatment respectively while both RetroMAD1 and diluted virus stock were incubated at the same time for simultaneous treatment. At post-24 hours and 48 hours incubation time, the culture medium was collected and aliquoted into labeled, 1.5 ml microtubes and kept at −80° C. until further use.

Viral RNA Extraction and Analysis Using Real-Time PCR

200 μl of culture medium was used for viral RNA isolation using AccuPrep® Viral RNA Extraction Kit, BioNeer according to the manufacturer's instructions. The purity of total RNA isolated was measured spectrophotometrically. Amplifications and viral load detection was performed using Bio-Rad CFX98 (Biorad). Each 25 μl of PCR mixture contains 1× final concentration of 12.5 μl of SYBR® Green (Biorad), 1 μl of iScript™ One-Step RT-PCR (Biorad), 0.25 μl (10 NM) of both forward (5' GGA AGG AGA AGG ACT GCA CA 3') (SEQ ID NO:7) and reverse primers (5' ATT CTT GTG TCC CAT CCT GCT 3') (SEQ ID NO:8) and 5 μl of template RNA. Thermocyclers started with an initiation step at 50° C. for 30 minutes and initial denaturation step at 95° C. for 15 minutes, followed by 40 cycles of denaturation at 95° C. for 30 seconds, annealing at 60° C. for 40 seconds and extension at 72° C. for 5 seconds and final extension at 72° C. for 10 minutes. The results of DENV1, DENV2, DENV3 and DENV4 are shown in Tables 4-7 respectively and FIG. 5.

RetroMAD1 was found to be effective against all four dengue serotypes at the MOI of 0.1 in pre-infection treatment condition over an incubation period of 24 hours and 48 hours. Among the serotypes, it was determined that pre-infection treatment with RetroMAD1 gave the best viral inhibition effects against dengue serotype 2 at both MOI 0.1 and 0.5. Both treatment conditions of pre-infection treatment and simultaneous infection give satisfactory inhibition effect in the range of 50%-90% reduction.

TABLE 4

Percentage reduction of DENV1 at post 24- and 48-hours incubation with RetroMAD1 (MOI = 0.1).

| | MOI 0.1 Time point (hours) | | | |
|---|---|---|---|---|
| | 24 | | 48 | |
| | Virus copies (×10$^6$) | Viral copy reduction (%) | Virus copies (×10$^6$) | Viral copy reduction (%) |
| Control | 121.5 | 0 | 1792 | 0 |
| Pre-infection treatment | 44.8 | 63.1 | 107 | 94.0 |
| Simultaneous treatment | 47.2 | 61.2 | 267 | 85.1 |
| Post-infection treatment | 92.1 | 24.2 | 286 | 84.1 |

TABLE 5

Percentage reduction of DENV2 at post 24- and 48-hours incubation with RetroMAD1 at DENV2 (a) MOI = 0.1 and (b) MOI = 0.5

(A)

| | MOI 0.1 Time point (hours) | | | |
|---|---|---|---|---|
| | 24 | | 48 | |
| | Virus copies (×10$^6$) | Viral copy reduction (%) | Virus copies (×10$^6$) | Viral copy reduction (%) |
| Control | 141.2 | 0 | 162.8 | 0 |
| Pre-infection treatment | 0.14 | 80.0 | 0.004 | 99.9 |
| Simultaneous treatment | 28.2 | 68.2 | 0.005 | 99.9 |
| Post-infection treatment | 44.8 | 99.9 | 23.0 | 85.9 |

(B)

| | MOI 0.5 Time point (hours) | | | |
|---|---|---|---|---|
| | 24 | | 48 | |
| | Virus copies (×10$^6$) | Viral copy reduction (%) | Virus copies (×10$^6$) | Viral copy reduction (%) |
| Control | 512.5 | 0 | 203.8 | 0 |
| Pre-infection treatment | 0.004469 | 99.9 | 0.001212 | 99.9 |
| Simultaneous treatment | 229.8 | 55.2 | 178.1 | 12.6 |
| Post-infection treatment | 133.9 | 73.9 | 132.9 | 34.8 |

TABLE 6

Percentage reduction of DENV3 at post 24- and 48-hours incubation with RetroMAD1

| | MOI 0.1 Time point (hours) | | | |
|---|---|---|---|---|
| | 24 | | 48 | |
| | Virus copies (×10$^6$) | Viral copy reduction (%) | Virus copy number (×10$^6$) | Viral copy reduction (%) |
| Control | 1250.7 | 0 | 1874.9 | 0 |
| Pre-infection treatment | 48.3 | 96.1 | 646.6 | 65.5 |
| Simultaneous treatment | 803.6 | 35.7 | 125.2 | 93.3 |
| Post-infection treatment | 637.0 | 49.1 | 1314.1 | 70.1 |

TABLE 7

Percentage reduction of DENV4 at post 24- and 48-hours incubation with RetroMAD1.

| | MOI 0.1 Time point (hours) | | | |
|---|---|---|---|---|
| | 24 | | 48 | |
| | Virus copies | Viral copy reduction (%) | Virus copy number | Viral copy reduction (%) |
| Control | 34852 | 0 | 244764 | 0 |
| Pre-infection treatment | 12386 | 64.5 | 12201 | 95.0 |
| Simultaneous treatment | 18989 | 45.5 | 18989 | 92.2 |
| Post-infection treatment | 16468 | 52.7 | 97337 | 60.2 |

A stray cat with classic symptoms of Feline Immunodeficiency Virus (FIV) such as open lesions as well as gingivitis was treated with RetroMAD1 after conventional medication failed to alleviate the symptoms. This cat was already shown to have FIV using ELISA PCR (results not shown). Immune suppression was evident as Sporotrix infections were seen. The cat was treated with oral doses of 0.68 mg/ml concentration of RetroMAD1 (may be combined with detergent, sodium deoxycholate where the concentration of the detergent was about 0.05 wt %) at 0.6 ml 3× a day mixed into its food. Earlier treatments with cephalexin and itraconazole caused the wounds to shrink by 50% but after that, these open sores did not heal any further. After 14 days of RetroMAD1 treatment, the sores began to heal and within 2 months, they had completely disappeared. During this time, the cat had a good appetite and its weight increased from 4.5 kg to 7.5 kg. Although it remains FIV positive using PCR, this is due to proviral DNA that had already been integrated into the cat's genome and not a sign of viral activity or presence. The cat has been on various RetroMAD1 regimes cumulatively with 8 months of treatment with no apparent changes in behaviour and no apparent side effects.

Similarly, a total of 25 cats with Fly, FeLV, FPV or co-infections with body weights ranging from 2-4.6 kg initial weights were treated with orally administered 0.68 mg/ml RetroMAD1 (may be combined with detergent, sodium deoxycholate where the concentration of the detergent was about 0.05 wt %) at 0.1 ml 3× a day per 1 kg body weight. All were positive for FIV using ELISA and were obviously symptomatic (results not shown). In 2 cases, FIV and FeLV co-infections caused the cats to bleed from the nose, mouth and anus and the cats unable to stand on its feet. In all except one case where the cat died, the subject animals fully recovered faster than if they were on conventional medications only. In the single case where the animal died, the cat was unable to complete its dose regime as the owner wanted to take it back. These results were obtained from 22 Jul. 2010 to 12 Dec. 2011 by a registered Vet at the Puchong Animal Clinic in Kuala Lumpur and two others in Johor, Malaysia.

Five puppies that had classic symptoms of Canine Parvo Virus 2 (CPV2) were treated with 0.68 mg/ml of RetroMAD1 (may be combined with detergent, sodium deoxycholate where the concentration of the detergent was about 0.05 wt %) at 0.1 ml 3× a day per 1 kg body weight. One was a 6 week old Golden Retriever puppy from a litter of 10 where all 10 had CPV2. This puppy was the only one in the litter that was treated with RetroMAD1 (may be combined with detergent, sodium deoxycholate where the concentration of the detergent was about 0.05 wt %). All the other 9 puppies died of CPV2 while the RetroMAD1 treated puppy survived. Another was a toy poodle that had severe CPV2 and was on-drips. After a 7 day treatment with RetroMAD1, the poodle fully recovered. Three half-sibling German Shepherd puppies had severe CPV2 symptoms. After 7 days of treatment with the same regime of RetroMAD1, all three puppies fully recovered. The majority of additional cases were tested during an outbreak of CPV2 in Johor, Malaysia between 24 Oct. 2011 to 16 Dec. 2011.

Although the above are anecdotal results and do not in any way constitute a scientific trial, they do show the effectiveness of RetroMAD1 as an anti-viral drug at a dosage of 200 µg/kg body weight per day.

Cats and dogs tested positive for Fly, FeLV, FPV, Feline Calcivirus, CPV, TVT, Canine Coronavirus, Canine Distemper Virus, respectively have shown significant recovery rate. FIV, FeLV, and CPV have shown a compelling symptomatic recovery rate of 82%, 73% and 76% respectively. Sick animals brought to the clinics are principally screened for diseases. Upon confirmation, the doctors start the RetroMAD1 treatment regime after obtaining the approval of the owners. Majority of these cases have been followed up over the 6-12 months and have not reverted to its previously symptomatic state. However, RetroMAD1 showed zero efficacies for FIPV. Anecdotal trial results were provided by three veterinary practitioners, namely:

(i) Dr Tan Thiam Khoon (Trials from 22 Jul. 2010-1 Oct. 2011) Klinik Haiwan & Surgeri Wawasan
27, Jalan Wawasan 2/22, 47100 Puchong, Malaysia.
Tel: 03-58826422

(ii) Dr B. P. M. Mohanakrishnan (Trials from 24 Oct.-3 Dec. 2011) Hari Pet Clinic & Surgery
No 45, Jalan Chengal, Taman Batu Pahat,
8300 Batu Pahat, Johor, Malaysia
Tel: 07-4349699

(iii) Dr V. C. Vasavan (Trials from 5 Aug.-16 Dec. 2011) 8, Jalan Hj. Abdul Aziz Awab,
Kluang Baru,
86000 Kluang, Johor, Malaysia.
Tel: 07-7745000

TABLE 8

Result summary

| | Disease | Cases | % recovery |
|---|---|---|---|
| Cats | FIV | 11 | 81.8 |
| | FeLV | 11 | 73 |
| | FPV | 1 | 100 |
| | FIPV | 14 | 0 |
| | Lymphoma | 1 | 0 |
| | Calcivirus | 2 | 100 |
| Dogs | CPV | 34 | 76.47 |
| | TVT | 1 | 100 |
| | Coronavirus | 3 | 100 |
| | Distemper Virus | 1 | 0 |

As shown above, anecdotal evidence from 3 Registered Veterinary Practitioners in Malaysia for 11 cases of FIV, 11 cases of FeLV and 34 cases of CPV gave symptomatic recovery rates of 81.8%, 73% and 76.47% respectively when treated with RetroMAD1, that in the Vet's professional opinions were very significant improvements over non-treated cases based on their multi-decade long experience as practicing Vets.

Example 5

Preparation of Peripheral Blood Mononuclear Cells (PBMCs)

PBMC were isolated and blood samples collected into a 10 ml ethylenediaminetetraacetic acid (EDTA)-coated tube by density gradient centrifugation method. It was diluted at the ratio of 1:3 with RPMI-1640 (HyClone), layered onto Lymphoprep (Axis-Shield) and centrifuged at 2000 rpm for 30 minutes. During centrifugation, the PBMCs moved from the plasma and were suspended in density gradient. The PBMCs was washed twice with RPMI-1640 and subsequently were with RPMI-1640 medium. Cell viability was determined by tryphan blue exclusion method. The PBMC cell density used in this study was $1 \times 10^6$ cells/well of the 96-well tissue culture plate. PBMC of Non-Hodgkins' Lymphoma patient was incubated with twelve different concentrations of RetroMAD1 for a period of 72 hours. Cell viability was found to decrease as the range of drug concentration increases from 0.05 µg/ml to 3.13 µg/ml. Cells are found to be most viable at the drug concentration range between 6.25 µg/ml to 50 µg/ml (Table 9).

TABLE 9

Simultaneous treatment with twelve dilutions of RetroMAD1 and its respective percentage of cell viability.

| Concentration (µg/ml) | Cell count | Cell viability (%) |
|---|---|---|
| 0.00 | 475366 | 100.0 |
| 0.05 | 194738 | 41.08 |
| 0.10 | 233484 | 49.26 |
| 0.20 | 195111 | 41.16 |
| 0.39 | 212544 | 44.84 |
| 0.78 | 284545 | 60.03 |
| 1.56 | 311700 | 65.75 |
| 3.13 | 382244 | 80.64 |
| 6.25 | 298088 | 62.89 |
| 12.50 | 325501 | 68.67 |
| 25.0 | 329405 | 69.49 |
| 50.0 | 460283 | 97.10 |
| 100.0 | 423347 | 89.31 |

In Vitro Virus Inhibition Assay

Figure 7:
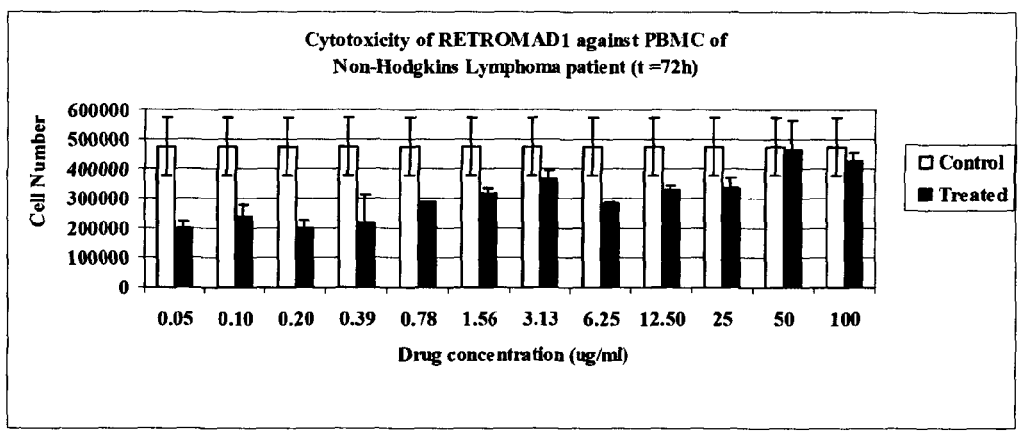
FIG. 7 is a graph showing the cell number of simultaneously treated Non-Hodgkin's Lymphoma PBMC at post-72 hours incubation.

The in vitro virus inhibition assay of RetroMAD1 was carried out in triplicates of wells of a 96 wells plate with the cells were treated simultaneously. Twelve dilutions of RetroMAD1 (concentration of stock: 100 µg/ml) were used to treat both normal and infected PBMC simultaneously and the plate was incubated for 72 hours. At post-72 hours incubation time, the culture was collected. The results are shown in FIGS. 6 and 7. RetroMAD1 was shown not to affect the viability of PBMC isolated from normal donor of the same gender and similar age group (FIG. 7). Therefore, it appears that RetroMAD1 is able to selectively cause the decline of anomalous PBMCs due to its reported ability to target cells where the ultrastructure were altered by viral infection or cancer or both. This is because the MAP30 part of RetroMAD1 has been shown to display 10× more selective toxicity to specific leukemia cells compared to normal PBMCs (Lee-Huang, S. et al., 2000).

Example 6

Cell Culture

Mammalian cell lines (from Medical Microbiology Dept., Faculty of Medicine, Universiti Malaya, Kuala Lumpur, Malaysia) inclusive of Vero (derived from kidney of African Green monkey), LLC-MK2 (derived from kidney of Rhesus monkey) and BHK21 (derived from kidney of baby hamster) cell lines were maintained in a 1× concentrated growth medium of DMEM (HyClone) supplemented with 2% fetal bovine serum (FBS) and 44.04 mmol/L sodium bicarbonate at 37° C. in a humidified incubator with presence of $CO_2$ at 5%. Normal human cell lines (from Medical Microbiology Dept., Faculty of Medicine, Universiti Malaya, Kuala Lumpur, Malaysia) inclusive of Chang's Liver (derived from human liver) which was maintained in a 1× concentrated growth medium of DMEM (HyClone) supplemented with 2% FBS and of 44.04 mmol/L sodium bicarbonate while NL20 (derived from normal human lung) and 184B5 (derived from human breast) was maintained in DMEM/F-12 media (Gibco) supplemented with 2% FBS and mammalian epithelial growth medium (MEGM) respectively and RWPE-1 (derived from human prostate) was maintained in keratinocyte serum-free medium (Gibco) supplemented with 2% FBS. CCD-1127SK (derived from normal human skin) was maintained in Eagle's minimal essential medium supplemented (EMEM) with 2% FBS. These cell lines were kept at 37° C. in a humidified incubator with presence of $CO_2$ at 5%. C6/36 cells (from Medical Microbiology Dept., Faculty of Medicine, Universiti Malaya, Kuala Lumpur, Malaysia) were maintained in a 1× concentrated growth medium of Leibovitz's L-15 (HyClone) supplemented with 10% FBS at 28° C. in the absence of $CO_2$.

Cytotoxicity of RetroMAD1

The cytotoxicity of RetroMAD1 was monitored by evaluating the effects of the compound on cell morphology, viability and growth. $1 \times 10^5$ cells were seeded per well in triplicates at optimal conditions in the presence or absence of RetroMAD1 in a 96-well plate and the plate was observed daily for any changes.

Maximum Non-Toxic Dose (MNTD) of RetroMAD1

The in vitro cytotoxicity analysis was carried out on RetroMAD1 to determine the maximum non-toxic dose (MNTD) to all cell lines used in this experiment. The concentrated stock of RetroMAD1 was diluted to six concentrations (200 µg/ml, 100 µg/ml, 50 µg/ml, 25 µg/ml, 12.5 µg/ml and 6.25 µg/ml) with respective media (depending on the cell line used) before adding to a pre-plated monolayer of cells in 96-well plates. A series of suitable controls for in vitro MNTD determination was included in every plate and the plates are incubated in the optimal conditions. The results are shown in FIG. 8.

Cell Viability Assessment

The cell culture was analyzed at 3 time points; 24 hours, 48 hours and 96 hours with the MTS-CeliTiter 96° $AQ_{ueous}$ Non-Radioactive Cell Proliferation Assay (Promega, USA) according to the manufacturer's protocol (Malich et al., 2004). The results are shown in FIG. 9. RetroMAD1 was found to possess an inhibitory effect on various cell lines at a concentration higher than 100 µg/ml. The MNTD of RetroMAD1 was determined to be at 100 µg/ml.

Example 7

Evidence of Oral Delivery

A total of 47 shrimps (*Palaemonetes* sp) that were confirmed to be naturally infected with hepatopancreatic parvovirus (HPV) confirmed via PCR were used. Two tanks were set up in a bio-secure laboratory; the first tank was for control purposes and the second for treatment with RetroMAD1. The treated group was given RetroMAD1 (combined with detergent, sodium deoxycholate where the concentration of the detergent was about 0.05 wt %) at 100 ng/g feed, 3 times daily for 4 days. RetroMAD1 was absorbed by the prawn feed and given orally.

DNA extraction was carried out using the 'salting-out' procedure. PCR was done using specific primers for detection of HPV. The primers used were fHPV: 5'-ACA-CTC-AGC-CTC-TAC-CTT-GT 3'(SEQ ID NO:9) and rHPV: 5'-GCA-TTA-CAA-GAG-CCA-AGC-AG-3' (SEQ ID NO:10). A positive detection would produce a PCR product with the size of 441 bp.

The agarose gel results showed that in the control tank (FIG. 10A), 22/23 prawns were infected with HPV while in the treated tank (FIG. 10B), 22/24 were negative for HPV. This showed that orally administered RetroMAD1 appeared to have eliminated HPV from the test animals completely.

Example 8

Further Evidence of Oral Delivery

White Leg Shrimp Penaeus vannamei with an average body weight of 8 g+/−0.5 g that had been pond-reared from SPF (specific pathogen free) post-larvae obtained from commercial hatcheries were used. After transfer in oxygenated containers from the ponds, these animals were first acclimated in BioSecure laboratory tanks for a period of 14 days. Each tank consisted of 20 prawns reared in 100 L tanks. The shrimps received 4 meals per day corresponding to approximately 3.5% of body weight. Finally, they were infected orally challenged by feeding frozen flesh from PCR positive prawns obtained from a recently White Spot Syndrome Virus (WSSV)-killed pond at approximately 4% of body weight. RetroMAD1 (combined with detergent, sodium deoxycholate where the concentration of the detergent was about 0.05 wt %) was administered after 24 hours of infection, at 0.1 mg/g feed that was left to absorb 15 minutes to the pellet prior to feeding.

In the untreated control, mortalities began on day 3 post-challenge and by day 8, nearly all of the 20 animals were dead. By day 9 post-challenge, 100% mortality was observed in the control tank showing that the WSSV-infected carcass used was very much capable of causing 100% mortality within 9 days post-oral infection. The results indicate that RetroMAD1 was successful in protecting the challenged animals against acute death by WSSV (FIG. 11).

Example 9

Acute Toxicity Test in Imprinting Control Region (ICR) Mice

Adult male and female ICR mice (6-8 weeks old) were obtained from the Animal House, Faculty of Medicine, University of Malaya, Kuala Lumpur (Ethics No. PM Jul. 5, 2008 MAA (a) (R). The mice weighed between 25-35 g. The animals were given standard rat pellets and tap water. The acute toxic study was used to determine a safe dose for RetroMAD1 Thirty six mice (18 males and 18 females) were separated into 3 groups and each group was fed orally once with (a) a vehicle only (normal saline, 5 ml/kg); (b) 0.105 mg/kg of Retro-MAD1 prepared in normal saline and 1.05 mg/kg of Retro-MAD1 of RetroMAD1 prepared in normal saline. The animals fasted overnight (food but not water) prior to dosing. Food was withheld for a further 3 to 4 hours after dosing. The animals were observed for 30 min and 2, 4, 8, 24 and 48 h after the administration for the onset of clinical or toxicological symptoms. Mortality, if any was observed over a period of 2 weeks. The animals were fasted on 14th day and sacrificed on the 15th day by an overdose of Ketamine anesthesia. Histological, hematological and serum biochemical parameters were determined following standard methods (Bergmeyer, 1980; Tietz et al., 1983). The results are shown in Table 10.

The study was approved by the ethics committee for animal experimentation, Faculty of Medicine, University of Malaya, Malaysia. All animals received human care according to the criteria outlined in the "Guide for the Care and Use of laboratory Animals" prepared by the National Academy of Sciences and published by the national Institute of health.

TABLE 10

Results of histological, hematological and serum biochemical parameters obtained from carrying out test on the measured from the control and tested ICR mice.

| Electrolytes/ Renal function tests | Control Male | Control Female | Low Dose Male | Low Dose Female | High Dose Male | High Dose Female |
|---|---|---|---|---|---|---|
| Sodium | 145.83 | 147.33 | 148.83 | 147.17 | 148 | 148.83 |
| Potassium | 7.57 | 5.67 | 7.18 | 5.18 | 6.93 | 5.77 |
| Chloride | 112.83 | 112 | 111 | 111 | 110.75 | 112.33 |
| Carbon Dioxide | 16.08 | 16.07 | 18.5 | 18.02 | 18.05 | 15.05 |
| Anion Gap | 24.5 | 25 | 27.17 | 23.5 | 26.5 | 27.33 |
| Urea | 10.87 | 9.4 | 9.27 | 6.68 | 8.6 | 11.48 |
| Creatinine | 21.67 | 16 | 18.67 | 13 | 14 | 13 |
| Liver Function Test | | | | | | |
| Total Protein | 51.33 | 53.67 | 50.5 | 55.17 | 51 | 53.17 |
| Albumin | 13.33 | 15.83 | 12.67 | 16.33 | 12 | 15.67 |
| Globulin | 38 | 37.83 | 37.83 | 38.83 | 39 | 37.5 |
| Total Bilirubin | 4.5 | 3.5 | 5 | 3.83 | 4.67 | 3.33 |
| Conjugated bilirubin | <1 | <1 | <1 | <1 | <1 | <1 |
| ALT | 28.83 | 29.17 | 36.67 | 30.17 | 32 | 32.5 |
| AST | 141.17 | 141.33 | 110 | 146.67 | 104.75 | 173.17 |
| ALP | 81.5 | 104.33 | 72.67 | 116.5 | 62.75 | 121.83 |
| G-Glutamyl Transferase | <3 | <3 | <3 | <3 | <3 | <3 |
| Lipid Profile Tests | | | | | | |
| Triglyceride | 0.91 | 1.2 | 1.47 | 1.4 | 1.62 | 1.46 |
| Total Cholesterol | 3.57 | 2.62 | 3.9 | 2.67 | 3.55 | 2.57 |
| HDL Cholesterol | 3.26 | 2.55 | 3.44 | 2.6 | 3.1 | 2.46 |
| LDL Cholesterol | −0.25 | −0.47 | −0.27 | 0.57 | 0.53 | −0.39 |

The results of Table 9 show that there are no significant differences between male, female and between treated (low and high dose) and control. The results of the histopathology of liver and Kidney in ICR mice also showed no significant differences between male, female and between treated (low and high dose) and control. These results confirm that administration of RetroMAD1 may be considered non-toxic or at least minimally toxic on IRC mice to which the drug is administered at 50× and 500× the dose used to treat the cats and dogs (Table B), where significant symptomatic recovery was observed by 3 separate veterinary practitioners.

Example 10

Primate Toxicology

Fifteen healthy male and female monkeys (12-18 months old) of the *Macaca fascicularis* breed species weighing 1.5-1.7 kg were used. The monkeys were divided 5 per group; control (no RetroMAD1 treatment), low dose (0.2 mg/kg body weight) and high dose (2.4 mg/kg body weight). The dosage established as low dose and high dose for this study is actually 4× and 48× the mouse dose which is calculated from the Equivalent Surface Area Dosage Conversion Factors. Each group of animal was administered with the corresponding dose level of RetroMAD1 incorporated in their usual diet and given twice a day for a period of 4 weeks. All animals were observed to be active throughout the study duration and after two months post-dosing. All hematology parameters are within normal range. Although hematocrit, mean corpuscular volume, thrombocit, monocytes and some eosinophil granulocytes in all three groups exhibited values out the normal range, the differences are minimal (tolerable value). (Tables 11A and 11B)

Whereas, the only parameter which was not within the normal range in the blood chemistry test was Globulin but the discrepancy is only very minimal (tolerable value). However, the most glaring difference is in the Chloride. This is expected due to the effect of bleeding in the homeostasis condition of the animal in regard to the functionality of the ion. (Table 12)

One animal from each group was euthanized to conduct histopathology observation. The histopathological findings strongly suggest that High Dose level of RetroMAD1 could possibly elicit toxic effect on the specific organs that were examined. Lung, liver, intestine and kidney were among the organs in the High dose groups exhibiting significant lesions. Lesions found in the representative animal belonging under the Control (untreated) and Low dose group could be attributed to other causes. Low dose and High dose administered is equivalent to four times and forty eight times the normal dose respectively. Therefore, whereas the 50× and 500× single doses did not appear to show any appreciable toxicity in ICR mice, the 48× multiple dose in monkeys showed significant lesions in the organs suggesting that doses for human treatment should be around 1-4× the dose used on the cats and dogs. This study was conducted at Simian Conservation Breeding & Research Centre Inc. (SICONBREC), Philippines accredited by AAALAC. Referral interpretation was provided by Veterinary experts from the College of Veterinary Medicine in University of Philippines Los Baños.

TABLE 11B

Mean Hematology Data - Toxicity

| GROUP | DIFFERENTIAL COUNT | | | | | |
|---|---|---|---|---|---|---|
| | LYM ($10^3$/ul) | MID ($10^3$/ul) | GRA ($10^3$/ul) | LYM (%) | MID (%) | GRA (%) |
| Control | | | | | | |
| Pre-Bleed | 4.66 | 0.10 | 4.58 | 50.34 | 0.78 | 48.90 |
| Mid-Bleed | 4.78 | 0.24 | 4.72 | 50.32 | 2.64 | 47.02 |
| $2^{nd}$ Mid-Bleed | 5.48 | 0.26 | 5.68 | 48.82 | 2.00 | 49.20 |
| End-Bleed | 5.68 | 0.28 | 4.60 | 58.00 | 2.66 | 39.38 |
| Low Dose | | | | | | |
| Pre-Bleed | 4.22 | 0.10 | 5.88 | 41.68 | 0.80 | 57.56 |
| Mid-Bleed | 5.94 | 0.28 | 5.68 | 51.10 | 1.66 | 47.24 |
| $2^{nd}$ Mid-Bleed | 7.34 | 0.10 | 5.56 | 55.96 | 0.72 | 43.36 |
| End-Bleed | 5.68 | 0.06 | 3.10 | 63.54 | 0.66 | 35.78 |
| High Dose | | | | | | |
| Pre-Bleed | 5.76 | 0.10 | 4.24 | 57.82 | 0.82 | 41.38 |
| Mid-Bleed | 7.06 | 0.10 | 7.06 | 50.38 | 0.74 | 48.90 |
| $2^{nd}$ Mid-Bleed | 7.96 | 0.10 | 5.68 | 57.50 | 0.68 | 41.80 |
| End-Bleed | 7.00 | 0.10 | 3.92 | 61.98 | 0.68 | 37.30 |

TABLE 11A

Mean Hematology Data - Toxicity

| GROUP | WBC ($10^3$/ul) | RBC ($10^3$/ul) | HGB (g/dl) | HCT (%) | MCV (fl) | MCH (pg) | MCHC (g/dl) | RDWc (%) | PLT ($10^3$/ul) | PCT ($10^3$/ul) | MPV (fl) | PDWc (%) |
|---|---|---|---|---|---|---|---|---|---|---|---|---|
| Control | | | | | | | | | | | | |
| Pre-Bleed | 9.34 | 7.52 | 113.00 | 38.14 | 50.80 | 15.06 | 296.20 | 15.88 | 461.40 | 0.34 | 7.74 | 38.20 |
| Mid-Bleed | 9.74 | 7.10 | 110.40 | 36.84 | 52.00 | 15.56 | 299.80 | 15.88 | 297.80 | 0.20 | 7.06 | 35.90 |
| $2^{nd}$ Mid-Bleed | 11.42 | 7.19 | 111.40 | 36.76 | 51.20 | 15.54 | 303.80 | 15.62 | 446.80 | 0.34 | 7.82 | 37.74 |
| End-Bleed | 10.52 | 7.61 | 117.60 | 36.98 | 48.40 | 15.48 | 320.60 | 15.74 | 478.20 | 0.38 | 7.48 | 37.32 |
| Low Dose | | | | | | | | | | | | |
| Pre-Bleed | 10.16 | 7.38 | 115.40 | 37.62 | 51.20 | 15.66 | 307.40 | 15.58 | 395.20 | 0.30 | 8.10 | 39.56 |
| Mid-Bleed | 11.88 | 7.20 | 112.40 | 37.40 | 52.20 | 15.64 | 300.20 | 15.72 | 273.00 | 0.20 | 7.06 | 36.68 |
| Pre-Bleed | 12.98 | 6.93 | 108.20 | 35.40 | 51.20 | 15.64 | 305.40 | 15.46 | 363.40 | 0.30 | 8.24 | 39.44 |
| End-Bleed | 8.80 | 7.31 | 113.40 | 33.64 | 46.20 | 15.60 | 345.40 | 16.26 | 757.80 | 0.44 | 6.92 | 34.34 |
| High Dose | | | | | | | | | | | | |
| Pre-Bleed | 10.12 | 8.01 | 115.60 | 39.32 | 49.00 | 14.48 | 294.80 | 16.16 | 467.40 | 0.38 | 8.12 | 39.00 |
| Mid-Bleed | 14.26 | 7.34 | 108.20 | 36.36 | 49.80 | 14.78 | 298.00 | 16.04 | 311.20 | 0.20 | 7.04 | 36.42 |
| $2^{nd}$ Mid-Bleed | 13.72 | 7.29 | 106.00 | 35.48 | 48.80 | 14.54 | 298.40 | 15.70 | 417.80 | 0.34 | 8.18 | 39.14 |
| End-Bleed | 10.96 | 7.64 | 110.20 | 31.32 | 41.40 | 14.46 | 356.00 | 16.88 | 611.80 | 0.42 | 6.58 | 36.70 |

TABLE 12

Mean Blood Chemistry Data - Toxicity

| GROUP | GLU (mg/dl) | TRIG (mg/dl) | BUN (mg/dl) | CREA (mg/dl) | TP (g/dl) | ALB (g/dl) | GLOB (g/dl) | GOT (IU/L) | GPT (IU/L) | Tbil. | Chlor | K | Na |
|---|---|---|---|---|---|---|---|---|---|---|---|---|---|
| Control | | | | | | | | | | | | | |
| Pre-Bleed | 41.83 | 19.81 | 19.64 | 0.74 | 6.98 | 4.46 | 2.52 | 36.60 | 20.40 | 0.47 | 99.43 | 3.60 | 144.17 |
| Mid-Bleed | 64.23 | 47.05 | 26.77 | 0.70 | 7.22 | 4.91 | 2.32 | 37.80 | 19.20 | 0.49 | 104.62 | 3.25 | 150.74 |
| End-Bleed | 54.22 | 32.98 | 20.03 | 0.73 | 7.54 | 5.16 | 2.38 | 45.40 | 23.00 | 0.61 | 101.42 | 5.13 | 140.74 |
| Low Dose | | | | | | | | | | | | | |
| Pre-Bleed | 46.76 | 22.46 | 18.98 | 0.71 | 7.42 | 4.53 | 2.89 | 50.20 | 22.60 | 0.53 | 99.54 | 3.61 | 144.74 |
| Mid-Bleed | 77.21 | 47.14 | 26.93 | 0.72 | 7.25 | 4.76 | 2.49 | 45.80 | 21.20 | 0.50 | 111.40 | 3.29 | 148.99 |
| End-Bleed | 58.67 | 28.97 | 19.32 | 0.71 | 7.88 | 4.55 | 3.33 | 41.40 | 20.60 | 0.52 | 105.39 | 5.77 | 143.90 |
| High Dose | | | | | | | | | | | | | |
| Pre-Bleed | 49.33 | 29.98 | 18.15 | 0.71 | 7.36 | 4.67 | 2.69 | 43.40 | 15.40 | 0.51 | 98.19 | 3.65 | 147.10 |
| Mid-Bleed | 86.38 | 67.30 | 28.77 | 0.74 | 7.00 | 4.90 | 2.10 | 44.00 | 17.40 | 0.51 | 110.96 | 3.26 | 150.86 |
| End-Bleed | 61.72 | 41.43 | 21.09 | 0.70 | 7.47 | 4.38 | 3.08 | 39.80 | 16.80 | 0.55 | 103.02 | 4.68 | 142.27 |

These results prove that RetroMAD1 is a safe drug where the toxicity dose is very high. A summary of the acronyms and references used in Examples 10 and 11 are provided in the Table 13 below.

TABLE 13

Legend used in hematology experiments

| Abbreviation | | Units | Reference point |
|---|---|---|---|
| WBC | White Blood Cell | $10^3/\mu l$ | 7.0-22.5 |
| RBC | Red Blood Cell | $10^6/\mu l$ | 5.7-8.7 |
| HGB | Hemoglobin concentration | g/dl | 99.0-126.0 |
| HCT | Hematocnl | % | 32.3-41.7 |
| MCV | Mean Corpuscular Volume | Fl | 43.0-58.0 |
| MCH | Mean Corpuscular Hemoglobin | Pg | 13.6-18.5 |
| MCHC | Mean Corpuscular Hemoglobin Concentration | g/dl | 281.0-338.0 |
| RDWc | Red cell Distribution Width | % | 13.9-17.4 |
| PLT | Platelet | $10^3/\mu l$ | 155.0-586.0 |
| PCT | Thrombocit | % | 0.1-0.4 |
| MPV | Mean Platelet Volume | Fl | 5.8-9.2 |
| PDWc | Platelet Distribution Width | % | 32.2-43.5 |
| LYM | Lymphocytes | $10^3/\mu l$ | 3.7-11.2 |
| MID | Monocytes and some eosinophil granulocytes | $10^3/\mu l$ | 0.1-0.4 |
| GRA | Neutrophil, eosinophil and basophil granulocytes | $10^3/\mu l$ | 2.7-14.9 |
| L % | Lymphocytes | % | 32.8-69.0 |
| MID % | Monocytes and some eosinophil granulocytes | % | 0.7-3.6 |
| GR % | Neutrophil, eosinophil and basophil granulocytes | % | 28.9-66.4 |
| GLU | Glucose | mg/dl | 23.8-121.6 |
| ALB | Albumin | g/dl | 4.2-5.6 |
| TRIG | Triglycerides | mg/dl | 14.2-67.4 |
| BUN | Blood Urea Nitrogen | mg/dl | 12.1-47.9 |
| CREA | Creatinine | mg/dl | 0.6-1.0 |
| TP | Total Protein | g/dl | 6.7-8.2 |
| GOT | Serum Glutamate Oxaloacetate Transaminase (AST) | IU/L | 30.0-68.0 |
| GPT | Serum Glutamate Pyruvic Transaminase (ALT) | IU/L | 10.0-38.0 |
| K | Pottasium | mmol/L | 3.0-4.2 |
| Na | Sodium | mmol/L | 136-152.4 |
| GLOB | Globulin | g/dl | 1.7-3.2 |
| Chlor | Chloride | mEg/L | 88.7-101.3 |

Example 11

Treatment Using RetroMAD1 in a Primate Model

Ten sick Cynomolgus monkeys weighing 1-1.7 kg confirmed to be infected with Simian Rota Virus A were isolated for this experiment. RNA was extracted from their fecal sample to be tested for Rota virus by PCR. The monkeys were divided with 5 heads per group; control (no RetroMAD1 treatment) and treatment (0.2 mg/kg body weight). Retro-MAD1 was incorporated into their daily diet which also includes 20 ml Cerelac each for a period of 4 weeks. Control group had 3 mortalities (60% mortality) which incurred on the $11^{th}$ and the $14^{th}$ day of the study period. Animals in this batch were observed with poor to fair condition. The treatment group was active. All treated animal's survived (0% mortality). This trial was conducted at the SICONBREC facility in Philippines. Referral interpretation was provided by Veterinary experts from the College of Veterinary Medicine in University of Philippines Los Banos.

Hematology parameters which were affected are HGB, HCT, RDWc, PLT and PCT. PLT exhibited the most comparable data. Both the control untreated and sick treated showed a significantly higher value than the normal range of values obtained. The higher end of the normal value is 586.0 ($10^3$/ul) whereas in the control the end-bleed dosing was 596.0 ($10^3$/μl) and in the treatment the end-bleed dosing it was 627.4 ($10^3$/ul). Rationale provided by expert is that the higher value of these parameters is due to the body's defensive mechanism responding to combat the infection. (Tables 14A and B)

The blood chemistry of the sick batch of monkeys has varying results in the control and treatment group which is a good indication of the natural response of the monkeys to the treatment done. The BUN, CREA and TP in the control group were all below the minimum value of the range of values obtained from each parameter which can be related to pathophysiology. There is a normal proportion of Albumin to Globulin. If one protein becomes lower the other protein will try to compensate to balance the colloidal osmotic pressure of the blood. This is seen as low values of Albumin in the both control and treatment groups but higher values of Globulin in both control and treatment groups. The ions Chlor, K and Na are likewise affected. The bleeding plus the diarrhea can drastically affect the fluid-electrolyte balance as seen in varying results for these ions. (Table 15)

TABLE 14A

Mean Hematology - Sick

| GROUP | WBC ($10^3$/ul) | RBC ($10^3$/ul) | HGB (g/dl) | HCT (%) | MCV (fl) | MCH (pg) | MCHC (g/dl) | RDWc (%) | PLT ($10^3$/ul) | PCT ($10^3$/ul) | MPV (fl) | PDWc (%) |
|---|---|---|---|---|---|---|---|---|---|---|---|---|
| Control | | | | | | | | | | | | |
| Pre-Bleed | 8.34 | 6.79 | 101.40 | 32.40 | 47.80 | 14.90 | 312.60 | 15.44 | 544.00 | 0.42 | 7.92 | 37.98 |
| Mid-Bleed | 8.25 | 6.03 | 87.00 | 29.05 | 48.50 | 14.50 | 299.50 | 17.40 | 490.50 | 0.30 | 6.20 | 33.95 |
| $2^{nd}$ Mid-Bleed | 9.30 | 5.78 | 82.50 | 27.55 | 47.50 | 14.30 | 299.00 | 17.30 | 453.00 | 0.35 | 7.75 | 38.25 |
| End-Bleed | 14.00 | 6.32 | 90.50 | 28.30 | 45.00 | 14.30 | 321.00 | 17.80 | 596.00 | 0.45 | 7.65 | 37.15 |
| Treatment | | | | | | | | | | | | |
| Pre-Bleed | 13.12 | 7.09 | 108.00 | 35.38 | 49.80 | 15.24 | 305.60 | 15.68 | 584.20 | 0.48 | 8.08 | 37.94 |
| Mid-Bleed | 14.32 | 7.18 | 108.80 | 36.16 | 50.00 | 15.16 | 301.20 | 15.44 | 485.60 | 0.32 | 6.74 | 34.90 |
| Pre Bleed | 13.10 | 6.02 | 90.60 | 30.08 | 50.00 | 15.08 | 301.80 | 15.30 | 507.60 | 0.42 | 8.26 | 38.26 |
| End-Bleed | 12.50 | 6.76 | 102.60 | 32.58 | 48.40 | 15.18 | 314.60 | 16.26 | 627.40 | 0.50 | 8.28 | 39.44 |

TABLE 14B

Mean Hematology - Sick

DIFFERENTIAL COUNT

| GROUP | LYM ($10^3$/ul) | MID ($10^3$/ul) | GRA ($10^3$/ul) | LYM (%) | MID (%) | GRA (%) |
|---|---|---|---|---|---|---|
| Control | | | | | | |
| Pre-Bleed | 3.42 | 0.20 | 4.74 | 41.12 | 3.18 | 55.70 |
| Mid-Bleed | 3.50 | 0.15 | 4.60 | 42.40 | 2.85 | 54.80 |
| $2^{nd}$ Mid-Bleed | 4.95 | 0.40 | 4.00 | 52.75 | 4.40 | 42.80 |
| End-Bleed | 5.95 | 1.15 | 6.60 | 42.75 | 9.95 | 47.30 |
| Treatment | | | | | | |
| Pre-Bleed | 4.34 | 0.52 | 8.32 | 40.36 | 3.42 | 56.24 |
| Mid-Bleed | 5.02 | 0.56 | 8.70 | 34.98 | 4.10 | 60.94 |
| $2^{nd}$ Mid-Bleed | 5.68 | 0.46 | 6.94 | 43.04 | 3.20 | 53.76 |
| End-Bleed | 5.80 | 0.30 | 6.40 | 47.64 | 2.14 | 50.22 |

TABLE 15

Mean Blood Chemistry - Sick

| GROUP | GLU (mg/dl) | TRIG (mg/dl) | BUN (mg/dl) | CREA (mg/dl) | TP (g/dl) | ALB (g/dl) | GLOB (g/dl) | GOT (IU/L) | GPT (IU/L) | Tbil. | Chlor | K | Na |
|---|---|---|---|---|---|---|---|---|---|---|---|---|---|
| Control | | | | | | | | | | | | | |
| Pre-Bleed | 68.08 | 41.51 | 32.65 | 0.89 | 7.00 | 3.67 | 3.32 | 37.60 | 12.00 | 0.82 | 86.52 | 3.43 | 133.19 |
| Mid-Bleed | 32.04 | 53.73 | 6.39 | 0.52 | 5.74 | 3.31 | 2.43 | 38.50 | 25.50 | 0.42 | 117.35 | 3.66 | 162.34 |
| End-Bleed | 47.96 | 40.01 | 20.28 | 0.60 | 6.73 | 3.03 | 3.70 | 29.50 | 19.00 | 0.41 | 106.57 | 6.74 | 144.96 |
| Treatment | | | | | | | | | | | | | |
| Pre-Bleed | 55.18 | 65.15 | 23.49 | 0.96 | 7.45 | 3.65 | 3.81 | 42.20 | 16.000 | 0.61 | 93.55 | 3.46 | 139.03 |
| Mid-Bleed | 62.74 | 52.85 | 11.17 | 0.65 | 6.44 | 3.14 | 3.30 | 31.00 | 11.00 | 0.45 | 110.44 | 4.21 | 153.54 |
| End-Bleed | 60.95 | 60.65 | 10.76 | 0.85 | 7.93 | 3.19 | 4.74 | 27.50 | 12.00 | 0.44 | 101.17 | 6.02 | 137.28 |

Example 12

Teratogenicity Studies

Thirty, Day 1 pregnant Sprague Dawley (SD) adult female rats were randomly divided into 3 groups and each group fed orally with (a) sterile distilled water (1 ml/kg bodyweight, 0.2 ml/200 g rat); (b) 5 mg/kg of RetroMAD1 prepared in normal saline and (c) 10 mg/kg of RetrOMAD1 prepared in normal saline. The above mentioned regime was carried out for the adult female rats from day 1 pregnancy to day 20 and continued for 21 days post-delivery.

There are no signs of maternal toxicity or embryogenicity at 10 mg drug/kg body weight of pregnant rats treated from day 1 to day 20. There are no external fetal abnormalities, no growth delay, and no fetal death. The dam's (mother) weight gain after dosing, low and high dose of drug (gestational days 1 to 20) were comparable to normal control group. None of the pregnant rats delivered prematurely. The duration of gestation was unaffected by RetroMAD1.

There was no difference observed in dam-pup interactions between the drug-treated groups and normal control group. Each dam was able to nurse, and each pup was able to suckle. There were no observed differences between the groups as to when the offspring began to grow hair, crawl, sit, or wean. Prenatal drug treatment does not significantly change maternal behaviour toward pups because the frequency of active and passive nursing and pup grooming remained comparable in the drug-treated groups and normal control group. The frequency of dam-related behaviours (self-grooming, eating and drinking, and wandering active or passive) in drug-treated dams was also comparable to normal control dams.

The frequency of nest-building activity was similar in drug-treated mother and normal control mothers.

Dams treated with the drug proceeded normally post-delivery and was terminated on day 21. Drug-treated dams did not present any abnormal type of behavior and they could not be physically distinguished from normal control dams, throughout gestation. The overall appearance of the normal control and drug-treated offspring was healthy and no differences were noted in litter size and offspring. No differences were found in the gestation length of control and drug-treated groups, nor were differences observed in litter size or number of stillborn pups.

No external signs of malformation were detected in the pups. There was no mortality in pups between drug treated groups compared with normal control group. From PND 1 to PND 21 there were no differences between the drug-treated group and the control group in the mean pups' body weight. There were no differences between the maternal groups in the number of pups per litter. The groups did not differ in the number of stillbirths, the viability index, and the lactation index. There were no significant differences in body weight, length or rate of growth of the offspring between the drug-treated groups and normal control group (PND 1 to 21) indicating normal postnatal growth unaffected by the prenatal drug treatment.

Physical development markers showed no drug treatment effect. All groups exhibited incisor eruptions (postnatal day 9) and eye openings (postnatal day 14). Pups of the drug-treated groups did not differ from their normal control counterparts in the time of pinna detachment. By PND 4, all of pups in all groups had their pinna detached. Pups born to drug-treated mothers did not differ from normal control pups in the time of incisor eruption and in the time of eye opening.

The locomotors activity of the pups in drug-treated groups was comparable to that of normal control group.

Example 13

Evidence of Bioavailability

The pharmacokinetic data of RetroMAD1 was derived in 6-8 weeks female ICR mice. Mice (48) were administered with single dose of RetroMAD1 of 70 ul per mouse which is a 50× dose of 0.2 mg/kg body weight given orally for ten days.

Figure 12:
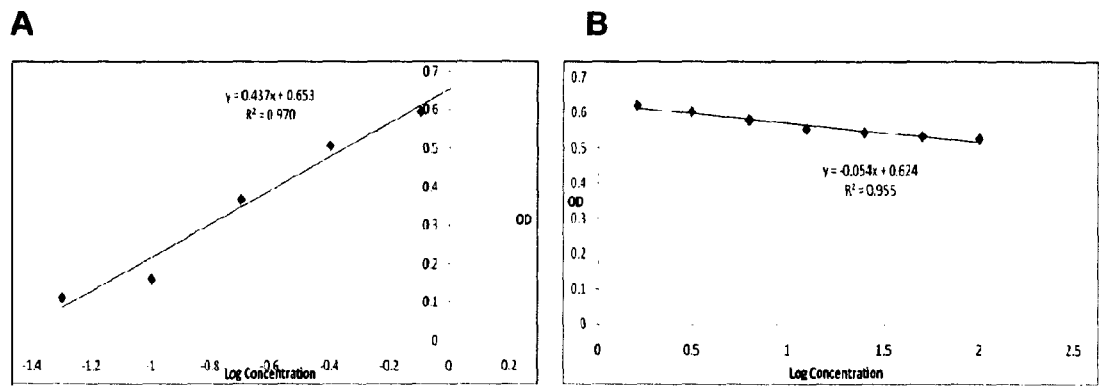
FIGS. 12A and B are standard curves to determine the concentration of RetroMAD1 in cat serum using capture ELISA.
Figure 13:
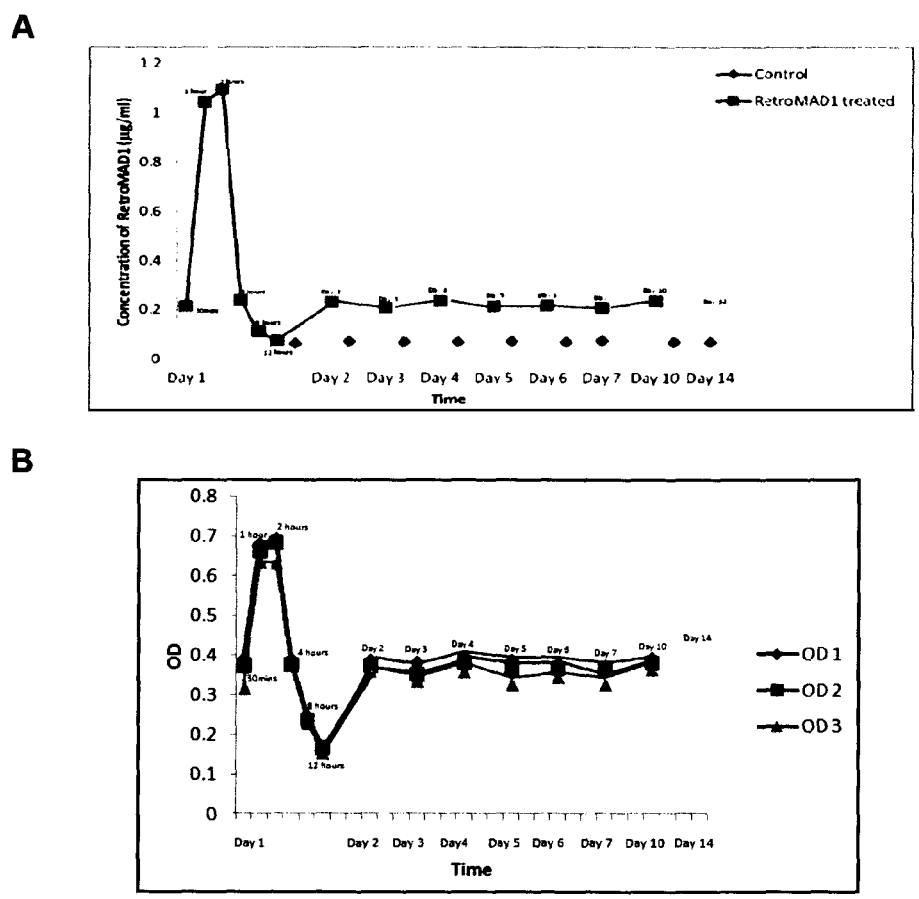
FIG. 13A is a graph showing the concentration of RetroMAD1 in the serum of control and treated mice derived from capture ELISA.
FIG. 13B is a graph showing the triplicate data confirming the excellent conformity of results used to derive RetroMAD1 concentration in the serum in FIG. 13(A).

RetroMAD1 antibody diluted 1:80 in coating buffer (0.2 M sodium carbonate-bicarbonate, ph 9.6) was adsorbed onto 96-well polystyrene ELISA plates. The plates were incubated at 4° C. overnight. Plates were washed three times with 0.05% Tween-20 in PBS 1×. 100 ul/well of mice serum diluted 1:2 in 0.05% BSA in PBS and were added to the wells. After incubation at 37 C for 1 h, plates were washed similarly and 100 μl of anti RetroMAD1 positive human serum diluted 1:2000 in 0.05% BSA in PBS, was added. This antibody was obtained from the Department of Medical Microbiology, Faculty of Medicine, University Malaya, Malaysia. After incubation at 37° C. for 1 h, plates were washed and 100 μl/well Rabbit anti-human IgG HRP conjugate diluted 1:6000 in 0.05% BSA in PBS, was added. After incubation at 37° C. for 1 h in the dark, plates were washed and 100 ul/well of OPD added to each well. Plates were incubated in the dark for 30 min at room temperature and reaction stopped with 50 ul/well of 4N H2SO4. Optical densities (OD) were measured at 490 nm and 600 nm as background. All OD readings were then converted to Log values to obtain concentrations in ug/ml and the standard curves provided in FIG. 12. The results of the tests are provided in Table 16 and FIGS. 13A and B. The PK/PD data showed that RetroMAD1 was detected in the serum as early as 30 min post feeding at about 0.2 μg/ml that reached a maximum at 1-2 hrs at 1-1.1 μg/ml before falling again to about 0.2 μg/ml at 4 hrs. By 12 hrs post feeding, levels were almost similar to the unfed controls indicating that the protein had been completely metabolized. Subsequent daily sampling 30 min post feeding indicated levels around 0.2 μg/ml. These data suggest bioavailability of the drug.

TABLE 16

Results of bioavailability test

| Day | Time | OD 1 | OD 2 | OD 3 | Average | y = 0.437x + 0.6533 | |
|---|---|---|---|---|---|---|---|
| Day 1 | 30 mins | 0.391743 | 0.374396 | 0.317144 | 0.361094333 | −0.668662853 | 0.214455479 |
| | 1 hr | 0.683215 | 0.56296 | 0.637182 | 0.661119 | 0.017892449 | 1.042059335 |
| | 2 hr | 0.632854 | 0.685153 | 0.692951 | 0.670319333 | 0.038945843 | 1.093819957 |
| | 4 hr | 0.375195 | 0.376294 | 0.391285 | 0.380924667 | −0.623284516 | 0.238075927 |
| | 8 hr | 0.234143 | 0.247498 | 0.229154 | 0.236931667 | −0.952787948 | 0.111483874 |
| | 12 hr | 0.16735 | 0.154429 | 0.16771 | 0.163163 | −1.121594966 | 0.075579677 |
| | Control | 0.132178 | | | 0.132178 | −1.192498856 | 0.064194991 |
| Day 2 | 30 mins | 0.387735 | 0.359613 | 0.372947 | 0.373431667 | −0.640430969 | 0.228859546 |
| | Control | 0.152749 | | | 0.152749 | −1.145425629 | 0.07154419 |
| Day 3 | 30 mins | 0.334864 | 0.352838 | 0.382846 | 0.356849333 | −0.678376812 | 0.209711955 |
| | Control | 0.149021 | | | 0.149021 | −1.153956522 | 0.070152553 |
| Day 4 | 30 mins | 0.360735 | 0.382153 | 0.395173 | 0.379353667 | −0.626879481 | 0.236113337 |
| | Control | 0.148574 | | | 0.148574 | −1.154979405 | 0.069987518 |
| Day 5 | 30 mins | 0.386559 | 0.367518 | 0.327878 | 0.360651667 | −0.66967582 | 0.213955857 |
| | Control | 0.156574 | | | 0.156574 | −1.136672769 | 0.073000735 |
| Day 6 | 30 mins | 0.347217 | 0.369173 | 0.3797746 | 0.3653882 | −0.658837071 | 0.219362774 |
| | Control | 0.14443 | | | 0.14443 | −1.164462243 | 0.068475901 |

Each day blood samples were drawn from the heart of three mice and one control. For the first day after the feed, the blood was collected after 30 min, 1 hour, 2 hour, 4 hour, 8 hour and 12 hours after oral administration and for the following days (up to day 10) the blood was collected just 30 min after administration. Each time point consisted of 3 mice fed orally with the drug and one control given PBS. Plasma concentration of RetroMAD1 was determined using an in house developed ELISA.

ELISA for Detecting RetroMAD1 in Mice Sera: In House Capture ELISA with Anti Human-IgG-HRP To prepare the capture antibody a cat was fed daily (1× cat dose refer Example 4) with RetroMAD1 and after 6 months blood harvested and serum extracted. This serum was used as the capture antibody. 100 ul/well of this polyclonal cat anti- Example 14

Thermostability Trials

Figure 14:
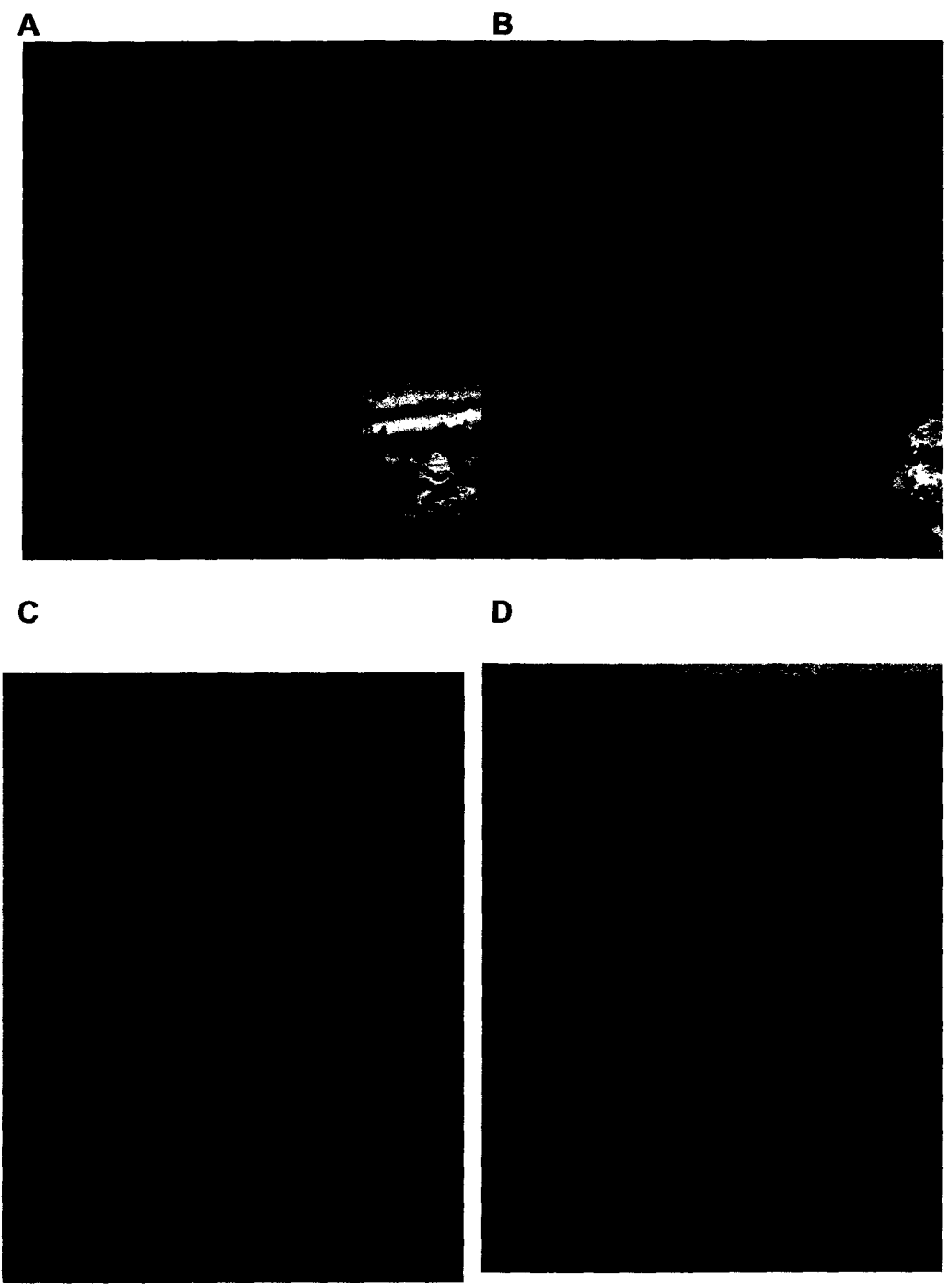
FIG. 14 are SDS-page results showing the thermostability of RetroMAD1.

Protein stability under different temperatures was determined by keeping RetroMAD1 in multiple 1.5 ml Eppendorf tubes at 4 C in a conventional refrigerator, 27 C+/−1 C in a laboratory which had 24 hour air-conditioning that maintained a narrow temperature range, in a conventional incubator oven set at 37 C and in a laboratory oven set at 50 C. As RetroMAD1 is a protein of 41.2 kDa, running it on an SDS-PAGE gel and comparing the gel band of the sample stored at 4 C with those kept at the other temperatures will reveal its stability. Up to day 7, the intensity of the gels remained the same irrespective of temperature up to 50 C. Up to day 30, the intensity was similar for the samples stored at 4 C, 27+/−1 C and 37 C. Unfortunately, a sample for 50 C was not kept for the 30$^{th}$ day. Based on the results as shown in FIG. 14, RetroMAD1 is stable up to 50 C for a week and 37 C for a month.

Example 15

HPLC Detection Method

To optimize a detection method and to determine the detection limit for RetroMAD1 by using HPLC.

Different concentrations of drug ranged from 1 μg/ml to 500 μg/ml were prepared by diluting 3.5 mg/ml of RetroMAD1 stock solution with miliQ water. 10 μl of RetroMAD1 was injected and was eluted through the column in an isocratic elution where composition of the mobile phase was held constant during the entire elution. RetroMAD1 was detected by UV absorption at 280 nm. Data was analyzed from the chromatogram. Optimization was repeated until the peak is resolved.
Change of Chromatographic Parameters Chromatographic parameters were adjusted to get a resolved peak. Parameters adjusted are concentration and ratio of mobile phase, range of UV absorbance, run time and temperature. Chromatographic detection of RetroMAD1 was performed by using Eclipse XDB-$C_8$ column (4.6×250 mm) 5 um as stationary phase with mobile phase comprising of 0.01M Phosphate Buffer Saline pH 7.2 and Acetonitrile (50:50) at a flow rate of 1.0 ml/min and UV detection at 280 nm at a run time of 15 minutes.

Figure 15:
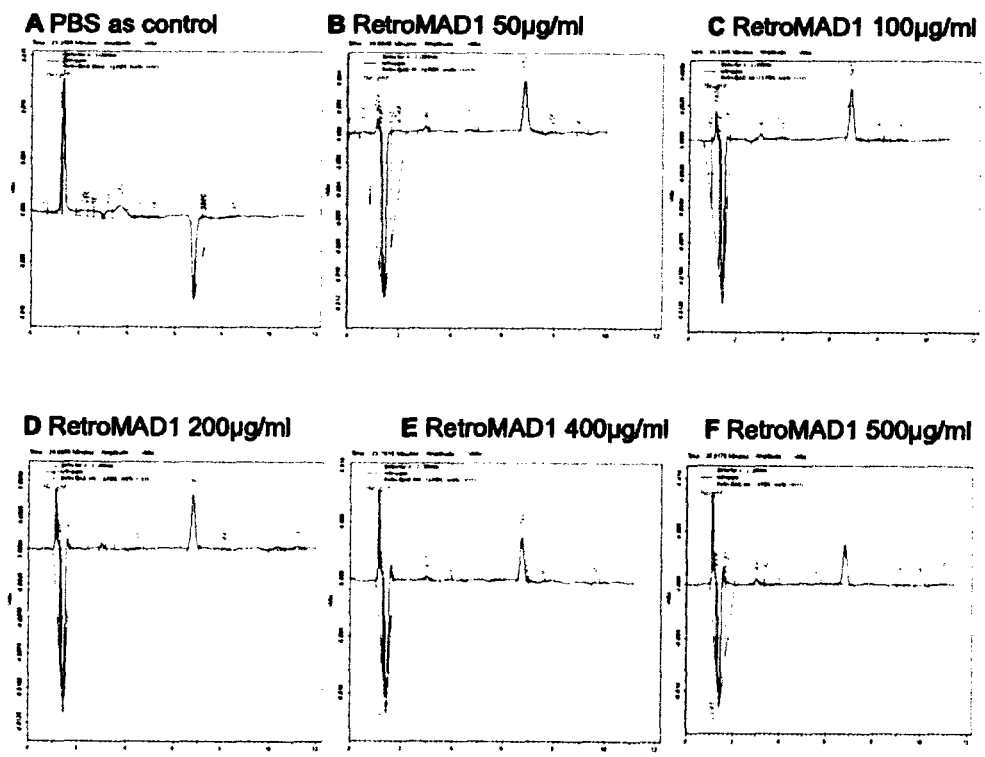
FIG. 15 is a chromatogram showing peaks for (A) PBS control (B) 50 µg/ml, (C) 100 µg/ml, (D) 200 µg/ml, (E) 400 µg/ml and (F) 500 µg/ml of RetroMAD1 using HPLC.

Chromatograms as shown in FIG. 15 are results of detection of RetroMAD1 using HPLC. The first peak at 1.2 minutes is when unbound compounds were eluted first; the second peak at 1.4 minutes is the background cause by the UV. Peak at 6.8 minutes is when RetroMAD1 is detected. Current optimized HPLC detection condition is by using Eclipse XDB-$C_8$ column (4.6×250 mm) 5 um as stationary phase, isocratic elution with A: 0.01M Phosphate Buffer Saline (50%) and B: Acetonitrile (50%) in 15 minutes, column temperature of 30° C., flow rate 1 mL/min; UV detection 280 nm. And current detection limit of RetroMAD1 is 50 μg/ml.

Example 16

Antiviral Activity of A-B and B-C Combinations

Figure 16:
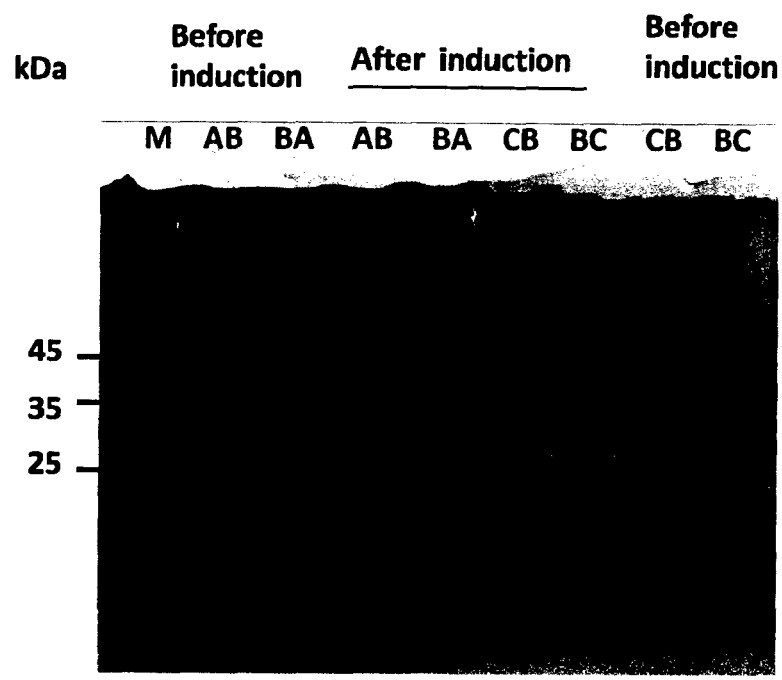
FIG. 16 is a picture of a gel showing the expression of AB, BA, BC and CB before and after induction. Proteins were analyzed on a 15% SDS-PAGE. M: Unstained Protein Marker (Fermentas).

After discovering that RetroMAD1 showed significant antiviral activity, it was decided to test the antiviral activity of the component polypeptides in A-B; B-A as well as B-C; C-B configurations. Polypeptide A (Retrocyclin 101) was fused with polypeptide B (Mormodica anti-HIV protein 30) in the same manner as was done earlier with RetroMAD1. Then, polypeptide B was fused with polypeptide C (Dermaseptin 1) and post-treatment anti-HSV2 activity compared in the same manner as was done previously with RetroMAD1. To determine the effect of attachment at the N and C terminals, A-B was also expressed as B-A and B-C was also expressed as C-B. The evidence of these proteins expressed in inclusion bodies is found in FIG. 16.

Figure 17:
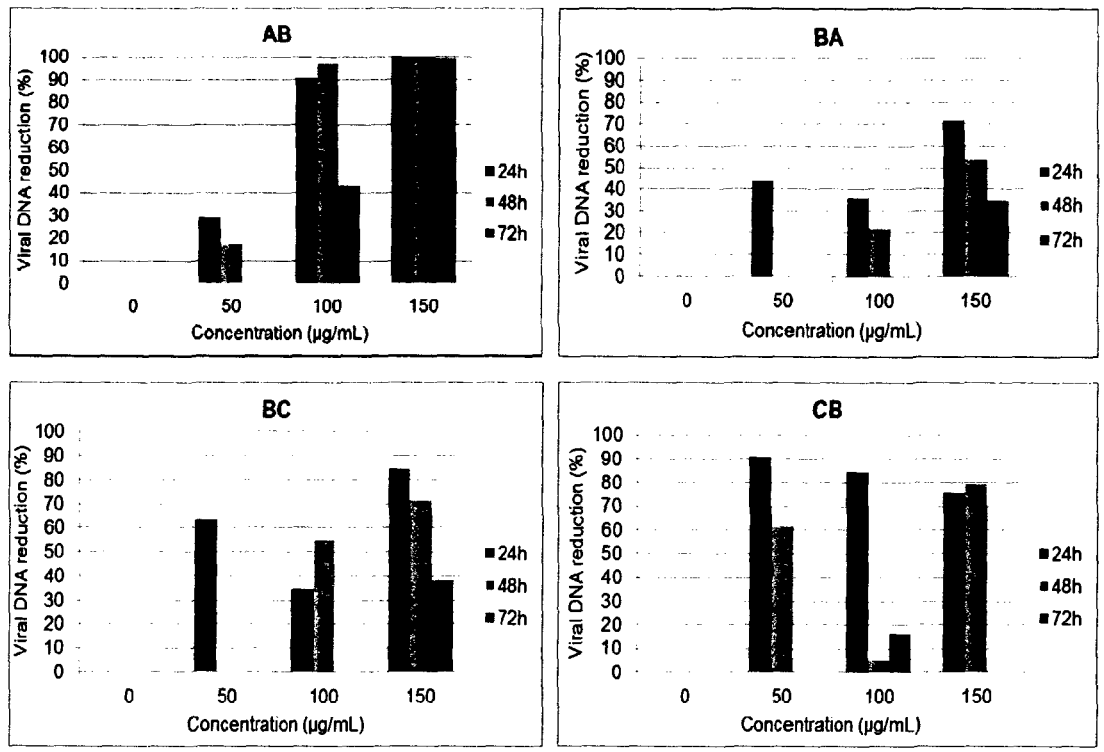
FIG. 17 are graphs showing the antiviral activity against Herpes Simplex Virus-2 (HSV-2) of peptides with structure A-B, B-A, B-C and C-B.

Dose dependent viral reduction was seen in all cases. Only A-B fusion protein gave results comparable with earlier tests on HSV-2 in post-treatment for RetroMAD1 (A-B-C). It was also shown that A-B was superior to B-A revealing that N or C terminal attachment made a difference. Results are shown in Table 17 and FIG. 17.

It was evident that at 150 μg/ml, A-B consistently gave very high antiviral activity that was not diminished even at 72 h while for B-A, antiviral activity decreased in a linear fashion over time. A similar trend was also noted for B-C while for C-B, there was negligible antiviral activity at 72 h for the highest dose.

When only polypeptide A (Retrocyclin 101) and B (MAP30) were used on an antiviral assay of HSV2, post-treatment results showed that the position of A at the N or C terminal of B made a significant difference in antiviral activity of the peptide.

TABLE 17

Drugs in inclusion bodies, post treatment only

| Drug | ug/ml | Percent viral reduction 24 hrs | Percent viral reduction 48 hrs | Percent viral reduction 72 hrs |
|---|---|---|---|---|
| AB | 50 | 29.07 | 17.64 | 0 |
|    | 100 | 90.64 | 97.14 | 43.02 |
|    | 150 | 99.85 | 99.80 | 99.06 |
| BA | 50 | 43.58 | — | 0 |
|    | 100 | 36.11 | 22.03 | 0 |
|    | 150 | 71.33 | 53.77 | 34.82 |
| BC | 50 | 63.23 | 0 | 0 |
|    | 100 | 34.82 | 55.35 | 0 |
|    | 150 | 84.61 | 71.47 | 38.29 |
| CB | 50 | 91.00 | 61.73 | 0 |
|    | 100 | 84.69 | 5.32 | 16.40 |
|    | 150 | 75.79 | 79.46 | 0 |

Example 17

Trials for Other Combinations of Polypeptides A, B and C

It was decided to test another 4 fusion protein combinations to study how easy it was to develop a second potential lead drug after RetroMAD1. These were:—
AVBD103-MAP30-MYTILINC10C (Amatilin)
RETEROCYCLIN-GAP31-DERMASEPTIN1 (RetroGAD1)
HKABF-PAP1-V1 (Kudapan)
CAD-TAP29-DAP30-LATARCIN 2A (Catadarcin)

Amatilin comprises of Avian 8-Defensin 103 (AVBD103) as polypeptide A, a non-β-Defensin from the penguin, MAP30 as used in RetroMAD1 as polypeptide B and Mytilin C10C, a Cationic Antimicrobial Peptide from the Mussel as polypeptide C.

RetroGAD1 was similar to RetroMAD1 except that the MAP30 was replaced by GAP31 as polypeptide B.

Kudapan comprised of polypeptide A as the CAP, *Hippocampus kuda* antibacterial factor HKABF, Pokeweed antiviral protein 1, an RIP as polypeptide B and de Novo sequence known only as V2 as polypeptide C (V2 is presented in 'De Novo design of potent antimicrobial peptides'—Antimicrobial Agents and Chemotherapy (2004) pg 3349-3357.)

Catadarcin comprised of 2 CAP heterologous repeats where CAD was a Cercropin A and Cercropin D tandem sequence as polypeptide A1 and A2. Polypeptide B comprised of the active core fragment of the TAP29 RIP fused with the entire DAP30 RIP sequence while Latarcin 2A was a homologous tandem repeat of the spider antimicrobial peptide Latarcin.
Cells and Viruses Vero cells (African Green monkey kidney cell line) were obtained from American Type Culture Collections, Rockville, Md. They were used as the host cells for HSV-2. The cells were cultured using Dulbeco's Modified Eagle Medium (DMEM), supplemented with 10% Foetal bovine serum (FBS).

Herpes simplex 2 (HSV-2) virus stocks were obtained by inoculating monolayer of Vero cells in a 75 cm² tissue culture flasks with virus in maintenance medium containing 2% FBS and the cells were allowed to continue propagating at 37° C. for 4 days until the cytopathic effect (CPE) are confirmed. The cells and supernatant were then harvested by gentle pipetting. Cell debris was removed by centrifugation at 1500 rpm for 10 minutes. The viral supernatant was aliquoted in 1.5 mL tubes and stored at −80° C. until further use.

Virus Titration by Plaque Assay

HSV-2 virulence was titrated by plaque assay using Vero cells. Briefly, Vero cells were seeded in 24-well plates ($2\times10^5$ cells/well) in 500 µL of DMEM with 2% FBS and serial dilutions of viral supernatants in 100 uL of DMEM with 1% FBS were added to the wells. The inoculated cells were further incubated to allow cell propagation and virus adsorption for 4 h. Subsequently, a mixture of agar overlay was added and the plates were incubated at 37° C. for 4 days or until formation of plaques. The plaques were visualized after removal of agar plug and staining with 0.1% naphthalene black solution in 6% acetic acid glacial. The viral titre is expressed as plaque forming unit (PFU) per milliliter.

Cytotoxicity Assay

Prior to screening the peptides for their antiviral properties, all the eight peptides (Amatilin, Catadarcin, Kudapan and RetroGAD1) were subjected to cytotoxicity assay in order to identify the maximal concentration which could be non-toxic to Vero cells. The cytotoxic activity of the peptides was quantified using MTS-based cell titer 96 non-radioactive cell proliferation assay which is composed of solutions of a novel tetrazolium compound 3-(4,5-dimethylthiazol-2-yl)-5-(3-carboxymethoxyphenyl)-2-(4-sulphonyl)-2H-tetrazolium, inner salt, MTS and an electron coupling reagent (phenazine methosulphate; PMS) (Promega, Madison, Wis.). The MTS growth assay was performed according to the instructions provided by the manufacturer (Promega). Prior to each experiment, cells from a number of flasks were washed thoroughly with phosphate buffered saline (PBS) (1×), harvested by treatment at 37° C. with a solution of Trypsin-EDTA (1×) and re-suspended in the culture medium. The cells were then counted and were seeded in the wells of a 96-well flat-bottom plate at a concentration of $1\times10^4$ cells/well. After 24 h of incubation at 37° C. in a humidified $CO_2$ atmosphere (5% $CO_2$), cells were exposed to increasing concentrations of the peptides. Serial dilutions of the peptides from 100 µg/ml were prepared in culture medium and added to the cultures. Each dilution was always tested in triplicate and in each experiments carried out, 3 control wells were included. Control wells contained cells with culture medium without the extract and negative control wells contained only culture medium with different concentrations of the extract in the absence of cells (to substract the background value due to the drug in the culture medium). After 24, 48 and 72 h of incubation, the maximal concentration of the extract that did not exert toxic effect which is regarded as the maximal non toxic concentration (MNTD) was determined using MTS assay. At the end of each time point, MTS solution was added and further incubated for 1 h. The absorbance was measured at 490 nm using a 96-well microplate reader (GLOMAX, Promega). Absorbance is directly proportional to the number of live cells in the culture. At least three replications for each sample were used to determine the anti-proliferative activity. Results were reported as mean±S.D.

$$\text{Percentage of cell viability} = \frac{\left[\begin{array}{c}\text{Mean } OD \text{ of the test group} - \\ \text{Mean of negative control group}\end{array}\right]}{\left[\begin{array}{c}\text{Mean } OD \text{ of the control group} - \\ \text{Mean of negative control group}\end{array}\right]} \times 100\%$$

The MNTD was calculated from dose-response curves. The MNTD, which altered neither the morphology nor the cell survival rate, was recognized as MNTD.

Antiviral Bioassay

Pre-treatment assay: Vero cells were seeded in 24-well culture plates at concentration of $1\times10^5$ cells per well and incubated for 24 h. Before virus inoculation, maximal non toxic dose of the peptides were added to the cells and incubated for 24 h. After 24 h of incubation with the peptides, herpes simplex virus-2 (HSV-2) at MOI of 0.1 was inoculated onto the Vero cells for 1 h with occasional rocking. The virus was removed and the cells replaced with fresh DMEM. The cultures were incubated for 24, 48 and 72 h at 37° C. under 5% $CO_2$ atmosphere.

Simultaneous treatment assay: Vero cells were seeded in 24-well culture plates at concentration of $1\times10^5$ cells per well and incubated for 24 h. The peptides were mixed with virus and incubated at 37° C. for 1 h. The mixture was then inoculated onto Vero cells in 24-well culture plates for 1 h with occasional rocking. The solution was removed and the media was replaced with DMEM. The cultures were incubated for 24, 48 and 72 h at 37° C. under 5% $CO_2$ atmosphere.

Post treatment assay: Vero cells were seeded in 24-well culture plates at concentration of $1\times10^5$ cells per well and incubated for 24 h. HSV-2 at MOI of 0.1 was inoculated onto Vero cells in 24-well culture plates for 1 h with occasional rocking. The media was removed and replaced by DMEM containing the peptides. The cultures were incubated for 24, 48 and 72 h at 37° C. under 5% $CO_2$ atmosphere.

At the end of the time period in all antiviral assays the plates were frozen down in −80° C. After 2 cycles of freezing and thawing both supernatant and attached cells were collected. Viral DNA was extracted by extraction kit (Bioneer, South Korea). The eluted DNA was then subjected to RT-PCR.

Quantitative Real-Time PCR

In order to demonstrate the presence or absence of viral RNA in infected Vero cells after treatment with the peptides, Real time PCR was performed. RT-PCR was carried out using iQ SYBR Green Supermix (Bio-Rad, USA), employing HSV-2 group specific primers. After optimization of each of the primer pairs, samples were assayed in a 10 µL reaction mixture containing 2.5 µl of sample DNA, 0.125 ul of each primers, 5.0 µL of SYBR Green mix and 2.25 µl of water. PCR amplification was carried out as follows: an initial denaturation step of 95° C. for 15 min followed by 35 cycles of alternating denaturation (95° C. for 30 sec), primer annealing (60° C. for 30 sec) and primer extension (72° C. for 30 sec). A final extension step of 5 min at 72° C. was included.

Cytotoxicity of Tested Peptides on Vero Cells

The effect of all the four peptides on the growth of Vero cells was examined to rule out any direct cytotoxicity. Monolayer cultures of Vero cells were exposed to increasing concentrations of Amatilin, Catadarcin, Kudapan, and RetroGAD1 after 24, 48 and 72 h of incubation, cell viability was determined using MTS assay. Results as shown in Table 1 indicate that the accepted maximal nontoxic concentrations of the four peptides on Vero cells were less than 30 µg/ml. At the chosen MNTD, the peptides did not impair the cell viability with respect to the untreated control group.

TABLE 18

Maximal non-toxic dose of the peptides on Vero cells.

| Peptide | MNTD, ug/ml | | |
|---|---|---|---|
| | 24 h | 48 h | 72 h |
| Amatilin | 25 | 25 | 25 |
| Catadarcin | 15 | 15 | 15 |

TABLE 18-continued

Maximal non-toxic dose of the peptides on Vero cells.

| Peptide | MNTD, ug/ml | | |
|---|---|---|---|
| | 24 h | 48 h | 72 h |
| Kudapan | 30 | 30 | 30 |
| RetroGAD1 | 30 | 30 | 30 |

The Antiviral Activity of Peptides Against HSV-2

The antiviral activity of all the four peptides was evaluated by pre-, simultaneous- and post-treatment. These three different mode of treatments were carried out to determine the stage at which the peptides exhibit inhibitory activities. Pre- and simultaneous-treatment assays were carried out to test the ability of the peptides in preventing the attachment of HSV-2 to the host cells. Simultaneous treatment also was used to detect possible virucidal effects of the peptides. On the other hand, the post-treatment assay was performed to evaluate whether the peptides are able to inhibit the replication of HSV-2 inside the host cells (Barakat et al., 2010; Kwon et al., 2010) probably as a translational inhibitor.

Figure 18:
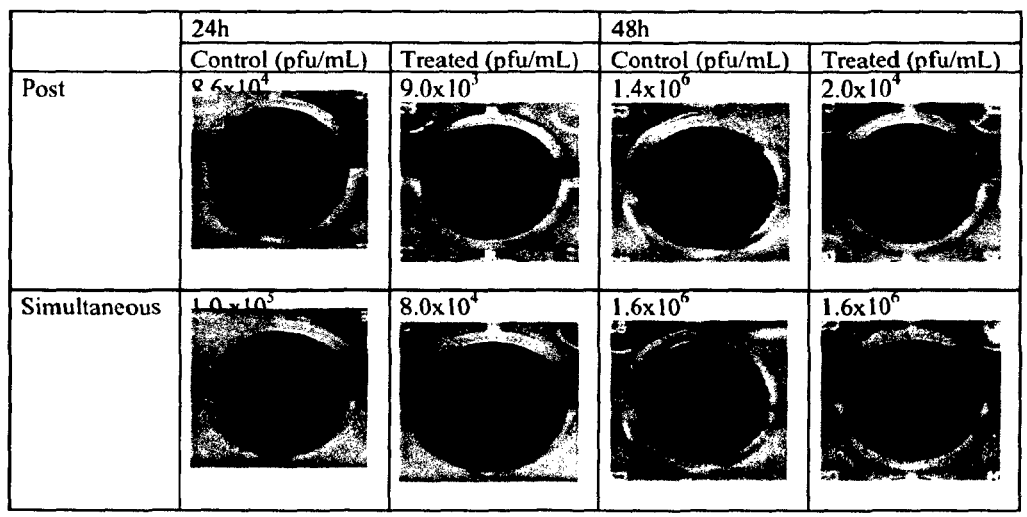
FIG. 18 is a picture showing the inhibitory activity of Amatilin drug (as described in Example 19) using plaque reduction assay against HSV-2

The results obtained suggest that out of the four peptides Amatilin has the strongest inhibitory activity against HSV-2 in post-treatment giving 94.35%, 92.92% and 96.33% of inhibition, respectively after 24, 48 and 72 h at the maximal non-toxic dose (MNTD) of 30 μg/ml (Table 19). This result was confirmed with plaque reduction assay, where it showed 90.00% and 98.57% of reduction in post treatment, respectively, at 48 and 72 h (FIG. 18). However, Amatilin showed only 43.47% 57.14% and 44.97% of inhibition in simultaneous treatment. In pre-treatment, Amatilin caused inhibition only at 24 h. These observations indicate that Amatilin may have affected the viral replication after entry without interference of the viral adsorption to the host cells. The mild inhibitory effects in simultaneous treatment suggest that Amatilin may possess modest direct virucidal effects. The peptides, Catadarcin, Kudapan and RetroGAD1 showed modest inhibitory activity in post-treatment at 24, 48 and 72 h.

Figure 19:
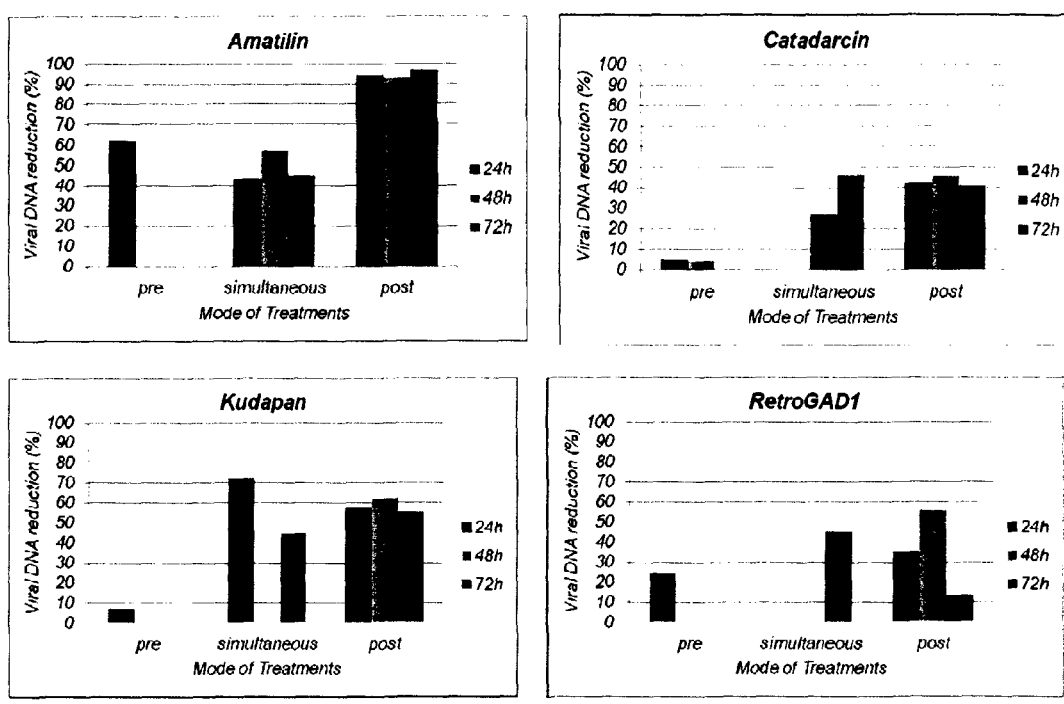
FIG. 19 are four graphs, each showing the percentage of viral DNA reduction with treatment of Amatilin, Catadarcin, Kudapan and RetroGAD1 as described in Example 17.

The inhibitory activity shown during post-treatment suggests the possible ability of the peptides to inhibit viral replication, whereas inhibitory activity during simultaneous shows their direct virucidal effects. The peptides showed no activity or weak inhibitory effect in pre-treatment, suggesting their inability to block the viral absorption to cells. A summary of the results is shown in FIG. 19.

A 'Hit rate' of 1 in 4 may be considered to be a very good rate of success in antiviral Drug Discovery so it appears that by 'cutting and pasting' other sequences, it will be relatively simple to make more antiviral drugs from this class of RIP-CAP fusion proteins.

TABLE 19

Percentage of viral reduction caused by Amatilin, Catadarcin, Kudapan, and RetroGAD1 in pre-, simultaneous and post-treatment determined by PCR.

| Peptides | MNTD (μg/mL) | Treatment — Percentage of viral reduction (%) | | | | | | | | |
|---|---|---|---|---|---|---|---|---|---|---|
| | | Pre | | | Simultaneous | | | Post | | |
| | | 24 h | 48 h | 72 h | 24 h | 48 h | 72 h | 24 h | 48 h | 72 h |
| Amatilin | 25 | 62.00 | 0.00 | 0.00 | 43.47 | 57.14 | 44.97 | 94.35 | 92.92 | 96.33 |
| Catadarcin | 15 | 4.91 | 4.48 | 0.00 | 0.00 | 27.28 | 46.05 | 41.92 | 45.51 | 41.10 |
| Kudapan | 30 | 6.95 | 0.00 | 0.00 | 71.67 | 0.00 | 44.69 | 57.68 | 62.64 | 55.35 |
| RetroGAD1 | 30 | 24.81 | 0.00 | 0.00 | 0.00 | 0.00 | 45.51 | 35.47 | 56.23 | 13.44 |

In summary, the results of the anti-HSV2 assay showed that out of 4 trial sequences, one i.e. Amatilin gave very significant viral reduction results in post-treatment that were comparable to that of RetroMAD1. This meant that it was relatively simple to develop more drugs of this proposed Class as a 'hit-ratio' of 1 out of 4 is considered very significant in Drug Discovery especially for antivirals. When 4 other combinations involving other genes were tested, one in particular, Amatilin, gave comparable results to RetroMAD1 but only in post-treatment. This involved a avian β-Defensin as polypeptide A, the same RIP (polypeptide B) as in Retro-MAD1 and a molluscan antimicrobial peptide as polypeptide C. A Plaque-Reduction Assay was then carried out for Amatilin to countercheck in a visual way the RT-PCR results obtained for simultaneous and post-treatment efficacies and these data was strongly supportive of the RT-PCR data.

REFERENCES

1. Au et. al. (2000); FEBS letters 471:169-172;
2. Barakat, A. B., (2010) Journal of Microbiology and Antimicrobials; 2(3): 23-29;
3. Barbieri et al., (1983); Biochem. J. 215 (433-439);
4. Barbieri, Battelli, & Stirpe, (1993); Biochem, Biophys. Acta 1154: 237;
5. Barbieri, L. Polito, L., Bolognesi, A., Clani, M., Pelosi, E., Farini, V. (2006); Biochim Biophys Acta, 1760(5): 783-792;
6. Bergmeyer H U, (1980); Clin. Chimica. Acta., 105: 147-154;
7. Bolognesi, A., Barbieri, L., Abbondanza, A., Falasca, A. I., Carnicelli, D., Battelli, M. G. (1990); Biochim Biophys Axta, 1087(3): 293-302;
8. Brudno M., (2003b); Bioinformatics; 19 Suppl 1:154-162;
9. Chambery, A., de Donato, A., Bolognesi, A., Polito, L, Stirpe, F., & Parente, A. (2006); Biol Chem, 387(9): 1261-1266;
10. Cole et. al. (2002); PNAS, V99(4):1813-1818;
11. Coleman, W. H., & Roberts, W. K. (1982); Biochim Acta, 696(3): 239-244;

12. de Benito et al., (1995); FEBS Lett.; 360(3):299-302;
13. de Benito et al., (1998); FEBS Lett.; 428(1-2):75-9;
14. Dong, T. X., Ng, T. B., Yeung, H. W., & Wong, R. N. (1994); Biochem Biophys Res Commun, 199(1): 387-393;
15. Hebestreit, P., & Melzig, M. F. (2003); Planta Med, 69(10): 921-925;
16. Huang, P. L., Sun, Y., Chen, H. C., Kung, H. F., Huang, P. L. and Murphy, W. J.; (2000); Anticancer Res., 20: 653-659;
17. Karlin & Altschul (1993); Proc. Natl. Acad. Sci. USA 90: 5873-5877;
18. Kondo, T., Mizukami, H., Takeda, T. & Ogihara, Y. (1996); Biol Pharm Bull, 19(11): 1485-1489;
19. Kwon, H. J., (2010) Virology Journal, 7:307;
20. Lam, S. S., Wang, H. & Ng., T. B. (1998); Biochem Biphys Res Commun, 253(1): 135-142;
21. Lee-Huang et al. (1995); Proc. Natl. Acad. Sci. USA, 92(19):8818-8822;
22. Lorin et. al. (2005); Virology 334:264-275;
23. Malich, G., Markovic, B. and Winder, C. (1994); Toxicology, 124, 179-192;
24. Moon, Y. H., Song, S. K., Choi, K. W., & Lee, J. S. (1997); Mol Cells, 7(6): 807-815;
25. Ng., T. B., Prakash, A., & Tso, W. W. (2002); Protein Expr Purif, 26(1), 9-13;
26. Olivieri, F., Prasad, V., Valbonensi, P., Srivastava, S., Ghosal-Chowdhury, P., Barbieri, L. (1996); FEBS Lett, 396(2-3): 132-143;
27. Phoolcharoen, W et al. (2004); Journal of medical virology, 74(3): 434-441;
28. Prestle, J., Homung, E., Schonfelder, M., & Mundry, K. W. (1992); FEBS Lett, 297(3) 250-252;
29. Pu, Z., Lu, B. Y., Liu, W. Y., & Jin, S. W. (1996); Biochem Biophys Res Commun, 229(1): 287-294;
30. Puri et. al. (2009); Current Molecular Medicine, 9:1080-1094;
31. Ready, M. P., Adams, R, P., & Robertus, J. D. (1984); Biochim Biophys Acta 791(3): 314-319;
32. Rojo, M. A., Arias, F. J., Ferreras, J. M., Iglesias, R., Munoz, R., Citores, L. (1995); Cell Mol Biol (Noisy-le-grand), 41(2): 279-287;
33. Sambrook and Russel, Molecular Cloning: A Laboratory Manual, Cold Springs Harbor Laboratory, New York (2001);
34. Shih, N. J., McDonald, K. A., Girbes, T., Iglesias, R., Kphlhoff, A. J., & Jackman, A. P. (1998); Biol Chem, 379(6), 721-725;
35. Sperti, S., Montanaro, L., Mattioli, A., Testoni, G., & Stirpe, F. (1976); Biochem J, 156(1): 7-13;
36. Tietz N W, Rinker A D, Shaw L M (1983); J. Clin. Chem. Clin. Biochem., 21:731-748;
37. Tse, P. M., F., Ng., T. B., Fong, W. P., Wong, R. N. S., Wan, C. C., Mak, N. K. (1999); The International Journal of Biochemistry & Cell Biology, 31(9): 895-901;
38. VanCompemolle et. al.; (2005); J. Virol. 79(18):11598-11606;
39. Wang G., * Xia Li, and Zhe Wang, (2009); Nucleic Acids Res. 37(Database issue): D933-D937;
40. Wang, H. X., & Ng., T. B. (2000a); Life Sci, 67(21): 2631-2638;
41. Wang, H. X., & Ng. T. B. (2000b); Biochem Biophys Res Commun, 269(1): 203-208;
42. Wang, H. X., & Ng., T. B. (2002); Life Sci, 70(8): 899-906;
43. Wang et. al. (2003); J. Immunol. 170:4708-4716;
44. Wang Z., and Guangshun Wang; (2004); Nucleic Acids Research, Vol. 32, Database issue;
45. Wang, R. N., Dong, T. X., Ng, T. B., Choi, W. T., & Yeung, H. W. (1996): Int J Pept Protein Res, 47(1-2): 103-109;
46. Wu, T. H., Chow, L. P., & Lin, J. Y. (1998); Eur J Biochem, 255(2): 400-408; and
47. Yeung, H. W., Ng., T. B., Wong, N. S., & Li, W. W. (1987); Int J Pept Protein Res, 30(1): 135-140.

The invention claimed is:

1. A recombinant fusion protein comprising at least one Type 1 Ribosome Inactivating Protein (RIP) or fragment thereof, polypeptide B; and
   (i) at least one polypeptide A capable of viral entry inhibition, wherein the polypeptide A has the amino acid sequence set forth in SEQ ID NO: 12; and optionally
   (ii) at least one Cationic AntiMicrobial Peptide (CAP) or fragment thereof, polypeptide C,
   wherein the fusion protein further comprises at least one linker peptide between each of the polypeptides A, B and C and wherein the fusion protein is suitable for oral administration.

2. The fusion protein according to claim 1, wherein the fusion protein comprises the structure A-B-C, A-C-B, C-A-B, C-B-A, B-A-C, B-C-A, A-B—C-C, A-B, or B-A.

3. The fusion protein according to claim 1, wherein the fusion protein comprises polypeptides A, B and C.

4. The fusion protein according to claim 1, wherein the at least one linker peptide between each of the polypeptides A, B and C is a non-labile linker.

5. The fusion protein according to claim 1, wherein the linker peptide comprises the amino acid sequence set forth in SEQ ID NO: 11.

6. The fusion protein according to claim 1, wherein the Type 1 RIP (polypeptide B) is selected from the group consisting of Ebulitins, Nigritins, Amarandins, *Amaranthus* antiviral/RIP, Amaranthin, *Atriplex patens* RIP, *Beta vulgaris* RIP, β-vulgin, *Celosia cristata* RIP, *Chenopodium album* RIP, CAP30B, *Spinacea oleracea* RIP, Quinqueginsin, Asparins, Agrostin, Dianthins, DAPs, *Dianthus chinensis*', Lychnin, Petroglaucin, Petrograndin, *Saponaria ocymoides* RIP, Vacuolas saporin, Saporins, *Vaccaria hispanica* RIP, Benincasins, Hispin, Byrodins, Colocins, *Cucumis figarei* RIP, Melonin, *C. moschata* RIP, Cucurmosin, Moschatins, Pepocin, Gynostemmin, *Gynostemma pentaphyllum* RIP, Gypsophilin, Lagenin, Luffaculin, Luffangulin, Luffin, MORs, Momordin II, Momorcharins, Momorcochin, Momorcochin-S, Sechiumin, Momorgrosvin, Trichoanguin, Kirilowin, α-trichosanthin, TAP-29, Trichokirin, Trichomislin, Trichosanthin, Karasurin, Trichomaglin, Trichobakin, Crotin, Euserratin Antiviral Protein GAP-31, Gelonin, *Hura crepitans* RIP, Curcin, *Jathropa curcas* RIP, Mapalmin, Manutins, α-pisavin, Charibdin, *Hyacinthus orientalis* RIP, Musarmin, *Iris hollandica* RIP, *Cleroendrum aculeatum* RIP, CIPs), Crip-31, Bouganin, *Bougainvilla spectbilis* RIP, *Bougainvillea×buttiana* Antiviral protein 1 (BBAP1), Malic enzymes, MAP-S, pokeweed antiviral proteins (PAP), PD-SI, DP-S2, Dodecandrin, PIP, PIP2, *Phytolacca octandra* antiviral proteins, *Hordeum vulgare* RIP's, *Hordeum vulgare* sub sp. *Vulgare* Translational inhibitor II, *Secale cereale* RIP, Tritin, *Zea diploperemis* RIPs, *Malus×domestica* RIP, *Momordica* Anti-HIV Protein, *Gelonium multiflorum, Mirabilis expansa* 1, phage MU1, betavulgin (Bvg), curcin 2, saporin 6, Maize RIP (B-32), Tobacco RIP (TRIP), Beetins, *Mirabilis* antiviral protein (MAP), Trichosanthin (TCS), luffins, Momorcharins, Ocymoidin, Bryodin, Pepopsin, β-trichosanthin, Camphorin, YLP, Insularin, Barley RIP, Tritins, Lamjarin, and *Volvariella volvacea* RIP.

7. The fusion protein according to claim 1, wherein the CAP (polypeptide C) is selected from the group consisting of Cyclotides, Siamycins, NP-06, Gramicidin A, Circulins, Kalatas, Ginkbilobin, Alpha-Basrubin, Lunatusin, Sesquin, Tricyclon A, Cycloviolacins, Polyphemusins, hfl-B5, Protegrins (Pig Cathelicidin), Rat Defensins, Human B-defensins, Temporins, Caerins, Ranatuerins, Reptile Defensin, Piscidins, Lactoferricin B, Rabbit Neutrophil peptides, Rabbit a-Defensin, Retrocyclins, Human α-Defensins, Human β-defensin III (HBD3), Rhesus minidefensin (RTD-1,θ-defensin), rhesus θ-defensins, Human neutrophil peptides, Cecropin As, Melittin, EP5-1, Magainin 2s, hybrid (CE-MA), hepcidin TH1-5, Epinecidin-1, Indolicidin, Cathelicidin-4, LL-37 Cathelicidin, Dermaseptins, Maximins, Brevinins, Ranatuerins, Esculentins, Maculatin 1.3, Maximin H5 and Piscidins, Mundticin KS Enterocin CRL-35, Lunatusin, FK-13 (GI-20 is a derivative), Tachyplesins, Alpha-MSH, Antiviral protein Y3, Palustrin-3AR, Ponericin L2, Spinigerin, Melectin, Clavanin B, Cow cathelicidins, Guinea pig cathelicidin CAP11, Sakacin 5X, Plectasin, Fungal Defensin, GLK-19, lactoferrin (Lf) peptide 2, Alloferon 1, Uperin 3.6, Dahlein 5.6, Ascaphin-8, Human Histatin 5, Guineapig neutrophil peptides, Mytilins, EP5-1,Hexapeptide (synthetic) Corticostatin IV Rabbit Neutrophil peptide 2, Aureins, Latarcin, Plectasin, Cycloviolins, Vary Peptide E, Palicourein, VHL-1, and Buforins.

8. The fusion protein according to claim 1, wherein the Type 1 RIP is MAP30, and the CAP is a Dermaseptin.

9. The fusion protein according to claim 8, wherein the Dermaseptin is Dermaseptin 1.

10. The fusion protein according to claim 1, comprising the amino acid sequence set forth in SEQ ID NO: 1.

11. A pharmaceutical composition comprising a fusion protein according to claim 1 further comprising at least one pharmaceutically acceptable carrier, excipient, diluent and/or detergent.

12. The pharmaceutical composition according to claim 11, wherein the composition is suitable for oral administration.

13. An isolated nucleic acid molecule capable of expressing the fusion protein according to claim 1.

14. A process of producing a fusion protein according to claim 1 comprising culturing a host cell comprising an isolated nucleic acid molecule capable of expressing the fusion protein according to claim 1 under conditions such that the fusion protein is expressed.

15. The process of claim 14, wherein the peptide A has been re-folded.

16. A method of treating a viral infection in a vertebrate or invertebrate in need thereof, comprising administering to the vertebrate or invertebrate an effective amount of the fusion protein according to claim 1.

* * * * *